United States Patent
Fluga

(10) Patent No.: US 12,357,667 B2
(45) Date of Patent: Jul. 15, 2025

(54) NUTRACEUTICAL FORMULATIONS TO PREVENT, TREAT, AND INHIBIT EXCESS CYTOKINES, SARS-CoV-2 SPIKE PROTEINS, AND mRNA VACCINE SPIKE PROTEINS

(71) Applicant: Pono Lifestyle Colorado, LLC, Aurora, CO (US)

(72) Inventor: Mark A Fluga, Negaunee, MI (US)

(73) Assignee: Pono Lifestyle, LLC, Wheat Ridge, CO (US)

( * ) Notice: Subject to any disclaimer, the term of this patent is extended or adjusted under 35 U.S.C. 154(b) by 133 days.

(21) Appl. No.: 17/815,878

(22) Filed: Jul. 28, 2022

(65) Prior Publication Data

US 2023/0038577 A1    Feb. 9, 2023

Related U.S. Application Data

(60) Provisional application No. 63/226,197, filed on Jul. 28, 2021.

(51) Int. Cl.
| | | |
|---|---|---|
| *A61K 36/73* | (2006.01) | |
| *A23L 33/00* | (2016.01) | |
| *A23L 33/105* | (2016.01) | |
| *A23L 33/155* | (2016.01) | |
| *A61K 31/05* | (2006.01) | |
| *A61K 31/095* | (2006.01) | |
| *A61K 31/122* | (2006.01) | |
| *A61K 31/352* | (2006.01) | |
| *A61K 31/593* | (2006.01) | |
| *A61K 33/30* | (2006.01) | |
| *A61K 36/9066* | (2006.01) | |
| *A61K 38/06* | (2006.01) | |
| *A61K 38/48* | (2006.01) | |

(52) U.S. Cl.
CPC ............ *A61K 36/73* (2013.01); *A23L 33/105* (2016.08); *A23L 33/155* (2016.08); *A23L 33/40* (2016.08); *A61K 31/05* (2013.01); *A61K 31/095* (2013.01); *A61K 31/122* (2013.01); *A61K 31/352* (2013.01); *A61K 31/593* (2013.01); *A61K 33/30* (2013.01); *A61K 36/9066* (2013.01); *A61K 38/06* (2013.01); *A61K 38/4873* (2013.01)

(58) Field of Classification Search
None
See application file for complete search history.

(56) References Cited

U.S. PATENT DOCUMENTS

| | | |
|---|---|---|
| 6,566,401 B2 | 5/2003 | Herzenberg et al. |
| 6,576,267 B2 | 6/2003 | Gelber et al. |
| 9,241,911 B2 | 1/2016 | Miller |
| 11,026,909 B1 | 6/2021 | Raju et al. |
| 11,034,655 B1 | 6/2021 | Vidhani et al. |
| 11,116,818 B2 | 9/2021 | Choe et al. |
| 11,255,855 B1 | 2/2022 | Huang et al. |
| 11,266,707 B2 | 3/2022 | Ichim et al. |
| 11,324,246 B1 | 5/2022 | Weis |
| 2011/0305765 A1 | 12/2011 | Mathur et al. |
| 2014/0141082 A1 | 5/2014 | Gao |
| 2016/0000854 A1 | 1/2016 | Osborne et al. |
| 2018/0140709 A1 | 5/2018 | Chancey |
| 2018/0271805 A1 | 9/2018 | Mezo |
| 2019/0169593 A1 | 6/2019 | Tarsio et al. |
| 2019/0192444 A1 | 6/2019 | Barzilay et al. |
| 2019/0313681 A1 | 10/2019 | Rosenstein |
| 2020/0060322 A1 | 2/2020 | Dimitrelos et al. |
| 2020/0138776 A1 | 5/2020 | Signorile |
| 2021/0220422 A1 | 7/2021 | Parker |
| 2021/0369674 A1 | 12/2021 | Wan |
| 2022/0016196 A1 | 1/2022 | Yimam et al. |

OTHER PUBLICATIONS

Stasilowicz, International Journal of Molecular Sciences, 22, 2021 (Year: 2021).*
Amazon, Vaddmaan Astaxanthin++—60 Capsules, Amazon.in, May 16, 2019, accessed at https://www.amazon.in/Vaddmaan-Astaxanthin-Capsules-Curcumin-Antioxidant/dp/B07T71B5ZD?th=1, sheets 1, 4.
Goddek, S., 'Vitamin D3 and K2 and their potential contribution to reducing the COVID-19 mortality rate', International Journal of Infectious Diseases, Jul. 26, 2020, vol. 99, pp. 286-290.
Hernández, M. D. et al., 'Evolution of COVID-19 patients treated with ImmunoFormulation, a combination of nutraceuticals to reduce symptomatology and improve prognosis: a multi-centred, retrospective cohort study', medRxiv, Dec. 15, 2020, sheets 1-19.
Mrityunjaya, M. et al., "Immune-boosting, Antioxidant and Anti-inflammatory Food Supplements Targeting Pathogenesis of COVID-19", Frontiers in Immunology, Oct. 7, 2020, vol. 11, Article No. 570122, pp. 1-12.

(Continued)

*Primary Examiner* — Susan T Tran
*Assistant Examiner* — William Craigo
(74) *Attorney, Agent, or Firm* — Capitol City TechLaw, PLLC; Samuel P. Burkholder

(57) ABSTRACT

Combinations of cannabinoids, vitamins, trace elements, bioactive components, bioflavonoid polyphenols, proteolytic enzymes, amino acids, and antioxidants which work independently and synergistically for the prevention, treatment, and inhibition of excess cytokines caused by the immune response to extreme viral and bacterial infections, including the inhibition of COVID-19, Rhinovirus and/or other virus spike proteins and mRNA vaccine spike proteins from attaching to body organ cells, penetrating cell membranes, and the replication of virus particles and spike proteins inside the cells. Inhibition of inflammation and prevention of long-term side effects, health issues (long-haulers), and disease caused by the SARS-CoV-2 and its variants, Rhinovirus, other viruses, bacteria, and mRNA vaccines are provided by the nutraceutical compositions. Specific combinations of these compounds work synergistically to increase the efficacy of the independent nutraceuticals in treatment.

5 Claims, No Drawings

(56) References Cited

OTHER PUBLICATIONS

Nguyen, L. C. et al., 'Cannabidiol Inhibits SARS-COoV-2 Replication and Promotes the Host Innate Immune Response', bioRxiv, Mar. 10, 2021, pp. 1-15.
Pal, A. et al., 'Zinc and COVID-19: basis of current clinical trials', Biological Trace Element Research, Epub. Oct. 22, 2020, vol. 199, pp. 2882-2892.
Product catalog, #820 EPIC (Metabolic NO/ONOO Micro Antioxidant), Systemic Formulas, Oct. 2016, sheet 1.
International Search Report, issued on Dec. 30, 2022, in corresponding PCT Application PCT/US2022/074271 by Korean Intellectual Property Office, Korea.

\* cited by examiner

NUTRACEUTICAL FORMULATIONS TO PREVENT, TREAT, AND INHIBIT EXCESS CYTOKINES, SARS-CoV-2 SPIKE PROTEINS, AND mRNA VACCINE SPIKE PROTEINS

CROSS-REFERENCE TO RELATED APPLICATION

The present application claims benefit from earlier filed U.S. Provisional Application No. 63/226,197, filed Jul. 28, 2021, the disclosure of which is hereby incorporated by reference in its entireties for all purposes.

BACKGROUND

Field of Invention

The present disclosure relates to a method of prevention and treatment for SARS-CoV-2, Rhinovirus, and/or other viruses that bind to the ACE2 receptor and/or other receptors and/or directly to a cell's plasma membrane. Prevention and treatment is administered in a therapeutically effective amount of a combinations of cannabinoids, vitamins, trace elements, bioactive components, bioflavonoid polyphenols, proteolytic enzymes, amino acids, and antioxidants that work both independently and synergistically for the prevention, treatment, and inhibition of excess cytokines caused by the immune response to extreme viral and bacterial infections, the inhibition of COVID-19, Rhinovirus and/or other virus spike proteins and mRNA vaccine spike proteins from attaching to body organ cells, penetrating cell membranes, and the replication of virus particles and spike proteins inside the cells. In addition, these unique combinations of compounds inhibit inflammation and prevent long-term side effects and health issues (long-haulers) caused by the SARS-CoV-2 and its variants, Rhinovirus, other viruses, bacteria, and mRNA vaccines. Furthermore, certain of these antioxidants can cross the blood-brain barrier to inhibit cytokine, viral spike protein, and mRNA vaccine spike protein damage done to cells in the brain and the central nervous system. Multiple combinations of these compounds work synergistically to increase the efficacy of independent compounds targeting the inhibition of excess cytokines, COVID spike proteins, mRNA vaccine spike proteins, and inflammation.

Discussion of the Related Art

U.S. Pat. No. 11,266,707, Ichim, et al., Mar. 8, 2022: addresses nutraceuticals for the prevention, inhibition, and treatment of SARS-CoV-2 and associated COVID-19 by enhancing T-cell efficacies. In addition, excess cytokines (cytokine storm) are addressed by the patent in that they claim reduced inflammation resulting from the use of sulforaphane.

U.S. Pat. No. 11,255,855. Huang, et al., Feb. 22, 2022: addresses COVID-19 spike-ACE2 binding assay for drug and antibody screening.

U.S. Pat. No. 11,116,818. Choe, et al., Sep. 14, 2021: addresses compositions and methods for inhibiting viral entry.

U.S. Pat. No. 11,034,655. Vidhani, et al., Jun. 15, 2021: addresses compounds for inhibiting the activity of SARS-COV-2 spike glycoprotein by inhibiting the activity of receptor binding domain (RBD) of SARS-COV-2 in its "closed" conformation before it binds with the human ACE2 receptor.

U.S. Pat. No. 11,026,909. Raju, et al., Jun. 8, 2021: addresses therapy for viral infections including the novel corona virus (COVID-19). A method for amelioration of, or prophylaxis against, a viral infection comprising administering to a patient in need of treatment a therapeutically effective amount of 5-aminolevulinic acid, optionally with at least one of curcumin nano, zinc, vitamin C and methylene blue, and compositions thereof. Such compositions may be used for the treatment of coronavirus infections, including the SARS-CoV-2 virus, and/or rhinoviruses.

None of the patents discussed above disclose or suggest the use of nutraceutical compounds to block the Coronavirus spike proteins, Rhinovirus, and/or other virus spike proteins and/or mRNA vaccine spike proteins from attaching to the cell membrane ACE2 receptors to block penetration through the cell membrane and the resulting virus particle and mRNA vaccine spike protein replication inside the cell. Nor is there any teaching of any combination of nutraceuticals to transit zinc through cell membranes where the zinc can inhibit the replication of virus particles and mRNA vaccine spike proteins inside the cells, or even using combinations of nutraceuticals to inhibit excess cytokines known as the cytokine storm, thereby, reducing inflammation and the resulting long-term disease and health issues.

In addition, this disclosure claims that sulforaphane is not only anti-inflammatory but offers antiviral defenses through multiple mechanisms including but not limited to blocking Coronavirus spike proteins, Rhinovirus, and/or other virus spike proteins and mRNA vaccine spike proteins from attaching to the ACE2 cell receptors and thereby inhibiting the spike proteins from penetrating the cell membrane and replicating inside the cell.

Operation Warp Speed brought to market in the United States two mRNA vaccines, produced by Pfizer and Moderna. Interim data suggested high efficacy for both of these vaccines, which helped legitimize Emergency Use Authorization (EUA) by the FDA. However, the exceptionally rapid movement of these vaccines through controlled trials and into mass deployment raises multiple safety concerns. In this patent application, we first describe the technology underlying these vaccines in detail. We then review both components of and the intended biological response to these vaccines, including production of the spike protein itself, and their potential relationship to a wide range of both acute and long-term induced pathologies, such as blood disorders, neurodegenerative diseases, and autoimmune diseases. Among these potential induced pathologies, we discuss the relevance of prion-protein-related amino acid sequences within the spike protein. We also present a brief review of studies supporting the potential for spike protein "shedding", transmission of the protein from a vaccinated to an unvaccinated person, resulting in symptoms induced in the latter. We finish by addressing a common point of debate, namely, whether or not these vaccines could modify the DNA of those receiving the vaccination. While there are no studies demonstrating definitively that this is happening, we provide a plausible scenario, supported by previously established pathways for transformation and transport of genetic material, whereby injected mRNA could ultimately be incorporated into germ cell DNA for transgenerational transmission.

SUMMARY OF THE DISCLOSURE

The present teachings include a method of treating or preventing complications associated with a SARS-CoV-2 infection, Rhinovirus, and mRNA vaccines comprising administration of a combination of Nutraceutical compositions of various combinations of cannabinoids, vitamins, trace elements, bioactive components, bioflavonoid polyphenols, proteolytic enzymes, amino acids, and antioxidants with at least one combination of 3 or more of Glutathione, N-acetylcysteine, Alpha Lipoic Acid, Quercetin, Zinc, Vitamin D3, Vitamin K2, Vitamin B6, Vitamin B9, Vitamin B12, Magnesium, Bromelain, Cannabidiolic Acid, Cannabigerolic Acid, Cannabidiol, Cannabigerol, Cannabinol, *Nigella Sativa*/Thymoquinone, Selenium, Curcumin, Piperine, Astaxanthin, and Sulforaphane each present in therapeutically effective amounts, in an admixture with nutraceutically acceptable excipient.

According to various embodiments of the present teachings, the nutraceutical composition can comprise Cannabidiolic Acid, Cannabigerolic Acid, Cannabidiol, Cannabigerol, Vitamin D3, Vitamin K2, Magnesium, Quercetin, Zinc, Bromelain, *Nigella Sativa*/Thymoquinone, and Astaxanthin.

According to other embodiments of the present teachings, the nutraceuticals Cannabidiolic Acid, Cannabigerolic Acid, Vitamin D3, Quercetin, Bromelain, Zinc, and *Nigella Sativa*/Thymoquinone can act to block COVID spike proteins and mRNA vaccine spike proteins from attaching to the ACE2 receptors on body organ cells.

The nutraceuticals Quercetin, Bromelain, *Nigella Sativa*/Thymoquinone, and Zinc can work synergistically and/or independently to penetrate body organ cell membranes and block the replication of virus particles and mRNA spike protein replication.

Also taught herein is that the nutraceuticals Cannabigerol, Vitamin D3, Vitamin K2, Quercetin, Bromelain, Zinc, *Nigella Sativa*/Thymoquinone, and Astaxanthin can act to inhibit excess cytokines, and that the nutraceuticals Cannabidiol, Vitamin D3, Vitamin K2, Magnesium, Quercetin, Zinc, Bromelain, *Nigella Sativa*/Thymoquinone, and Astaxanthin can work synergistically and/or independently to inhibit excess inflammation.

The ability of the nutraceuticals Cannabidiolic Acid, Cannabigerolic Acid, Cannabidiol, Cannabigerol, Vitamin D3, Vitamin K2, Magnesium, Quercetin, Zinc, Bromelain, *Nigella Sativa*/Thymoquinone, and Astaxanthin to work synergistically and/or independently to treat long-term diseases caused by excess cytokines, the COVID virus, Rhinovirus, and/or mRNA vaccine spike protein replication inside the cells is also disclosed in the present application.

The nutraceuticals Quercetin, Bromelain, and *Nigella Sativa*/Thymoquinone can work synergistically to increase the bioavailability of Zinc assisting its penetration through cell membranes where the zinc can then block virus particle and mRNA spike protein replication. Those three same nutraceuticals can also act as anti-coagulants to prevent blood clots caused by the mRNA vaccines.

In the presently disclosed nutraceutical composition, Cannabidiolic Acid and Cannabigerolic Acid can be present as phospholipid vesicles consisting of one or more concentric lipid bilayers enclosing discrete aqueous spaces to prevent reactive interaction with the other ingredients and to increase bioavailability of the Cannabidiolic Acid and Cannabigerolic Acid.

In another embodiment of the present teachings, a nutraceutical composition comprising N-acetylcysteine, Vitamin D3, Vitamin K2, Vitamin B6, Vitamin B9, Vitamin B12, Magnesium, Glutathione, Alpha Lipoic Acid, Selenium, Zinc, and Astaxanthin is taught.

The nutraceuticals N-acetylcysteine, Vitamin D3, Vitamin B9, Glutathione, Alpha Lipoic Acid, and Zinc are understood to act to block COVID spike proteins and mRNA vaccine spike proteins from attaching to the ACE2 receptors on body organ cells.

The nutraceuticals Glutathione and Zinc can work synergistically to penetrate body organ cell membranes and block the replication of virus particles and mRNA spike protein replication. Additionally, the nutraceuticals Glutathione, Selenium, and Astaxanthin can act to inhibit excess cytokines.

Further taught is nutraceuticals N-acetylcysteine, Vitamin D3, Vitamin K2, Vitamin B6, Vitamin B12, Magnesium, Glutathione, Alpha Lipoic Acid, Selenium, Zinc, and Astaxanthin as working synergistically and/or independently to inhibit excess inflammation. Also disclosed by the present application is treatment of long-term diseases caused by the COVID virus, Rhinoviruses, and/or mRNA vaccine spike protein replication inside the cells by the synergistic and/or independent work of the nutraceuticals N-acetylcysteine, Vitamin D3, Vitamin K2, Vitamin B6, Vitamin B9, Vitamin B12, Magnesium, Glutathione, Alpha Lipoic Acid, Selenium, Zinc, and Astaxanthin.

The nutraceutical Glutathione can act as both a zinc ionophore to increase the bioavailability of zinc assisting its penetration through cell membranes where the Zinc can block virus particle and mRNA spike protein replication, and as an anti-coagulant to prevent blood clots caused by the mRNA vaccines.

The human immune system can also be optimized the synergist work of the nutraceuticals Glutathione, Vitamin D3, Vitamin K2, and Magnesium.

Another nutraceutical composition disclosed by the present disclosure is a composition comprising Vitamin D3, Vitamin K2, Quercetin, Bromelain, *Nigella Sativa*/Thymoquinone, Magnesium, Sulforaphane, N-acetylcysteine, Glutathione, Zinc, Piperine, Curcumin, and Astaxanthin.

In the presently disclosed nutraceutical composition containing nutraceuticals Vitamin D3, Quercetin, Bromelain, *Nigella Sativa*/Thymoquinone, N-acetylcysteine, Glutathione, Zinc, and Curcumin these components can act to block COVID spike proteins and mRNA vaccine spike proteins from attaching to the ACE2 receptors on body organ cells.

The capability of the nutraceutical combination of Quercetin, *Nigella Sativa*/Thymoquinone, Glutathione, Bromelain, Curcumin, and Zinc to work synergistically and/or independently to increase the bioavailability of Zinc by assisting its penetration through cell membranes where the Zinc can block virus particle and mRNA spike protein replication is also taught by the present teachings.

The composition of nutraceuticals Vitamin D3, Vitamin K2, Quercetin, Bromelain, *Nigella Sativa*/Thymoquinone, Sulforaphane, N-acetylcysteine, Glutathione, Zinc, Curcumin, and Astaxanthin can both act to inhibit excess cytokines, and also to work synergistically and/or independently to inhibit excess inflammation is also disclosed.

Also presently disclosed is the nutraceutical composition of Quercetin, Bromelain, *Nigella Sativa*/Thymoquinone, Curcumin, and Zinc which work synergistically and/or independently to treat long-term diseases caused by the COVID virus, Rhinovirus, and/or mRNA vaccine spike protein replication inside the cells.

Yet another embodiment of the present teaching is the nutraceutical composition of Quercetin, *Nigella Sativa*/Thymoquinone, Bromelain, Astaxanthin, and Curcumin which act as anti-coagulants to prevent blood clots caused by the mRNA vaccines.

In some instances of embodiments of the present teachings, the nutraceutical composition can comprise one or more of Glutathione, N-acetylcysteine, Alpha Lipoic Acid, Quercetin, Zinc, Vitamin D3, Vitamin K2, Vitamin B6, Vitamin B9, Vitamin B12, Magnesium, Bromelain, Cannabidiolic Acid, Cannabigerolic Acid, Cannabidiol, Cannabigerol, Cannabinol, *Nigella Sativa*/Thymoquinone, Selenium, Curcumin, Piperine, Astaxanthin, and/or Sulforaphane.

For the presently disclosed nutraceutical compositions, the therapeutic dose (or therapeutic effective amount) for each of the named nutraceuticals can be provided in a single or divided doses of twice daily or thrice daily. In those nutraceutical compositions, it is presently disclosed that the therapeutic dose for each of the components is tabulated below:

| Nutraceutical | Lower Range | Upper Range |
| --- | --- | --- |
| Glutathione | 250 mg | 1000 mg |
| N-acetylcysteine | 300 mg | 900 mg |
| Alpha Lipoic Acid | 100 mg | 600 mg |
| Quercetin | 125 mg | 500 mg |
| Zinc | 15 mg | 50 mg |
| Vitamin D3 | 100 mcg | 200 mcg |
| Vitamin K2 | 100 mcg | 200 mcg |
| Vitamin B6 | 5 mg | 15 mg |
| Vitamin B9 | 300 mcg | 500 mcg |
| Vitamin B12 | 1 mg | 3 mg |
| Magnesium | 30 mg | 200 mg |
| Bromelain | 25 mg | 250 mg |
| Cannabidiolic Acid | 5 mg | 60 mg |
| Cannabigerolic Acid | 5 mg | 60 mg |
| Cannabidiol | 5 mg | 60 mg |
| Cannabigerol | 5 mg | 60 mg |
| Cannabinol | 2 mg | 10 mg |
| Nigella Sativa/Thymoquinone | 100 mg | 1000 mg |
| Selenium | 100 mcg | 200 mcg |
| Curcumin | 500 mg | 1500 mg |
| Piperine | 5 mg | 15 mg |
| Astaxanthin | 4 mg | 12 mg |
| Sulforaphane | 400 mcg | 25 mg |

For each of the above listed nutraceutical component the therapeutic dose can also be any range with endpoints defined by any value within any two of the listed values.

The nutraceuticals and the various cannabinoids, vitamins, trace elements, bioactive components, bioflavonoid polyphenols, proteolytic enzymes, amino acids, and antioxidants utilized in the various composition of the presently taught disclosure can be incorporated or available in the compositions in any and all known and unknown forms of ingredients including but not limited to liquid, oil, water soluble, powder, liposomal, nano and/or any other form suitable for nutraceuticals and/or supplements. Furthermore, these nutraceutical compositions presently disclosed may be in any and all known and unknown forms of delivery systems including but not limited to tablets, capsules, soft gels, gel caps, powders, bars, gummies, and liquids. All of the nutraceutical compositions disclosed herein can be presented in an oral dosage form.

Various relationships between different components of the presently disclosed nutraceutical compositions are outlined below. The regulation and function of Glutathione is dependent on cellular conditions and the physiological concentration of vitamin D. Also, Vitamin D3 can be an immuno-regulating hormone which requires adequate levels of Vitamin K2 to be taken safely, and all enzymes that metabolize Vitamin D3 require Magnesium. Furthermore, Quercetin has been shown to act as a Zinc ionophore enhancing the entrance of Zinc into cells where the Zinc can inhibit viral intracellular replication.

More relationships include Bromelain substantially promoting the absorption of Curcumin and Quercetin enhancing their bioavailability. The presence of Piperine increases the bioavailability of Curcumin thereby increasing its efficacy, and the presence of Bromelain substantially increases the bioavailability of Curcumin thereby increasing its efficacy.

In those nutraceutical compositions where the systemic bioavailability of orally consumed glutathione is poor, N-acetylcysteine (NAC) as a precursor to Glutathione can be present to increase concentrations and efficacy.

*Nigella Sativa*/Thymoquinone can act as an ionophore for enhanced uptake of Zinc which in turn can enhance host immune response against SARS-CoV-2 as well as inhibit its replication.

In some embodiments of the presently disclosed nutraceutical composition, Zinc modulates the total cellular Glutathione concentration thereby improving Glutathione efficacy. In other embodiments of the presently disclosed nutraceutical composition, Selenium selenoprotein enzyme was found to enhance the activity and expression of Glutathione peroxidase in the endothelial cell, thereby protecting the endothelial cells from oxidative damage.

In embodiments of the presently disclosed nutraceutical composition with both Glutathione and Astaxanthin present, these components work synergistically and collectively to form a barrier against pathogens.

DETAILED DESCRIPTION

The present teachings are directed to various combinations of cannabinoids, vitamins, trace elements, bioactive components, bioflavonoid polyphenols, proteolytic enzymes, amino acids, and antioxidants that work independently and synergistically for the prevention, treatment, and inhibition of excess cytokines caused by the immune response to extreme viral and bacterial infections, the inhibition of COVID-19, Rhinovirus and/or other virus spike proteins and mRNA vaccine spike proteins from attaching to body organ cells, penetrating cell membranes, and the replication of virus particles and spike proteins inside the cells.

In addition, these unique combinations of compounds inhibit inflammation and prevent long-term side effects (long COVID, health issues, long-haulers), and disease caused by the SARS-CoV-2 and its variants, Rhinovirus, other viruses, bacteria, and mRNA vaccines caused by damage done to body organ cell tissue.

Furthermore, certain of these antioxidants can cross the blood-brain barrier to inhibit cytokine, viral spike protein, and mRNA vaccine spike protein damage done to cells in the brain and the central nervous system. Multiple combinations of these compounds work synergistically to increase the efficacy of independent nutraceuticals targeting the inhibition of excess cytokines, COVID spike proteins, mRNA vaccine spike proteins, and inflammation.

Moreover, each individual's immune system is unique, and this disclosure uses multiple nutraceuticals and formulations to cover the broadest possible range of effective inhibition excess cytokines, COVID spike proteins and mRNA spike proteins from attaching to human body organ cells, penetrating cell membranes, and replicating inside the cells. Prevention and treatment require inhibiting excess cytokines, and blocking cell attachment, penetration, and replication by SARS-CoV-2 spike proteins and its variants, and/or mRNA spike proteins.

Nutraceuticals include dietary supplements. The term "dietary supplement" refers to a wide range of products including vitamins and minerals, herbs and other botanicals, amino acids, enzymes, and more.

SARS-CoV-2 is a member of the class of positive-strand RNA viruses, which means that they code directly for the proteins that the RNA encodes, rather than requiring a copy to an antisense strand prior to translation into protein. The virus consists primarily of the single-strand RNA molecule packaged up inside a protein coat, consisting of the virus's structural proteins, most notably the spike protein, which facilitates both viral binding to a receptor (in the case of SARS-CoV-2 this is the ACE2 receptor) and virus fusion with the host cell membrane. The SARS-CoV-2 spike protein is the primary target for neutralizing antibodies.

Experimental mRNA vaccines have been heralded as having the potential for great benefits, but they also harbor the possibility of potentially tragic and even catastrophic unforeseen consequences. The mRNA vaccines against SARS-CoV-2 have been implemented with great fanfare, but there are many aspects of their widespread utilization that merit concern. We want to emphasize that these concerns are potentially serious and might not be evident for years or even transgenerationally.

Furthermore, as an obvious but tragically ignored suggestion, the government should also be encouraging the population to take safe and affordable steps to boost their immune systems naturally, such as getting out in the sunlight to raise vitamin D levels (Ali, 2020), and eating mainly organic whole foods rather than chemical-laden processed foods (Rico-Campà et al., 2019). Also, eating foods that are good sources of vitamin A, vitamin C and vitamin K2 should be encouraged, as deficiencies in these vitamins are linked to bad outcomes from COVID-19 (Goddek, 2020; Sarohan, 2020). (Seneff, 2021).

This comprehensive presentation of the damage being done by SARS-CoV-2 spike proteins and mRNA vaccine spike proteins encompasses most severe health issues being caused by them and indicates how imperative it is to find methods of defense against the effects from exposure to SARS-CoV-2 spike proteins and mRNA vaccine spike proteins. Furthermore, the mRNA vaccine instructs the immune system to continuously produce spike proteins and current research indicates that can be anywhere from 4-8 weeks and up to a year. With the advent of continuous booster shots, this is a problem that needs to be solved.

The critical point at which the process of infecting cells that allow virus particle and spike protein replication begins when the SARS-CoV-2 spike proteins and mRNA vaccine spike proteins attach themselves to the ACE2 receptors on body organ cells. The key to preventing severe disease and potential death from exposure to the SARS-CoV-2 spike proteins and mRNA vaccine spike proteins is to block spike protein cell attachment, penetration, and replication.

This disclosure proposes the use of nutraceuticals to inhibit the SARS-CoV-2 spike proteins and mRNA vaccine spike proteins from attaching to the ACE2 receptors of body organ cells such as the brain, kidney, liver, heart, lungs, and other body organ cells. Blocking the SARS-CoV-2 spike proteins and mRNA vaccine spike proteins from attaching to the ACE2 receptors interrupts the pathogenesis of SARS-CoV-2 spike proteins and blocks entry of mRNA vaccine spike proteins into the cells where they replicate, damage the mitochondria, and cause hyperinflammation leading to long-term disease.

This disclosure inhibits excess cytokines, blocks COVID spike proteins and excess mRNA vaccine spike proteins from attaching to cells keeping them from penetrating cell membranes and the resulting replication inside the cells. This disclosure also has synergistic combinations of nutraceuticals that can penetrate cell membranes and block replication of virus particles and mRNA vaccine spike proteins that do get inside the cells. Blocking cell attachment, penetration, and replication reduces inflammation and long-term side effects and disease.

COVID-19 Pathogenesis

The microscopic coronavirus enters through the nose or mouth, where it begins its infection of our airways. The outer spike protein of the coronavirus latches onto specific receptors on the surface of cells. In the case of COVID-19, the virus latches on to the ACE2 receptor. This binding triggers the process by which the virus fuses into human cells. The viral envelope merges with the oily membrane of our own cells, allowing the virus to release its genetic material into the inside of the healthy cell. The genetic blueprint of the virus is RNA (instead of DNA), which acts as a molecular message, instructing our host cell machinery to read the template and translate it into proteins that make up new virus particles. SARS-CoV-2, Spike (S) Protein binds to host cells by recognizing human angiotensin-converting enzyme 2 (hACE2) receptor. The viral Spike Protein contains S1 and S2 domains that constitute the binding and fusion machinery, respectively. Structural analysis of viral Spike Protein reveals that the virus undergoes conformational flexibility and dynamicity to interact with the hACE2 receptor. (Gupta, 2021).

Reviewed literature does not discuss a way for nutraceuticals to penetrate the cell membrane and inhibit virus particle and mRNA spike protein replication inside the cell. Reviewed literature presents a limited number of nutraceuticals that may block SARS-CoV-2, Spike (S) Protein and mRNA vaccine spike proteins from attaching to the ACE2 receptors when used in combination with 5 aminolevulinic acid.

This disclosure encompasses multiple combinations of nutraceuticals that act alone and synergistically to block SARS-CoV-2 spike protein and mRNA vaccine spike proteins from attaching to the ACE2 receptors and does not include 5 aminolevulinic acid in any of the formulations.

Excess Cytokines

Cytokine Storm and cytokine release syndrome are life-threatening systemic inflammatory syndromes involving elevated levels of circulating cytokines and immune cell hyperactivation that can be triggered by various therapies, pathogens, cancers, autoimmune conditions, and monogenic disorders. Inflammation involves a set of biologic mechanisms that evolved in multicellular organisms to contain invasive pathogens and resolve injuries by activating innate and adaptive immune responses. The immune system is expected to recognize foreign invaders, respond proportionally to the pathogen burden, and then return to homeostasis. This response requires a balance between sufficient cytokine production to eliminate the pathogen and avoidance of a hyperinflammatory response in which an overabundance of cytokines causes clinically significant collateral damage. At increased levels, cytokines can have systemic effects and cause collateral damage to vital organ systems. (Fajgenbaum, 2020).

Reviewed literature has not addressed this issue effectively nor offered a solution for maintaining cytokines in their normal range returning them to homeostasis after an immune response and elevated levels of cytokines.

This disclosure includes nutraceuticals that work independently and synergistically to inhibit excess cytokines and keep them in their normal range limiting damage to body cell tissue and inhibiting inflammation.

SARS-CoV-2 Spike Protein: The human body is made up of approximately 3 trillion body cells. The outer spike protein of the coronavirus latches onto specific receptors on the surface of body cells. In the case of COVID-19, the virus latches on to the ACE2 receptor. This binding triggers the process by which the virus fuses into human cells. The viral envelope merges with the oily membrane of our own cells, allowing the virus to release its genetic material into the inside of the healthy cell. Once inside the cell the virus particles start to replicate causing a more severe infection and potential death (Scudellari, 2021).

Reviewed literature does not disclose any method by which nutraceuticals block the SARS-CoV-2 spike proteins from attaching to the ACE2 receptors, does not disclose any method by which nutraceuticals block penetration of cell membranes, and does not disclose any method by which nutraceuticals can penetrate cell membranes and block replication inside the cell.

This disclosure includes nutraceuticals that work independently and synergistically to inhibit the Coronavirus, Rhinovirus and/or other virus spike proteins and mRNA vaccine spike proteins from attaching to the cells receptors thereby preventing most virus particles from getting inside the cell to replicate.

In addition, this disclosure includes nutraceuticals that work independently and synergistically to penetrate body cell membranes and inhibit virus particle replication thereby reducing the potential for severe infection and potential death.

mRNA Vaccine Spike Protein

The mRNA vaccine injects a genetic code into your system. This code tells your body to produce the spike proteins. As the COVID injection recodes messenger RNA to permanently and persistently replicate spike proteins, the immune system is forced to constantly fend off the malignant substance. The ongoing battle ultimately depletes natural immunity (Immanuel, 2022). These excess spike proteins attach themselves to the ACE2 receptors on body organ cells, penetrate the cell membrane and replicate inside the cells.

Reviewed literature does not disclose any method by which nutraceuticals block the mRNA vaccine spike proteins from attaching to the ACE2 receptors, does not disclose any method by which nutraceuticals block penetration of cell membranes, and does not disclose any method by which nutraceuticals can penetrate cell membranes and block replication inside the cell.

This disclosure includes nutraceuticals that work independently and synergistically to inhibit excess mRNA vaccine spike proteins from attaching to cell receptors thereby preventing most excess spike proteins from getting inside the cell to replicate which would cause damage to the mitochondria.

In addition, this disclosure includes nutraceuticals that work independently and synergistically to penetrate body cell membranes and inhibit mRNA vaccine spike protein replication thereby reducing the potential for mitochondria damage, hyperinflammation, long-term side effects, and long-term health issues.

Inflammation and Long-Term Side Effects: Inflammation is a key feature of COVID-19 and mRNA vaccine reactions. When inflammation is overwhelming, it may lead to unfavorable outcomes or even death. A recent systematic review and meta-analysis shows that 30-80% of individuals with a confirmed COVID-19 diagnosis or have had one shot or more of an mRNA vaccine continue to have at least one overall effect beyond two weeks following acute infection or vaccination. These long-term side effects are caused by excess inflammation or hyperinflammation (Wong, 2021).

Reviewed literature does not disclose a method by which nutraceuticals can block the pathogenesis of the SARS-CoV-2 spike protein which can result in severe damage to body organ cell tissue and to cell mitochondria resulting in hyperinflammation and long-term side effects and disease.

This disclosure includes nutraceuticals that work independently and synergistically to inhibit excess inflammation or hyperinflammation thereby significantly reducing the possibility of long-term side effects and health issues.

Central Nervous System: Cytokines, SARS-CoV-2 spike proteins and mRNA vaccine spike proteins can all cross the blood-brain barrier and penetrate brain cell tissue and central nervous system cell tissues. There has been an increase of over 1000% in neurological disorders since the COVID pandemic and mRNA vaccines have been in use. Excess cytokines, Coronavirus spike proteins, and mRNA vaccine spike proteins create toxins in brain cells and the central nervous system cells that cause damage and potential health issues such as Dementia and Alzheimer's.

Reviewed literature does not disclose a method by which nutraceuticals can cross the blood brain barrier to eradicate toxins resulting from SARS-CoV-2 spike protein and mRNA vaccine spike protein replication in the brain and central nervous system.

This disclosure includes antioxidant nutraceuticals that can cross the blood-brain barrier and inhibit the potential damage that results from the cytokines, viral spike proteins, and mRNA vaccine spike proteins that have crossed the blood-brain barrier. (Gleb, 2017), (Richards, 2019), (Ordonez, et al., 2022).

SARS-CoV-2 Spike Proteins

SARS-CoV-2, which shares 79% sequence similarity with SARS-CoV, belongs to the genus Sarbecovirus [6]. This virus encodes a set of structural proteins (membrane protein, nucleocapsid protein, envelope protein and spike glycoprotein), non-structural proteins (of which most compose the viral replication and transcription complex) and accessory proteins. The structural proteins—together with a lipid bilayer derived from the host—form an enveloped virion (or virus particle) that delivers viral genomic RNA into the cell. The accessory proteins are dispensable for replication but often have immunoevasive activities [7,8,9]. The main determinant of coronavirus tropism is the spike glycoprotein, which forms trimers on the surface of virions [10]. The spike protein consists of two subunits: the S1 subunit, which binds to the host entry receptor angiotensin-converting enzyme 2 (ACE2) [11], and the S2 subunit, which mediates membrane fusion. These two subunits are separated by the S1-S2 site, which contains a furin cleavage motif and is cleaved in the virus-producing cell. After binding to ACE2 on the target cell, the spike protein is cleaved by the transmembrane serine protease TMPRSS2 at the S2' site [12,13,14]. This cleavage activates the S2 subunit trimers to fuse viral and host lipid bilayers, releasing the viral ribonucleoprotein complex into the cell. Another entry route that may be used by the virus is the endosome, in which cathepsins can cleave the spike protein, but this route is not efficiently used in primary epithelial cells [14,15,16,17]. (Lamers, 2022).

mRNA Vaccine Spike Proteins

Antibody-Dependent Enhancement (ADE)

Antibody-Dependent Enhancement (ADE) is believed to underlie the more severe dengue fever often observed in those with previous exposure (Beltramello et al., 2010), and might also play a role in more severe disease among those previously vaccinated against the disease (Shukla et al., 2020).

A theory for how ADE might occur in the case of a SARS-CoV-2 vaccine suggests that non-neutralizing antibodies form immune complexes with viral antigens to provoke excessive secretion of pro-inflammatory cytokines, and in the extreme case, a cytokine storm causing widespread local tissue damage (Lee et al., 2020).

With tens of millions of young adults and even children now with vaccine-induced coronavirus spike protein antibodies, there exists the possibility of triggering ADE related to either future SARS-CoV-2 infection or booster injection among this younger population. The mRNA vaccines ultimately deliver the highly antigenic spike protein to antigen-presenting cells. As such, monoclonal antibodies against the spike protein are the expected outcome of the currently deployed mRNA vaccines. Human spike protein monoclonal antibodies were found to produce high levels of cross-reactive antibodies against endogenous human proteins (Vojdani et. al., 2021). Given evidence only partially studied here, there is sufficient reason to suspect that antibodies to the spike protein will contribute to ADE provoked by prior SARS-CoV-2 infection or vaccination, which may manifest as either acute or chronic autoimmune and inflammatory conditions.

Adaptive Immune System

A functional analysis of the endogenous human proteins homologous with viral proteins found that over ⅓ of them are associated with the adaptive immune system. There is speculation that prior virus exposure or prior vaccination, either of which could initiate antibody production that targets these endogenous proteins, may be playing a role in the development of more severe disease in the elderly in particular. In this case the pre-existing antibodies act to suppress the adaptive immune system and lead to more severe disease.

Autoimmunity

Autoimmunity is becoming much more widely recognized as a sequela of COVID-19. There are multiple reports of previously healthy individuals who developed diseases such as idiopathic thrombocytopenic purpura, Guillain-Barré syndrome and autoimmune haemolytic anaemia (Galeotti and Bayry, 2020).

Autoantibodies

Autoantibodies are very commonly found in COVID-19 patients, including antibodies found in blood (Vlachoyiannopoulos et. al., 2020) and cerebrospinal fluid (CFS) (Franke et. al., 2021). Though SARS-CoV-2 is not found in the CSF, it is theorized that the autoantibodies created in response to SARS-CoV-2 exposure may lead to at least some portion of the neurological complications documented in COVID-19 patients.

(Zuo et. al., 2020) found anti-phospholipid autoantibodies in 52% of hospitalized COVID-19 patients and speculated that these antibodies contribute to the high incidence of coagulopathies in these patients.

They conclude, "One of the potential side effects of giving a mass vaccine could be an mergence [sic] of autoimmune diseases especially in individuals who are genetically prone for autoimmunity."

We have reviewed the evidence here that the spike protein of SARS-CoV-2 has extensive sequence homology with multiple endogenous human proteins and could prime the immune system toward development of both auto-inflammatory and autoimmune disease. This is particularly concerning given that the protein has been redesigned with two extra proline residues to potentially impede its clearance from the circulation through membrane fusion. These diseases could present acutely and over relatively short timespans such as with MIS-C or could potentially not manifest for months or years following exposure to the spike protein, whether via natural infection or via vaccination.

Many who test positive for COVID-19 express no symptoms. The number of asymptomatic, PCR-positive cases varies widely between studies, from a low of 1.6% to a high of 56.5% (Gao et. al., 2020). Those who are insensitive to COVID-19 probably have a very strong innate immune system. The healthy mucosal barrier's neutrophils and macrophages rapidly clear the viruses, often without the need for any antibodies to be produced by the adaptive system. However, the vaccine intentionally completely bypasses the mucosal immune system, both through its injection past the natural mucosal barriers and its artificial configuration as an RNA-containing nanoparticle. As noted in (Carsetti, 2020), those with a strong innate immune response almost universally experience either asymptomatic infection or only mild COVID-19 disease presentation. Nevertheless, they might face chronic autoimmune disease, as described previously, as a consequence of excessive antibody production in response to the vaccine, which was not necessary in the first place.

Spike Protein Toxicity

The picture is now emerging that SARS-CoV-2 has serious effects on the vasculature in multiple organs, including the brain vasculature. As mentioned earlier, the spike protein facilitates entry of the virus into a host cell by binding to ACE2 in the plasma membrane. ACE2 is a type I integral membrane protein that cleaves angiotensin II into angiotensin (1-7), thus clearing angiotensin II and lowering blood pressure. In a series of papers, Yuichiro Suzuki in collaboration with other authors presented a strong argument that the spike protein by itself can cause a signaling response in the vasculature with potentially widespread consequences (Suzuki, 2020; Suzuki et al., 2020; Suzuki et al., 2021; Suzuki and Gychka, 2021). These authors observed that, in severe cases of COVID-19, SARSCoV-2 causes significant morphological changes to the pulmonary vasculature. Post-mortem analysis of the lungs of patients who died from COVID-19 revealed histological features showing vascular wall thickening, mainly due to hypertrophy of the tunica media. Enlarged smooth muscle cells had become rounded, with swollen nuclei and cytoplasmic vacuoles (Suzuki et al., 2020). Furthermore, they showed that exposure of cultured human pulmonary artery smooth muscle cells to the SARSCoV-2 spike protein 51 subunit was sufficient to promote cell signaling without the rest of the virus components.

Follow-on papers (Suzuki et al., 2021, Suzuki and Gychka, 2021) showed that the spike protein 51 subunit suppresses ACE2, causing a condition resembling pulmonary arterial hypertension (PAH), a severe lung disease with very high mortality. Ominously, Suzuki and Gychka (2021) wrote: "Thus, these in vivo studies demonstrated that the spike protein of SARS-CoV-1 (without the rest of the virus) reduces the ACE2 expression, increases the level of angiotensin II, and exacerbates the lung injury." The "in vivo studies" they referred to here (Kuba et al., 2005) had shown that SARS coronavirus-induced lung injury was primarily due to inhibition of ACE2 by the SARS-CoV spike protein, causing a large increase in angiotensin-II. Suzuki et al. (2021) went on to demonstrate experimentally that the 51 component of the SARS-CoV-2 virus, at a low concentration of 130 pM, activated the MEK/ERK/MAPK signaling pathway to promote cell growth. They speculated that these effects would not be restricted to the lung vasculature. The signaling cascade triggered in the heart vasculature would cause coronary artery disease, and activation in the brain could lead to stroke. Systemic hypertension would also be predicted. They hypothesized that this ability of the spike protein to promote pulmonary arterial hypertension could predispose patients who recover from SARS-CoV-2 to later develop right ventricular heart failure. Furthermore, they suggested that a similar effect could happen in response to the mRNA vaccines, and they warned of potential long-term consequences to both children and adults who received COVID-19 vaccines based on the spike protein (Suzuki and Gychka, 2021).

An interesting study by Lei et. al. (2021) found that pseudovirus—spheres decorated with the SARS-CoV-2 S1 protein but lacking any viral DNA in their core—caused inflammation and damage in both the arteries and lungs of mice exposed intratracheally. They then exposed healthy human endothelial cells to the same pseudovirus particles. Binding of these particles to endothelial ACE2 receptors led to mitochondrial damage and fragmentation in those endothelial cells, leading to the characteristic pathological changes in the associated tissue. This study makes it clear that spike protein alone, unassociated with the rest of the viral genome, is sufficient to cause the endothelial damage associated with COVID-19. The implications for vaccines intended to cause cells to manufacture the spike protein are clear and are an obvious cause for concern. Neurological symptoms associated with COVID-19, such as headache, nausea and dizziness, encephalitis and fatal brain blood clots are all indicators of damaging viral effects on the brain.

Buzhdygan et al. (2020) proposed that primary human brain microvascular endothelial cells could cause these symptoms. ACE2 is ubiquitously expressed in the endothelial cells in the brain capillaries. ACE2 expression is upregulated in the brain vasculature in association with dementia and hypertension, both of which are risk factors for bad outcomes from COVID-19. In an in vitro study of the blood-brain barrier, the S1 component of the spike protein promoted loss of barrier integrity, suggesting that the spike protein acting alone triggers a pro-inflammatory response in brain endothelial cells, which could explain the neurological consequences of the disease (Buzhdygan et al., 2020). The implications of this observation are disturbing because the mRNA vaccines induce synthesis of the spike protein, which could theoretically act in a similar way to harm the brain.

The spike protein generated endogenously by the vaccine could also negatively impact the male testes, as the ACE2 receptor is highly expressed in Leydig cells in the testes (Verma et al., 2020).

Several studies have now shown that the coronavirus spike protein is able to gain access to cells in the testes via the ACE2 receptor, and disrupt male reproduction (Navarra et al., 2020; Wang and Xu, 2020). A paper involving postmortem examination of testicles of six male COVID-19 patients found microscopic evidence of spike protein in interstitial cells in the testes of patients with damaged testicles (Achua et al., 2021).

A Possible Link to Prion Diseases and Neurodegeneration

Prion diseases are a collection of neurodegenerative diseases that are induced through the misfolding of important bodily proteins, which form toxic oligomers that eventually precipitate out as fibrils causing widespread damage to neurons. Stanley Prusiner first coined the name 'prion' to describe these misfolded proteins (Prusiner, 1982).

It is now believed that many neurodegenerative diseases, including Alzheimer's, Parkinson's disease, and amyotrophic lateral sclerosis (ALS) may be prion diseases, and researchers have identified specific proteinaceous infectious particles linked to these diseases (Weickenmeier et al., 2019). When considering that the SARS-CoV-2 spike protein is a transmembrane protein, and that it contains five GxxxG motifs in its sequence (see uniprot.org/uniprot/P0DTC2), it becomes extremely plausible that it could behave as a prion. One of the GxxxG sequences is present within its membrane fusion domain. Recall that the mRNA vaccines are designed with an altered sequence that replaces two adjacent amino acids in the fusion domain with a pair of prolines. This is done intentionally in order to force the protein to remain in its open state and make it harder for it to fuse with the membrane. This seems to us like a dangerous step towards misfolding potentially leading to prion disease.

A paper published by J. Bart Classen (2021) proposed that the spike protein in the mRNA vaccines could cause prion-like diseases, in part through its ability to bind to many known proteins and induce their misfolding into potential prions. Idrees and Kumar (2021) have proposed that the spike protein's S1 component is prone to act as a functional amyloid and form toxic aggregates. These authors wrote that S1 has the ability "to form amyloid and toxic aggregates that can act as seeds to aggregate many of the misfolded brain proteins and can ultimately lead to neurodegeneration."

Vaccine Shedding

There has been considerable chatter on the Internet about the possibility of vaccinated people causing disease in unvaccinated people in close proximity. While this may seem hard to believe, there is a plausible process by which it could occur through the release of exosomes from dendritic cells in the spleen containing misfolded spike proteins, in complex with other prion reconformed proteins. These exosomes can travel to distant places. It is not impossible to imagine that they are being released from the lungs and inhaled by a nearby person. Extracellular vesicles, including exosomes, have been detected in sputum, mucus, epithelial lining fluid, and bronchoalveolar lavage fluid in association with respiratory diseases (Lucchetti et al., 2021).

Cytokines

Cytokine storm and cytokine release syndrome are life-threatening systemic inflammatory syndromes involving elevated levels of circulating cytokines and immune cell hyperactivation that can be triggered by various therapies, pathogens, cancers, autoimmune conditions, and monogenic disorders.

Inflammation involves a set of biologic mechanisms that evolved in multicellular organisms to contain invasive pathogens and resolve injuries by activating innate and adaptive immune responses. The immune system is expected to recognize foreign invaders, respond proportionally to the pathogen burden, and then return to homeostasis. This response requires a balance between sufficient cytokine production to eliminate the pathogen and avoidance of a hyperinflammatory response in which an overabundance of cytokines causes clinically significant collateral damage. Cytokines play a key role in coordinating antimicrobial effector cells and providing regulatory signals that direct, amplify, and resolve the immune response. Cytokines have short half-lives, which normally prevents them from having effects outside lymphoid tissue and sites of inflammation. Although typically considered to be pathologic, sustained production of cytokines that leads to elevated circulating levels may be necessary to appropriately control some disseminated infections. At increased levels, cytokines can have systemic effects and cause collateral damage to vital organ systems.

Covid-19, which is caused by SARS-CoV-2, is characterized by heterogeneous symptoms ranging from mild fatigue to life-threatening pneumonia, cytokine storm, and multiorgan failure. Cytokine storm was also reported in patients with SARS and was associated with poor outcomes. [86] Although the mechanisms of lung injury and multiorgan failure in Covid-19 are still under investigation, [14] reports of hemophagocytosis and elevated cytokine levels—as well as beneficial effects of immunosuppressant agents—in affected patients, particularly those who are the most severely ill, suggest that cytokine storm may contribute to the pathogenesis of Covid-19. [87,88]

Serum cytokine levels that are elevated in patients with Covid-19 associated cytokine storm include interleukin-1β, interleukin-6, IP-10, TNF, interferon-γ, macrophage inflammatory protein (MIP) 1α and 1β, and VEGF. [89,90] Higher interleukin-6 levels are strongly associated with shorter survival. [91]

Laboratory test results reflecting hyperinflammation and tissue damage were found to predict worsening outcomes in Covid-19. [93]

Although immunologic dysregulation has been observed in severe cases of Covid-19, [26] it is not known whether immune hyperactivity or a failure to resolve the inflammatory response because of ongoing viral replication or immune dysregulation underlies severe cases.

Fourth, clotting issues can occur across cytokine storm disorders, but thromboembolic events appear to be more frequent in Covid-19-associated cytokine storm. [99]. (Fajgenbaum, 2020).

Inflammation

One of the most important medical discoveries of the past two decades has been that the immune system and inflammatory processes are involved in not just a few select disorders, but a wide variety of mental and physical health problems that dominate present-day morbidity and mortality worldwide [1-4]. Indeed, chronic inflammatory diseases have been recognized as the most significant cause of death in the world today, with more than 50% of all deaths being attributable to inflammation-related diseases such as ischemic heart disease, stroke, cancer, diabetes mellitus, chronic kidney disease, non-alcoholic fatty liver disease (NAFLD) and autoimmune and neurodegenerative conditions [5]. Evidence is emerging that the risk of developing chronic inflammation can be traced back to early development, and its effects are now known to persist throughout the life span to affect adulthood health and risk of mortality [6-8].

Shifts in the inflammatory response from short- to long-lived can cause a breakdown of immune tolerance [9,15] and lead to major alterations in all tissues and organs, as well as normal cellular physiology, which can increase the risk for various non-communicable diseases in both young and older individuals [1,9-11,15,17-21]. SCI can also impair normal immune function, leading to increased susceptibility to infections and tumors and a poor response to vaccines [22-25]. Furthermore, SCI during pregnancy and childhood can have serious developmental consequences that include elevating the risk of non-communicable diseases over the life span [7,8,26,27].

The clinical consequences of SCI-driven damage can be severe and include increased risk of the metabolic syndrome, which includes the triad of hypertension, hyperglycemia and dyslipidemia [33,34]; type 2 diabetes [33]; NAFLD [33,35]; hypertension [1]; cardiovascular disease (CVD) [18,19]; chronic kidney disease [19]; various types of cancer [17]; depression [21]; neurodegenerative and autoimmune diseases [4,12,20]; osteoporosis [11,36] and sarcopenia [19]. (Furman, 2019).

Long COVID

SARS-CoV-2 infects cells via its spike protein binding to its surface receptor on target cells and results in acute symptoms involving especially the lungs known as COVID-19. However, increasing evidence indicates that many patients develop a chronic condition characterized by fatigue and neuropsychiatric symptoms, termed long-COVID. Most of the vaccines produced so far for COVID-19 direct mammalian cells via either mRNA or an adenovirus vector to express the spike protein, or administer recombinant spike protein, which is recognized by the immune system leading to the production of neutralizing antibodies. Recent publications provide new findings that may help decipher the pathogenesis of long-COVID. One paper reported perivascular inflammation in brains of deceased patients with COVID-19, while others showed that the spike protein could damage the endothelium in an animal model, that it could disrupt an in vitro model of the blood-brain barrier (BBB), and that it can cross the BBB resulting in perivascular inflammation. Moreover, the spike protein appears to share antigenic epitopes with human molecular chaperons resulting in autoimmunity and can activate toll-like receptors (TLRs), leading to release of inflammatory cytokines. Moreover, some antibodies produced against the spike protein may not be neutralizing but may change its conformation rendering it more likely to bind to its receptor. As a result, one wonders whether the spike protein entering the brain or being expressed by brain cells could activate microglia, alone or together with inflammatory cytokines, since protective antibodies could not cross the BBB, leading to neuro-inflammation and contributing to long-COVID. Hence, there is urgent need to better understand the neurotoxic effects of the spike protein and to consider possible interventions to mitigate spike protein-related detrimental effects to the brain, possibly via use of small natural molecules, especially the flavonoids luteolin and quercetin. (Theoharides, 2022).

Nutraceuticals and Cytokines, Covid Spike Proteins, mRNA Spike Proteins, Inflammation, and Long Covid Vitamin B6 (Pyridoxine)

Pyridoxal 5'-phosphate (PLP) is an active form of pyridoxine and is an essential cofactor in various inflammatory pathways with deficiency leading to immune dysregulation. PLP has an inverse relationship with plasma IL-6 and TNF-α in chronic inflammatory conditions. During inflammation, the utilization of PLP increases results in its depletion, suggesting that COVID-19 patients with high inflammation may have deficiency. Low PLP levels have been noted in patients with type-2 diabetes, cardiovascular disease and in the elderly [[19], [20], [21]], groups who are at higher risk of poorer COVID-19 outcomes. Dysregulation of immune responses and increased risk of coagulopathy have also been noted among COVID-19 patients. In a recent preprint it is suggested that PLP supplementation mitigates COVID-19 symptoms by regulating immune responses, decreasing pro-inflammatory cytokines, maintaining endothelial integrity and preventing hypercoagulability [22]. In fact, it was shown three decades ago that PLP levels reduce abnormalities in platelet aggregation and blood clot formation [23]. Recently researchers at Victoria University reported that vitamin B6 (as well as B2 and B9) upregulated IL-10, a powerful anti-inflammatory and immunosuppressive cytokine which can deactivate macrophages and monocytes and inhibit antigen-presenting cells and T cells [24]. COVID-19 patients often respond to the virus by mounting an excessive T cell response and secretion of pro-inflammatory cytokines. It may be that PLP is able to contribute to dampening the cytokine storm and inflammation suffered by some COVID-19 patients. (Shakoor, 2021).

Vitamin B9 (Folate)

Folate is an essential vitamin for DNA and protein synthesis and in the adaptive immune response. Furin is an enzyme associated with bacterial and viral infections and is a promising target for treatment of infections. Recently, it was noted that folic acid was able to inhibit furin, preventing binding by the SARS-CoV-2 spike protein, preventing cell entry and virus turnover. Therefore, it was suggested that folic acid could be beneficial for the management of COVID-19-associated respiratory disease in the early stages [25]. A recent preprint report that folic acid and its derivatives tetrahydrofolic acid and 5-methyl tetrahydrofolic acid have strong and stable binding affinities against the SARS-CoV-2, through structure-based molecular docking. Therefore, folic acid may be used as a therapeutic approach for the management of COVID-19 [26]. (Shakoor, 2021).

Vitamin B12 (Cobalamin)

Vitamin B12 is essential for red blood cell synthesis, nervous system health, myelin synthesis, cellular growth and the rapid synthesis of DNA. The active forms of vitamin B12 are hydroxo-, adenosyl- and methyl-cobalamin. Vitamin B12 acts as a modulator of gut microbiota and low levels of B12 elevate methylmalonic acid and homocysteine, resulting in increased inflammation, reactive oxygen species and oxidative stress [15]. Hyperhomocysteinemia causes endothelial dysfunction, activation of platelet and coagulation cascades, megaloblastic anemia, disruption of myelin sheath integrity and decreased immune responses [[27], [28], [29], [30]]. However, SARS-CoV-2 could interfere with vitamin B12 metabolism, thus impairing intestinal microbial proliferation. Given that, it is plausible that symptoms of vitamin B12 deficiency are close to COVID-19 infection such as elevated oxidative stress and lactate dehydrogenase, hyperhomocysteinemia, coagulation cascade activation, vasoconstriction and renal and pulmonary vasculopathy [28,31]. In addition, B12 deficiency can result in disorders of the respiratory, gastrointestinal and central nervous systems [30]. Surprisingly, a recent study showed that methylcobalamin supplements have the potential to reduce COVID-19-related organ damage and symptoms A clinical study conducted in Singapore showed that COVID-19 patients who were given vitamin B12 supplements (500 μg), vitamin D (1000 IU) and magnesium had reduced COVID-19 symptom severity and supplements significantly reduced the need for oxygen and intensive care support [33]. (Shakoor, 2021).

Vitamin D

Vitamin D enhances cellular immunity, in part by reducing the cytokine storm induced by the innate immune system. The innate immune system generates both pro-inflammatory and anti-inflammatory cytokines in response to viral and bacterial infections, as observed in COVID-19 patients [30]. Vitamin D can reduce the production of pro-inflammatory Th1 cytokines, such as tumor necrosis factor α and interferon γ [31]. Administering vitamin D reduces the expression of pro-inflammatory cytokines and increases the expression of anti-inflammatory cytokines by macrophages ([17] and references therein).

Vitamin D supplementation also enhances the expression of genes related to antioxidation (glutathione reductase and glutamate-cysteine ligase modifier subunit) [40]. The increased glutathione production spares the use of ascorbic acid (vitamin C), which has antimicrobial activities [41,42], and has been proposed to prevent and treat COVID-19 [43]. (Grant, 2020).

Vitamin D and ACE2

The ACE2 receptor is expressed in the lung, heart, kidney, and intestinal cells. The ACE2 enzyme is made of an N-terminal peptidase domain (PD) and a C-terminal collectrin-like domain, ending in a transmembrane helix. The SARS-CoV-2 virus interacts with the PD of ACE2, which is known to have a claw-like structure for host cell entry. When the S-protein of SARS-CoV-2 merges with the ACE2 receptors, transmembrane serine protease 2 proteolytically cleaves ACE2 and allows the virus particles to enter the host cell, replicate, and have cell-to-cell transmission. In vitro studies demonstrated a direct correlation between the expression of ACE2 and increase in the infection of the lungs and other tissues by SARS-CoV-2. 74 RAAS inhibitors that can block the ACE2 receptor to which S protein latches onto can prevent viral entry into the heart and lungs and protects them from being injured by the SARS-CoV-2 infection. [72], [74] There is also a possibility that RAAS inhibitors can cause a retrograde feedback mechanism that upregulates ACE2 receptors, which allows an increase in the binding of the S protein to the ACE2 receptors and therefore causes an increase in viral entry to the heart and lungs. [74] Additionally, as spike glycoproteins bind with the ACE2 receptor, this interaction reduces the ability of ACE2 to convert Ang II to Ang 1-7. This leads to lung injury and pneumonia because of the accumulation of Ang II, a hormone that can increase the presence of reactive oxygen species (ROS) in the body, which in turn also increases oxidative stress in the body. [74], [77] The interplay between ACE2 and vitamin D has been reported. [78]. (Grant, 2020).

Vitamin K

The evidence suggests a correlation between vitamin K2 deficiency in COVID patients and worsens clinical course due to the enhanced fiber mineralization. It has been reported that vitamin K2 deficiency is strongly associated with admission to ICU. In addition, the low levels of vitamin K2 seem to contribute to increasing levels of IL-6 cytokine protein release and Th2 cytokine spike protein storm activation (Parisi, 2021).

Studies backed by Kappa Bioscience found that deficiency in either vitamin D3 or vitamin K2 increased the risk of COVID-19 infection. The research also revealed more severe outcomes if COVID-19 patients are deficient in both nutrients. He details that vitamin D activates immune cells at the beginning of an infection and helps to block a key inflammatory chemical mediator—nuclear factor (NF) kappa B. Meanwhile, the primary modulator of inflammation is vitamin K2. "Vitamin K2 has been shown to inhibit NF kappa B as well as other interleukins that lead to the cytokine storm in COVID-19 infections." (Green, 2021).

Recent studies evaluating serum K2 levels in COVID-19 hospitalized patients found that patients with poor outcomes of COVID-19 had the lowest levels of vitamin K2. In comparison, people tested negative for SARS-CoV-2 infection showed adequate vitamin K2 levels. (Kappa, 2020).

Quercetin

The severe acute respiratory syndrome coronavirus 2 (SARS-CoV-2) is the cause of the ongoing global pandemic known as COVID-19. Based on the potential antiviral role of quercetin, and on its described anti-blood clotting, anti-inflammatory and antioxidant properties, we hypothesize that subjects with mild COVID-19 treated with Quercetin Phytosome® (QP), a novel bioavailable form of quercetin, may have a shorter time to virus clearance, a milder symptomatology, and higher probabilities of a benign earlier resolution of the disease.

The development of an effective adaptive immune response can limit the SARS CoV-2 viral infection, but the uncontrolled activation of innate immune cells results in an aggressive hyperinflammatory response with the release of an excessive amount of pro inflammatory cytokines in a process known as "cytokine storm". [8] The cytokine storm leads to increased risk of vascular hyperpermeability, acute respiratory distress syndrome (ARDS), multiorgan failure, and eventually death when the high cytokine concentrations are unabated over time. The cytokine storm is believed to be the major underlying cause of large number of COVID-19 deaths. Therefore, a timely intervention of well tolerated agents that can modulate or prevent the cytokine storm and the viral replication imbalance are potentially the strategies to prevent the severe COVID-19 disease development. [9] Quercetin, a flavonoid with an excellent safety profile, has powerful antioxidant, anti-inflammatory, immunomodulatory and antiviral properties, and can potentially help in the early stage of SARS-CoV-2 viral infection to prevent disease development and progression. [10,11]

As for most of polyphenols, the practical use of quercetin is limited by its low solubility and reduced oral absorption. [22,23] (Di Pierro, 2021).

This disclosure combines Quercetin with Bromelain to increase its bioavailability and thereby its efficacy.

The major druggable targets of SARS-CoV-2 include 3-chymotrypsin-like protease (3CLpro), papain-like protease (PLpro), RNA-dependent RNA polymerase, and spike (S) protein. Quercetin inhibits 3CLpro and PLpro with a docking binding energy corresponding to −6.25 and −4.62 kcal/mol, respectively. Quercetin has a theoretical, but significant, capability to interfere with SARS-CoV-2 replication, with the results showing this to be the fifth best compound out of 18 candidates. On the basis of the clinical COVID-19 manifestations, the multifaceted aspect of quercetin as both anti-inflammatory and thrombin-inhibitory actions, should be taken into consideration. (Derosa, 2020).

Bromelain

Interestingly, a recent experimental study demonstrated that bromelain inhibits infection of VeroE6 cells by SARS-CoV-2 through blocking the virus binding and entry into cells via downregulation of ACE-2 and TMPRSS2 expression, and cleavage of the SARS-CoV-2 spike protein, presenting a novel promising therapeutic option that warrants further investigation.

Notably, the latter action supports a potential role of bromelain in alleviating COVID-19 symptoms such as cough, fever and pain, and the more serious implications of inflammation, thrombosis, and edema Importantly, bromelain exerts dose-dependent anticoagulant effects. (Panagiotis, et al., 2022).

Bromelain is a cysteine protease, isolated from the pineapple stem (Ananas comosus) and is classically used in trauma for its known anti-inflammatory and anti-edema properties. [238] Moreover, bromelain inhibits cyclooxygenase and modulates prostaglandins and thromboxane, affecting both inflammation and coagulation, and also hydrolyzes bradykinin, supporting its potential role in alleviating COVID-19 symptoms. [239] (Parisi, 2021).

Bromelain is a cysteine protease, isolated from the pineapple stem (Ananas comosus) [9]. Traditionally, it has been used for its anti-inflammatory and healing effects in cases of arthritis and injury, while it has been approved in Europe for the debridement of burn wounds. Experimental studies have demonstrated that bromelain presents unique immunomodulatory actions: 1) downregulation of the pro-inflammatory prostaglandin E-2 (PGE-2) through inhibition of NF-kB and cyclooxygenase 2 (COX-2); 2) upregulation of the anti-inflammatory PGE-1; 3) activation of inflammatory mediators (interleukin 1b, interleukin-6, tumor necrosis factor-a and interferon-g) as an acute response to cellular stress, but also inhibition of inflammatory mediators in states of overt cytokine production; 4) modulation of T cell responses in vitro and in vivo; and 5) enhancement of T-cell dependent antigen specific B cell antibody responses [5,10-14].

Importantly, bromelain exerts dose-dependent anticoagulant effects: 1) downregulation of PGE-2 and thromboxane A2 (TXA2), thus leading to relative excess of prostacyclin; 2) promotion of fibrinolysis by stimulating the conversion of plasminogen to plasmin and prevention of platelet aggregation. Bromelain also hydrolyzes bradykinin and reduces kininogen and bradykinin levels in serum and tissues, improving inflammation and edema as shown in animal studies [15]. Notably, the latter action supports a potential role of bromelain in alleviating COVID-19 symptoms such as cough, fever and pain, and the more serious implications of inflammation, thrombosis, and edema (FIG. 1). The effect of bromelain on PGE-2 inhibition exceeds that of prednisone and aspirin, presenting very low toxicity and no major side effects [12,16]. (Kritis, 2020).

Zinc

Zinc ($Zn^{+2}$) mediates numerous non-specific and specific immunological functions: [16,17] From normal development and function of cells, [18,19] including those regulating nonspecific immunity, inter alia, activity of natural killer (NK) cells and neutrophils, and macrophage function; to maintaining expression of tight-junction proteins between lung-lining muco-epithelial cells, blocking entry of pathogens; from increasing cilia length and ciliary beat-frequency in those cells' mechanical clearance of surface "litter" such as virus particles, and repair of such function in coronavirus-damaged lung cells; to immune response modulation, [20, 21] tamping down on overshooting inflammatory immune responses [22] (thus preventing, for example, high levels of inflammatory mediators such as destructive reactive oxygen and nitrogen species) and normalizing the ratios of diverse immune cell types. Additionally, zinc is strongly implicated in inhibiting viral binding to cell membrane ACE2 receptors used by the coronavirus to latch onto the outside of potential host cells as an essential step preparatory to entering and invading those cells; and for its inhibiting effect on functioning of viral replication enzymes such as retroviral RNA replicase, [23] thus blunting the attack by those virus particles that do gain entrance to host cells.

While zinc is highly recommended for its broad range of anti-(retro) viral benefits, high serum Zn+2 levels carry risks of zinc toxicity [24,25] and, even at non-toxic elevated levels, competition with and depletion of other micronutrients, such as copper. [26] It would, therefore, be desirable to achieve effective intra-cellular zinc levels while keeping serum zinc levels relatively normal (with concomitant monitoring and, where appropriate, judicious adjustment of other micronutrient levels). To that end, we factored into the study 2 Journal of Evidence-Based Integrative Medicine formulations zinc ionophores for enhanced transport of zinc into human cells to effect intra-cellular zinc levels that may confer prophylactic and therapeutic benefits against (retro)viral infections. (Margolin, 2021).

A nutrient found throughout your body, helps your immune system and metabolism function. The study data clearly show that a significant number of COVID-19 patients were zinc deficient. These zinc deficient patients developed more complications, and the deficiency was associated with a prolonged hospital stay and increased mortality.

Zinc has been shown to exhibit antiviral properties by inhibition of RNA synthesis, viral replication, DNA polymerase, reverse transcriptase, and viral proteases (Read et al., 2019, Ko et al., 2018, Xue et al., 2014). However, the literature is unclear regarding SARS-CoV-2 and zinc. Interestingly, hydroxychloroquine, a drug used initially in the management of COVID-19, is an ionophore that transports zinc across the hydrophobic cell membrane (Xue et al., 2014, Rahman and Idid, 2020). Moreover, evidence specifically suggests that zinc supplements with antiviral drugs containing zinc ionophores precisely target and bind to SARS-CoV-2 preventing its replication within the infected host cells (te Velthuis et al., 2010). Intracellularly, zinc binds with RNA-dependent RNA polymerase causing elongation inhibition and decreased template binding of the viral mRNA (Rahman and Idid, 2020, te Velthuis et al., 2010). (Jothimani, et al., 2020).

Glutathione

Lung inflammation is the main cause of life-threatening respiratory disorders at the severe stage of SARS-CoV-2 infection, characterized by the so-called "cytokine release syndrome (CRS)". The key to fighting this harmful inflammatory response resides in: (i) addressing the mechanism of the virus penetration into the cell, mediated by binding to and inactivation of the ACE2 protein; (ii) contrasting the exacerbation of the inflammatory response.

The anti-inflammatory effects of reduced glutathione (GSH) are exerted through the inhibition of ACE activity, decrease of reactive oxygen species (ROS) production and reduction of NF-kB activation. The balance ACE/ACE2 is shifted toward ACE by the oxidized form of glutathione (GSSG) and by renin and by viral infection. (Silvagno, 2020).

Endogenous glutathione deficiency appears to be a crucial factor enhancing SARS-CoV-2-induced oxidative damage of the lung and, as a result, leads to serious manifestations, such as acute respiratory distress syndrome, multiorgan failure, and death in COVID-19 patients. Long-term and severe manifestations of COVID-19 infection in one of our patients with marked glutathione deficiency suggest that the degree of glutathione decrease correlates negatively with viral replication rate and that an increasing viral load exacerbates oxidative damage of the lung. This finding suggests that the virus cannot actively replicate at higher levels of cellular glutathione, and therefore, milder clinical symptoms are observed with lower viral loads. (Polonikov, 2020).

The boosted ANGII production can be due to decreased ACE2 expression and activity; this is the case with coronavirus infection, which recognizes ACE2 as its extracellular binding site [29]. Compared to SARS-COV-1, SARS-CoV-2 has about 4-fold higher affinity for ACE2 [30]. Infection of cells by SARS viruses that bind ACE2 results in two effects: inhibition of ACE2 activity and decrease of ACE2 expression in infected cells [29,31,32]. The increased ANGII, through binding to AT1R, activates NADPH oxidases that transfer an electron from NADPH to 02 generating several radical species, which can be scavenged by GSH. ROS-mediated oxidation can, in turn, alter gene expression through the induction of signaling cascades or the interaction with transcription factors [33]. Among these factors, a prominent role is played by NF-kB, whose role in inflammation in severe acute respiratory syndrome (SARS) has been demonstrated in both SARS-CoV-infected cultured cells and mice [34]. Drugs that inhibit NF-κB activation led to a reduction in inflammation and lung pathology. NF-kB is involved in inflammation through multiple mechanisms. In vitro, the viral nucleocapsid (N) protein activates interleukin-6 (IL-6) expression through NF-kB binding at the promoter region of the gene [35]. High levels of IL-6 in the acute stage associated with lung lesions were found in SARS patients [36]. By reducing ROS production, GSH inhibits NF-kB activation and consequently keeps the cytokine storm under control. (Silvagno, 2020).

N-Acetylcysteine (NAC)

Viral spike proteins play important roles in the viral entry process, facilitating attachment to cellular receptors and fusion of the viral envelope with the cell membrane. Severe acute respiratory syndrome coronavirus 2 (SARS-CoV-2) spike protein binds to the cellular receptor angiotensin converting enzyme-2 (ACE2) via its receptor-binding domain (RBD). The cysteine residue at position 488, consisting of a disulfide bridge with cysteine 480 is located in an important structural loop at ACE2-binding surface of RBD, and is highly conserved among SARS-related coronaviruses. We showed that the substitution of Cys-488 with alanine impaired pseudotyped SARS-CoV-2 infection, syncytium formation, and cell-cell fusion triggered by SARS-CoV-2 spike expression. Consistently, in vitro binding of RBD and ACE2, spike-mediated cell-cell fusion, and pseudotyped viral infection of VeroE6/TMPRSS2 cells were inhibited by the thiol-reactive compounds N-acetylcysteine (NAC) and a reduced form of glutathione (GSH). Furthermore, we demonstrated that the activity of variant spikes from the SARS-CoV-2 alpha and delta strains were also suppressed by NAC and GSH. (Murae, 2022)

Hydrogen sulfide (H2S) levels at hospital admission may be of importance since this gasotransmitter has been shown to be protective against lung damage through its antiviral, antioxidant, and anti-inflammatory actions. Many COVID-19 cases have been described demonstrating remarkable clinical improvement upon administration of high doses of N-acetylcysteine (NAC). NAC is a renowned pharmacological antioxidant substance acting as a source of cysteine, thereby promoting endogenous glutathione (GSH) biosynthesis as well as generation of sulfane sulfur species when desulfurated to H2S. (Bourgonje, 2021).

RNA viruses need active NF-κB pathway support within host cells in order to replicate. For human coronaviruses (HCoV-229E), suppression of NF-κB significantly reduced the replication rate. [22] Therefore, drugs that inhibit NF-κB activation could potentially reduce viral replication. NAC has been demonstrated to inhibit NF-κB, as well as the replication of human influenza viruses (H5N1, Vietnam/VN1203 strain) in human lung epithelial cells in a dose dependent manner (5 to 15 mM). NAC also reduced the production of pro-inflammatory cytokines (IL-8, CXCL10, CCL5 and IL-6), thus reducing chemotactic migration of monocytes. [23] In addition, NAC has also been showed to inhibit replication of other viruses, such as human immunodeficiency virus (HIV) [24] and respiratory syncytial virus (RSV). [25] This means that, theoretically, NAC has the potential to inhibit SARS-Cov-2 as well because of its ability to negatively regulate NF-∈B. (Shi, 2020).

Bourgonje et al. describes the potential role of hydrogen sulfide (H2S) as a fundamental host defense factor against SARS-CoV-2 infection. [4] Low serum levels of hydrogen sulfide (H2S) in patients with COVID-19 pneumonia have been shown to be negatively associated with inflammatory biomarkers such as IL-6 and C-reactive protein (CRP), and also associated with a poor prognosis. [5] Endogenous H2S production can be increased therapeutically by administering N-acetylcysteine (NAC), which can be seen as a potential treatment strategy for COVID-19 patients. [4] NAC may also replenish intracellular reduced glutathione (GSH) pools by providing l-cysteine, a precursor for GSH synthesis. [6] Moreover, NAC has shown the ability to restore the intracellular redox imbalance in vitro experiments. [7] (Avdeev, 2022).

Alpha Lipoic Acid

Alpha lipoic acid is an antioxidant that controls respiratory inflammation and, along with glutathione and NAC, quells cytokine storms. Alpha lipoic acid exhibits strong antioxidant properties and modulates the immune system by regulating T cell activation making it a useful therapeutic candidate for cytokine storm triggering SARS-CoV-2 infection.

Administration of ALA after SARS-CoV-2 replication may diminish ACE1 increase and ACE2 decrease, thereby contributing to the prevention of cardiopulmonary damage by preventing cytokine expression. Previously, it has been shown that influenza virus (IVFujian01) increases NF-κB and caspase activities in MDCK cells. Cells with low NF-κB activity are resistant to influenza virus infection (Nimmerjahn et al., 2004). Thus, preventing NF-κB activation plays a major role in the treatment of influenza virus infection. ALA has been shown to inhibit influenza spread by blocking NF-κB activation (Bai et al., 2012). Another study has shown that ALA prevents TNF-α-mediated apoptosis caused by influenza A virus (Severa et al., 2007).

We suggest that ALA, used after viral replication, may alleviate the prognosis of the disease by regulating T cell activity and suppressing NF-κB. Besides, ALA being also used as an immunomodulator allows us to speculate its potential use and benefits of use in combination with antiviral agents may prove to be a more effective treatment of choice by reducing the side effect potential of those drugs. This is principally because of the fact that ALA will reduce the NADPH oxidase activity resulting in decreased cytokine expression, free oxygen radicals, and thus tissue damage. Inhibiting virus replication as well as limiting excess inflammation is very important to the treatment of COVID-19. For this purpose, the agents regulating the immune system should be considered together with antiviral treatments. ALA, having the potential of inhibiting cytokine expression, allows us to speculate on its potential benefit of use in balancing the cytokine storm. (Sayiner, 2020).

Without sufficient ALA the mitochondria would be unable to breakdown alpha-keto acids and free amino acids that are needed to produce acetyl-coenzyeme A (CoA) and provide important intermediates that supply the citric acid cycle, as well as protect the electron transport chain from free radical damage so maximum energy production can take place (Bodnar, 2017).

Selenium

Selenium is one of the essential trace elements in the human body, playing a pivotal role in modulating the function of the immune system, maintaining redox homeostasis, and diminishing inflammatory cytokine cascade [29]. Previously, we suggested several molecular mechanisms for the antiviral and anti-inflammatory effects of selenium supplementation, whereas both the immune boosting and the antioxidant effects of selenium are demonstrated in clinical studies [3]. To date, there are several studies suggesting a relationship between selenium deficiency and chronic inflammatory diseases such as cardiovascular, subfertility, cancer, and viral infections [13, 30, 31].

Additionally, a considerable aspect of selenium supplementation is associated with mutations in RNA viruses. Prior studies on influenza and Coxsackie viruses have demonstrated that in selenium-depleted hosts, there is a much greater chance for viral genome mutation [13]. This goes along with the recent dramatic health threats caused by new variants of SARS-CoV-2 [56]. Thus, it might be considered that keeping general population from becoming selenium deficient may prevent SARS-CoV-2 from further dangerous mutations.

Analysis of a cross-sectional study [20] in Germany of 35 COVID-19 patients (171 serum samples) showed that circulating selenium and SELENOP concentrations increased in the discharge group (n=29) during hospitalization and unlike deaths (n=6), and generally the amount of selenium and SELENOP in serum was higher in discharged patients compared to deaths. These authors also investigated the circulating level of selenium and SELENOP in 35 patients (173 serum samples, discharges=28, deaths=7) in another study, and the results go along with each other [27]. Another study [22] conducted by the same research team on 33 COVID-19 patients suggested remarkably lower levels of serum selenium, SELENOP, and glutathione peroxidase-3 in deaths comparing to discharges. According to their results, COVID-19 patients showed a notable deficit in total selenium and SELENOP concentrations in comparison with reference data from a European survey on 1,915 adults.

Antiaging: A telomere is the end of a chromosome. Telomeres are made of repetitive sequences of non-coding DNA that protect the chromosome from damage. Each time a cell divides, the telomeres become shorter. Eventually, the telomeres become so short that the cell can no longer divide. This is how people get old. In a recent study Selenium increased telomere lengths which helps fight disease and aging.

In conclusion, most of the examined COVID-19 patients indicated a low selenium level. Selenium deficiency might be considered as an indicator for the severity, mortality, and overall risk of COVID-19. (Fakhrolmobasheri, 2021).

Curcumin

Curcumin (diferuloylmethane) is a natural phenol found in turmeric (Curcuma longa), a member of the ginger family of plants [4]. Curcumin modulates inflammation preventing the subsequent cytokine storm by inhibiting multiple transcription factors such as nuclear factor kappa B (NF-kB) and signal transducer and activator of transcription 3 (STAT-3), and downregulating the proinflammatory cytokines, as this has been demonstrated in human macrophages after influenza virus infection [4,6]. Additionally, curcumin inhibits ACE modulating angiotensin II synthesis and downregulating inflammation, while it also promotes fibrinolysis and the anticoagulation process [4,6,7]. The antiviral actions of curcumin against multiple viruses (influenza and hepatitis viruses, herpes viruses, human papilloma virus, human immunodeficiency virus, severe acute respiratory syndrome coronavirus and other coronaviruses), bacteria and fungi have been established by experimental evidence [8]. Remarkably, recent evidence from in silico studies has demonstrated that curcumin prevents SARS-CoV-2 entry into cells by blocking the viral binding sites and the cell ligands (spike protein, ACE-2 receptors and basigin), downregulating trans-membrane serine protease 2 (TMPRSS-2), and by interfering with viral replication through the interaction with various viral proteins [4]. However, the minimal absorption of curcumin following oral administration presents a major limitation in its bioavailability [6]. (Kritis, 2020).

Endotoxins released by microorganisms activate macrophages and neutrophils to produce inflammatory cytokines and eicosanoids such as thromboxane A2 [4]; anti-inflammatory medications such as COX-2 inhibitors could cause an imbalance prostaglandin production. Greater affinity for the COX-2 isoform could cause accumulation of thromboxane, a pro-aggregatory and vasoconstrictive prostaglandin produced from the COX-1 isoform, and therefore increase cardiovascular risk in patients with COVID-19. In this context, curcumin is unique because of its anti-inflammatory and antithrombotic effects. In patients with COVID-19 who exhibit long-term thromboembolic complications, curcumin treatment could reduce thromboembolic complications with lower bleeding risk, when low molecular weight heparin or unfractionated heparin treatment is stopped or in the absence of heparin treatment. Several preclinical studies have shown that curcumin could prevent cytokine storms [24] and COVID coagulopathy [28, 29], and function as an antiviral drug [35]. To our knowledge, our study is the first to describe the efficacy of orally administered curcumin with piperine in the symptomatic treatment of COVID-19 (Pawar, 2021).

CBDa Cannabidiolic Acid and CBGa Cannabigerolic Acid

As a complement to vaccines, small-molecule therapeutic agents are needed to treat or prevent infections by severe acute respiratory syndrome coronavirus-2 (SARS-CoV-2) and its variants, which cause COVID-19. Affinity selection-mass spectrometry was used for the discovery of botanical ligands to the SARS-CoV-2 spike protein. Cannabinoid acids from hemp (Cannabis sativa) were found to be allosteric as well as orthosteric ligands with micromolar affinity for the spike protein. In follow-up virus neutralization assays, cannabigerolic acid and cannabidiolic acid prevented infection of human epithelial cells by a pseudovirus expressing the SARS-CoV-2 spike protein and prevented entry of live SARS-CoV-2 into cells. Importantly, cannabigerolic acid and cannabidiolic acid were equally effective against the SARS-CoV-2 alpha variant B.1.1.7 and the beta variant B.1.351. Orally bioavailable and with a long history of safe human use, these cannabinoids, isolated or in hemp extracts, have the potential to prevent as well as treat infection by SARS-CoV-2 (Breemen, 2022).

(Breemen, 2022). van Breemen R B, Muchiri R N, Bates T A, Weinstein J B, Leier H C, Farley S, Tafesse F G. Cannabinoids Block Cellular Entry of SARS-CoV-2 and the Emerging Variants. J Nat Prod. 2022 Jan. 28;85(1): 176-184. doi: 10.1021/acs.jnatprod.1c00946. Epub 2022 Jan. 10. PMID: 35007072; PMCID: PMC8768006. https://pubmed.ncbi.nlm.nih.gov/35007072/

Cannabidiol (CBD)

Cannabidiol Inhibits SARS-CoV-2 Replication and Promotes the Host Innate Immune Response. The rapid spread of COVID-19 underscores the need for new treatments. Here we report that cannabidiol (CBD), a compound produced by the cannabis plant, inhibits SARS-CoV-2 infection. CBD and its metabolite, 7-OH-CBD, but not congeneric cannabinoids, potently block SARS-CoV-2 replication in lung epithelial cells. CBD acts after cellular infection, inhibiting viral gene expression and reversing many effects of SARS-CoV-2 on host gene transcription. CBD induces interferon expression and up-regulates its antiviral signaling pathway. A cohort of human patients previously taking CBD had significantly lower SARSCoV-2 infection incidence of up to an order of magnitude relative to matched pairs or the general population. This study highlights CBD, and its active metabolite, 7-OH-CBD, as potential preventative agents and therapeutic treatments for SARS-CoV-2 at early stages of infection To test the effect of CBD on SARS-CoV-2 replication, we pretreated A549 human lung carcinoma cells expressing exogenous human ACE-2 receptor (A549-ACE2) for 2 hours with 0-10 µM CBD prior to infection with SARS-CoV-2. After 48 hours, we monitored cells for expression of the viral spike protein (S). For comparison, we also treated cells over a similar dose range with an MLK inhibitor (URMC-099) previously implicated as an antiviral for HIV [12] and KPT-9274, a PAK4/NAMPT inhibitor [13] that our analysis suggested might reverse many changes in gene expression caused by SARS-CoV-2. All three inhibitors potently inhibited viral replication under non-toxic conditions with EC50s ranging from 0.2-2.1 µM. CBD inhibited SARS-CoV-2 replication in Vero E6 monkey kidney epithelial cells as well. No toxicity was observed at the effective doses. We also determined that CBD suppressed replication of a related beta-coronavirus, mouse hepatitis virus (MHV), under non-toxic conditions with an EC50 of ~5 µM using A549 cells that express the MHV receptor (A549-MHVR), indicating the potential for more broader viral efficacy.

Our results suggest that CBD can block SARS-CoV-2 infection at early stages of infection, and CBD administration is associated with a lower risk of SARS-CoV-2 infection in humans. Furthermore, the active compound in patients is likely to be 7-OH-CBD, the same metabolite implicated in CBD treatment of epilepsy. The substantial reduction in SARS-CoV-2 infection risk of approximately an order of magnitude in patients who took FDA-approved CBD highlights the potential efficacy of this drug in combating SARS-CoV-2 infection. Finally, the ability of CBD to inhibit replication of MHV raises the possibility that CBD may have efficacy against new pathogenic viruses arising in the future. (Nguyen, 2021).

Cannabidiol inhibits SARS-Cov-2 spike (S) protein-induced cytotoxicity and inflammation through a PPARγ-dependent TLR4/NLRP3/Caspase-1 signaling suppression in Caco-2 cell line. Given the abundancy of angiotensin converting enzyme 2 (ACE-2) receptors density, beyond the lung, the intestine is considered as an alternative site of infection and replication for severe acute respiratory syndrome by coronavirus type 2 (SARS-CoV-2). Cannabidiol (CBD) has recently been proposed in the management of coronavirus disease 2019 (COVID-19) respiratory symptoms because of its anti-inflammatory and immunomodulatory activity exerted in the lung. In this study, we demonstrated the in vitro PPAR-γ-dependent efficacy of CBD (10-9-10-7 M) in preventing epithelial damage and hyperinflammatory response triggered by SARS-CoV-2 spike protein (SP) in a Caco-2 cells. Immunoblot analysis revealed that CBD was able to reduce all the analyzed proinflammatory markers triggered by Spike Protein incubation, such as tool-like receptor 4 (TLR-4), ACE-2, family members of Ras homologues A-GTPase (RhoA-GTPase), inflammasome complex (NLRP3), and Caspase-1. CBD caused a parallel inhibition of interleukin 1 beta (IL-1β), IL-6, tumor necrosis factor alpha (TNF-γ), and IL-18 by enzyme-linked immunosorbent assay (ELISA) assay. By immunofluorescence analysis, we observed increased expression of tight-junction proteins and restoration of transepithelial electrical resistance (TEER) following CBD treatment, as well as the rescue of fluorescein isothiocyanate (FITC)-dextran permeability induced by SP. Our data indicate, in conclusion, that CBD is a powerful inhibitor of SP protein enterotoxicity in vitro.

Molecules capable of reducing the hyperinflammatory response that characterizes the most severe clinical forms of COVID-19 are strategically essential in supporting therapies against SARS-CoV-2 infections. Such molecules can significantly reduce the damage deriving from the cytokine storm and might strongly reduce the need for intensive care units for the most compromised patients. CBD is suitable for this purpose, and if orally administered, as the antiepileptic CBD-based drug Epidiolex, it demonstrated itself capable of reducing the susceptibility caused by SARS-CoV-2 [27]. Moreover, as an anti-inflammatory and immunoregulatory agent, CBD has shown the therapeutic potential of certain advantages in controlling the picture of lung inflammation from COVID-19 and proving capable of markedly improve the symptoms of SARS-CoV-2 infection-mimicking model by poly (I: C)-induced ARDS [19] in mice. Moreover, CBD demonstrated itself capable of increasing the expression of apelin, a peptide with a significant role in the central and peripheral regulation of the immune system, CNS, metabolic, and cardiovascular system. These effects, added to its known anti-inflammatory properties identified at the lung level, are in line with other preclinical models of ARDS [33, 34]. In this sense, acting at the PPAR-γ site, CBD has been proposed as a drug of potential applicability in anti-COVID-19 protocols, as demonstrated by an increasing number of clinical trials that examine its protective effect in SARS-CoV-2 infections (NCT04731116; NCT04686539). In addition to these previous publications, our study first demonstrates, as far we know, new and potential effects of CBD in the intestinal epithelium, potentially able to counteract SARS-CoV-2 hyperinflammation in the gut. We consider this point extremely interesting since the emerging importance of the intestine in viral replication, especially for SARS-CoV-2 variants [12], the role exerted by intestinal mucosa in the immune response to viral attack mediated by SP in this site. Although our data refer to an in vitro model, and further in vivo investigations are needed, they indicate additional potential beneficial effects by CBD against COVID-19 that integrate with previously established lung protection. Moreover, by reducing ACE-2 expression and down-regulating RhoA-GTPase/NLRP3/Caspase-1 pathway, by a selective PPAR-γ involvement, CBD may potentially counteract viral entry and replication by the intestine. At the same time, this molecule can reduce the over-release of proinflammatory cytokine at the basis of systemic inflammatory dysfunction in most severe COVID-19 cases [13]. (Corpetti, 2021).

Cannabigerol (CBG)

CBG (Cannabigerol) mainly interacts with CB2 Receptors. CB2 receptors are predominantly found in the immune system. In late December 2019, a novel coronavirus (SARS-CoV-2 or CoV-19) appeared in Wuhan, China, causing a global pandemic. SARS-CoV-2 causes mild to severe respiratory tract inflammation, often developing into lung fibrosis with thrombosis in pulmonary small vessels and causing even death. Coronavirus Disease (COVID-19) patients manifest exacerbated inflammatory and immune responses, cytokine storm, prevalence of pro-inflammatory M1 macrophages and increased levels of resident and circulating immune cells. Men show higher susceptibility to SARS-CoV-2 infection than women, likely due to estrogens production. The protective role of estrogens, as well as an immune-suppressive activity that limits the excessive inflammation, can be mediated by cannabinoid receptor type 2 (CB2). The role of this receptor in modulating inflammation and immune response is well documented in fact in several settings. The stimulation of CB2 receptors is known to limit the release of pro-inflammatory cytokines, shift the macrophage phenotype towards the anti-inflammatory M2 type and enhance the immune-modulating properties of mesenchymal stromal cells. For these reasons, we hypothesize that CB2 receptor can be a therapeutic target in COVID-19 pandemic emergency.

The immune system has complex mechanisms to fulfill its function and respond to a variety of signaling molecules including hormones, neurotransmitters, and specific lipids, such as endocannabinoids (eCBs) [20]. The biological effects of cannabinoids are mediated through the activation of G-protein-coupled cannabinoid (CB) receptors [21]. The endocannabinoid system (ECS) includes the cannabinoid receptor type 1 (CB1) and 2 (CB2), the endogenous cannabinoids, and the enzymes for their metabolism. CB1 is mostly expressed in the central nervous system and is strongly associated with the psychoactive effects of cannabinoids [22]. CB1 is also expressed at low levels in peripheral tissues [23]. Instead, CB2 is highly expressed by immune cells (B cells, natural killer cells, monocytes, neutrophils, CD8 lymphocytes, CD4 lymphocytes) [24,25] and in several organs and tissues such as liver, spleen, nasal epithelium, thymus, brain, lung and kidney [26-28]. Both CB1 and CB2 receptors have been widely demonstrated to be important modulators of the immune system, potentially inducing immunosuppression [29]. CB2 is widely known for its immunomodulatory role, which is related to four events: (i) induction of apoptosis, (ii) suppression of cell proliferation, (iii) inhibition of proinflammatory cytokines production and increase in anti-inflammatory cytokines and (iv) induction of regulatory T cells [30]. It is therefore conceivable that, also in COVID-19, the activation of the ECS plays a role in preventing and/or influencing the development and the severity of the disease. (Rossi, 2020).

Recently, Canadian researchers have tested CBD extracts of 800 different *C. sativa* lines on 3D human models of oral, airways, and intestinal tissues and found 13 low THC/high CBD lines that modulated ACE2 and TMPRSS2 levels, which might lower the virus load (128). ACE2-reducing activity of cannabis-derived products were confirmed by a different group. They extracted a CBD, CBG, and THCV-containing fraction of a *C. sativa* strain and tested it in vitro in comparison to a standard phytocannabinoid agent. Both products reduced the secretion of pro-inflammatory cytokines IL-6, IL-8, CCL2, and CCL7 from the alveolar epithelial cell line A549, induced polarization of the macrophage cell line KG1 and increased the phagocytosis. CD36 and type II receptor for the Fc region of IgG (FcγRII) were upregulated. The researchers reported a certain superiority of the standard phytocannabinoids compared to the cannabis-derived fraction but cannot give recommendations for usage of cannabis in the treatment of COVID-19 (129). Another recent study simulated viral infections using the synthetic RNA Poly I: C and could show that Poly I: C-induced ARDS could be prevented by CBD (130) through the upregulation of apelin, a peptide regulating central and peripheral immunity that was severely downregulated in a murine model of ARDS (131). In the following two sections we will present the processes of regulation of the immune responses of endo- and phytocannabinoids (Paland, 2021).

Protective Effects of Cannabigerol on Cells of the Blood-Brain Barrier

Cannabidiol (CBD), one of the chemicals found in Cannabis sativa, has displayed a range of neuroprotective qualities, preventing neuronal loss, [6,7] attenuating astrocyte reactivity, [8] and dampening the neuroinflammatory response. [9] Unlike delta 9 tetrahydrocannabinol (D9-

THC), CBD does not activate the central cannabinoid receptors, CB1 or CB2, but activates a plethora of other targets including PPAR-c, TRPV1, and 5-HT1A receptors. [10-13] CBD has formulations (alone and with D9-THC) licensed by GW pharmaceuticals to treat rare childhood epilepsies and spasticity associated with multiple sclerosis. The protective effects of CBD in stroke models have been well documented, [14] specifically CBD has been shown to reduce infarct volume, [15,16] reduce glutamate toxicity, [9,17] attenuate mitochondrial dysfunction [18] and glial activation. [6,19] In a co-culture BBB model CBD preserved barrier integrity after oxygen-glucose deprivation (OGD), which was mediated at least in part by PPAR-c and 5-HT 1A receptors. [12] Cannabigerol (CBG) and cannabidivarin (CBDV) are neutral cannabinoids present in cannabis and studies have found these compounds share similar pharmacological characteristics to CBD. Like CBD, they do not produce feelings of euphoria and display antioxidant and anti-inflammatory properties, as well as interacting with a range of target proteins including TRPV1, 13 PPAR-c, 20 5-HT1A, and CB2. [21] Recently our group conducted a systematic review focusing on the neuroprotective properties of minor phytocannabinoids (other than D9-THC or CBD) and found that CBG and CBDV show efficacy in models of Huntington's disease, Alzheimer's, and epilepsy, with CBG mediating its protective effects through PPAR-c activation, [22] the same mechanism by which we have shown that CBD protects BBB integrity. [12] CBG has displayed prominent anti-inflammatory and antioxidant capabilities [20,29,30].

In astrocytes CBG and CBDV attenuated levels of interleukin-6 (IL-6) spike protein and lactate dehydrogenase (LDH). In astrocytes, CBG decreased levels of DNA damage proteins (spike proteins) (Stone, 2021).

Cannabinol (CBN)

Cannabinol is a cannabinoid isolated from the plant Cannabis that is a metabolite of tetrahydrocannabinol (THC), with potential immunosuppressive and anti-inflammatory activities. Cannabinol preferentially binds to the cannabinoid G-protein coupled receptor CB2, which is mainly expressed on a variety of immune cells, such as T-cells, B-cells, macrophages and dendritic cells. Stimulation of CB2 receptors by cannabinol may both trigger apoptosis in these cells and inhibit the production of a variety of cytokines. Cannabinol exerts minimal affinity for CB1 and has a weak effect on the central nervous system (NCBI, 2022).

Nigella Sativa and Thymoquinone

Having a range of bioactive components such as thymoquinone and nigellimine, black seed might offer a number of benefits to treat COVID-19 such as (i) blocking the entry of the virus into pneumocytes and (ii) providing ionophore for enhanced uptake of Zn2+ which in turn can enhance host immune response against SARS-CoV-2 as well as inhibit its replication by blocking the viral RdRp. (Rahman, 2020).

Molecular docking of compounds from N. sativa and some antiviral drugs was performed to determine their binding affinity with SARS-CoV-2-related molecular targets such as main proteases (6LU7 and 6Y2E), main peptidase (2GTB), angiotensin converting enzyme 2 (ACE2), and heat shock protein A5. The binding of some natural compounds might prevent the adhesion of coronavirus to host epithelial cells. Nigelledine, an alkaloid in N sativa, docked with 6LU7 active sites showed an energy complex score close to chloroquine and better than hydroxychloroquine and favipiravir. a-Hederin, a saponin in N sativa, docked with 2GTB active sites showed an energy score better than chloroquine, hydroxychloroquine, and favipiravir.[24]

Thymoquinone, the main essential oil constituent of N sativa, had a binding affinity with 6LU7, ACE2, and heat shock protein A5 active sites with a score less than hydroxychloroquine in 6LU7 and ACE2. [25], [26] Also, hederagenin, a saponin in N sativa, docked with 6LU7, 6Y2E, ACE2, and GRP78 active sites showed a binding score less than saquinavir in 6LU7 and 6Y2E. [27], [28] Thymohydroquinone showed moderate docking energy with SARS-CoV-2 6LU7, endoribonucleoase, ADP-ribose-1"-phosphatase, RNA-dependent RNA polymerase, the binding domain of the SARS-CoV-2 spike protein, and human ACE2. [29] Nigellidine showed high binding affinity SARS-CoV-2 enzymes and proteins such as N-terminus-protenase, 6LU7, nonstructural protein 2, spike-glycoprotein, and nucleocapsid. Nigellidine had high binding energy with human receptors, inflammatory signal molecules, and other proteins such as human IL1R (1itb), TNFR1 (1ncf), and TNFR2 (3alq). [30]

Therefore, certain natural compounds found in N sativa such as nigellidine, α-hederin, hederagenin, thymohydroquinone, and thymoquinone were potentially active compounds that might inhibit coronavirus. (Koshak, 2020).

Using both black seed-extracted Thymoquinone (THQ) and commercially available pure THQ, we provide evidence for the first time that THQ possesses anticoagulant activity, as determined by in vitro coagulation assays. Both pure THQ and black seed-extracted-THQ modulate normal blood coagulation with minimal effect in a narrow dose range. In contrast, pure THQ can effectively reverse coagulation to basal levels when triggered by TF present on pancreatic cancer cells and by lipopolysaccharide (LPS). We also performed mechanistic studies and confirm that THQ decreases blood coagulation directly by decreasing factor Xa inactivation in blood coagulation cascade and by interfering with the crosstalk between inflammation and thrombosis. (Muralidharan, 2016).

Sulforaphane

Following exploratory experiments using the in vitro CPE inhibition assay, Sulforaphane (SFN) was identified as a promising candidate to target the host cellular response, given that it is orally bioavailable, commercially available at low cost, and has limited side effects [18], [32]. We observed that SFN has dual antiviral and anti-inflammatory properties against coronaviruses. We determined that SFN has potent antiviral activity against HCoV-OC43 and multiple strains of SARS-CoV-2, including Delta and Omicron, with limited toxicity in cell culture. The similar results observed between the coronaviruses evaluated suggest that SFN could have broad activity against coronaviruses, a feature that may prove invaluable as new strains of pathogenic coronaviruses enter the human population.

The pathogenesis of many viral infections is associated with increased production of reactive oxygen species (ROS), which leads to cell death [34], [36]. Conversely, SFN increases antioxidant, anti-inflammatory, and antiviral defenses through multiple mechanisms [1], [7], including the activation of the cap'n'collar transcription factor NRF2 [37]. Under normal conditions, NRF2 remains in an inactive state by association with its inhibitor protein Kelch-like ECH-associated protein 1 (KEAP1) [38]. In response to oxidative stress, KEAP1 is inactivated, and NRF2 is released to induce NRF2-responsive genes that subsequently protect against stress-induced cell death [39].

The dual antiviral and anti-inflammatory properties of SFN have also been previously described for other viral infections. In vitro antiviral activity has been reported against influenza virus [41], and SFN treatment significantly limited lung viral replication and virus-induced inflammation in respiratory syncytial virus-infected mice [42].

As a potent NRF2 activator, SFN can modulate the host's immune response while also providing direct, NRF2-independent antiviral effects. Targeting the NRF2 pathway has been considered a promising approach to develop therapeutics for COVID-19 for multiple reasons [46], [48]. NRF2 deficiency is known to upregulate the angiotensin-converting enzyme 2 (ACE2), the primary mechanism of cell entry for SARS-CoV-2. The NRF2 activator oltipraz reduces ACE2 levels, suggesting that NRF2 activation might reduce the availability of ACE2 for SARS-CoV-2 entry into the cell49. Increased NRF2 activity also reportedly inhibits IL-6 and IL-1β gene expression [50], two cytokines known to play key roles in promoting the hyperactive immune response in severely ill COVID-19 patients51. Conversely, NRF2 activity is dysregulated in disease states that have been associated with increased severity of COVID-19 (e.g., diabetes) [52]. Further, NRF2 activity declines in older patients who are more susceptible to severe COVID-19 [53]. Recent reports suggest that NRF2-dependent genes are suppressed in SARS-CoV-2 infected cells and lung biopsies from COVID-19 patients [46]. Similarly, treatment of cells with NRF2 agonists 4-octyl-itaconate and dimethyl fumarate inhibited replication of SARS-CoV-2 in vitro [46]. (Ordonez, 2022).

Astaxanthin

Astaxanthin as a potential adjunctive supplement in COVID-19: H. pluvialis derived ASX is a natural oxycarotenoid with anti-inflammatory, immunomodulatory and potent antioxidant properties [[8], [9], [10], [11], [12], [13], [14]]. The potent antioxidant property of ASX implicating to its various biological activities has been demonstrated in both preclinical and clinical studies [8,10]. ASX is not a known viricide. However, it has been shown to suppress features of viral infection owing to its potent antioxidant, anti-inflammatory and immunomodulatory actions [[11], [12], [13], [14], [15], [16], [17]]. Studies including human trials have shown that ASX effectively regulates immunity and disease etiology, suggesting its wide array of potential therapeutic and nutritional support in prevention and treatment of various pathogenic diseases and metabolic disorders, all of which have elements of oxidative stress and/or inflammation in the pathogenesis [8,10,17]. The potential pharmacological effects of ASX include antioxidant [12,[9], [10], [11], [12], [13], [14],[37], [38], [39], [40], [41], [42], [43], [44], [45], [46]], anti-inflammatory [9,12,14,[54], [55], [56], [57], [58], [59], [60]] and immune-modulating [11,14, 15,[61], [62], [63]] as well as cardiovascular, neuro-, ocular- and skin-protective effects [8,17,37,64]. (Talukdar, 2020).

Inflammation acts like a double-edged sword and can be harmful if not appropriately controlled. COVID-19 is created through a novel species of coronavirus SARS-CoV-2 (2019-nCoV). Elevated levels of inflammatory factors such as interleukin-6 (IL-6), tumor necrosis factor-alpha (TNF-α), etc. lead to Acute Respiratory Distress Syndrome (ARDS) and severe complications of infection in the lungs of coronavirus-infected patients. Astaxanthin is a natural and potent carotenoid with powerful antioxidant activity as well as an anti-inflammatory agent that supports good health. The effects of astaxanthin on the regulation of cyclooxygenase-2 (COX-2) pathways and the reduction and suppression of cytokines and other inflammatory agents such as IL-6 and TNF-α have already been identified. Therefore, these unique features can make this natural compound an excellent option to minimize inflammation and its consequences (Ahmadi, 2021).

Astaxanthin has been known to inhibit the "Cytokine Storm". Natural astaxanthin, known for its exceptional antioxidant powers, has a strong ability to both balance and strengthen the immune system, hence improving the defense against inflammation and outside invaders (pathogens). Antioxidant Astaxanthin is 6,000 times stronger than Vitamin C (Zhang, Z, 2020).

Astaxanthin is one of the top antioxidants and is one of a very few that can cross the blood brain barrier to attack free radicals in the brain (Gleb, 2017). This is essential for brain and central nervous system wellbeing.

Our study systematically investigated the effects of ASTX on blood clots. Results showed that ASTX could inhibit coagulation, increase fibrinolytic activity and reduce platelet aggregation in hyperlipidemic rats. This action was mainly attributed to ASTX, which decreased the serum lipid and lipoprotein levels, increased the amount of antioxidants, and protected the endothelial and platelet functions. In conclusion, we demonstrated that ASTX could inhibit coagulation, increase fibrinolytic activity and reduce platelet aggregation in hyperlipidemic rats. These results indicate that ASTX is an effective complementary and alternative antihaemostatic drug. (Deng, 2017).

Synergistic Combinations

Vitamin D and Magnesium

Magnesium supplementation is recommended when taking vitamin D supplements. Magnesium helps activate vitamin D, which in turn helps regulate calcium and phosphate homeostasis to influence the growth and maintenance of bones. All the enzymes that metabolize vitamin D seem to require magnesium, which acts as a cofactor in the enzymatic reactions in the liver and kidneys [157]. The dose of magnesium should be in the range of 250-500 mg/d, along with twice that dose of calcium. (Grant, 2020).

Vitamin D and Glutathione

Cells usually maintain a reducing environment and oxidative stress occurs when the cellular levels of ROS outbalance the antioxidants. If ROS levels become too high, the redox environment is driven out of homeostasis, resulting in the oxidation of proteins, DNA, and other cellular components. Mechanisms to maintain redox status, detoxify the ROS, and balance the thiol-disulfide ratio are often triggered by the oxidation of thiol-based redox switches. These pathways are often mediated by redox-sensitive transcription factors, such as proteins with cysteine residues, which in conjunction with low-molecular-weight (LMW) thiols are scavengers of ROS such as H202. [69], [79] One of the most abundant LMW thiols is glutathione (GSH), a tripeptide (γ-glutamyl cysteinyl glycine) that functions as a major endogenous antioxidant. [80] GSH is the main cofactor for several enzymes that are responsible for detoxifying ROS. [14] Homeostasis of the cellular redox environment is also maintained through the action of various ROS-scavenging enzymes, including catalase, superoxide dismutase (SOD), glucose 6-phosphate dehydrogenase, glutathione reductase (GR), and glutathione peroxidase. The regulation and function of these enzymes are dependent on cellular conditions and the physiological concentration of vitamin D.

Cytoplasmic conditions are more reduced and regulated, with only~10% of protein cysteines existing as disulfide bonds, compared to the cell surface environment. [79] The extracellular environment lacks an effective redox-homeostasis system, and therefore antioxidant enzymes and LMW thiols are crucial in maintaining the extracellular redox environment. [79] Thiol-disulfide balance affects binding of the SARS-CoV-2 virus with the host cell receptor; when the ACE2 receptor and S protein are in the reduced state, binding is thermodynamically unfavorable. Regulation of oxidative stress has a direct impact on COVID-19 infection. This review on vitamin D elaborated on its role in maintaining the cellular redox status by regulating the expression of antioxidant enzymes and LMW thiols like GSH. In addition, it was observed that vitamin D affects the immune system; it modulates the innate and adaptive immune responses. Taken together, this review has provided a molecular-level understanding of the role of this essential molecule in reducing the risks of viral infections including the COVID-19. (Abdrabbo, 2021).

Vitamin D, Vitamin K, and Magnesium

The COVID-19 pandemic is a current pandemic of high international interest, caused by the coronavirus strain SARS-CoV-2. Up to date, there is no treatment to decrease the virus-caused infection and mortality rates. [10] More and more voices are being raised supporting the supplementation of Vitamin D3 to counter the pandemic outbreak with the correlated mortality rates as well as economic and social consequences. [19] In a recently published review article, Sharma et al. (2020) have critically discussed the association of vitamin D with viral infections. A recent clinical study from Iran (n=611) stated that there were no COVID-19 deaths in a hospital if serum 25(OH)D concentrations were higher than 41 ng/mL and patients were younger than 80. [33] Russian hospitals observed that the likelihood to have severe COVID-19 increases by the factor of 5 if vitamin D is deficient. [27] Similar observations have been made by Panagiotou. [37] Tan et al. (2020) observed a significant reduction in oxygen support for older clients when providing them with a relatively low daily dose of 1000 IU D3 OD, 150 mg magnesium OD, and 500 µg B12 OD upon admission.

Oral supplementation of D3 is the easiest means to prevent deficiencies. A frequent argument against supplementation of vitamin D3 is that an increased intake could lead to a vitamin D toxicity, also called hypervitaminosis D. [36] This again can cause hypercalcemia, which is the buildup of calcium in the blood leading to vascular calcification, osteoporosis, and kidney stones. However, it has been reported that the reason for hypercalcemia rather lays in a vitamin K2 deficiency [17, 46], as K2 activates the bone gamma-carboxyglutamic acid-containing protein (osteocalcin) through carboxylation. Activated osteocalcin deposits calcium in the bones, whereas non-activated osteocalcin inhibits calcium absorption by the bones. As the osteocalcin synthesis rate is increased by higher 25(OH)D serum levels, K2 is required as a natural antagonist. [54, 13]

Given that vitamin D3 is an immunoregulating hormone and can be considered safe when supplementing it together with K2, supplementation of magnesium (200-250 mg/day) should also be considered, as all enzymes that metabolize vitamin D3 seem to require magnesium. (Goddek, 2020).

Quercetin as a Zinc Ionophore

Quercetin, a bioflavonoid polyphenol, has been shown to act as a zinc ionophore, [32] enhancing entrance of zinc into cells to inhibit viral intracellular replication. It is also believed to block viruses from entering cells in the first place. An Oak Ridge National Labs/University of Tennessee study of many FDA-approved compounds presented supercomputer modeling results for inhibition by them of SARS-CoV-2 viral S-spike binding to cells. The study ranked quercetin as fifth out of 20 top performers. [33] Studies have shown quercetin also exhibiting anti-inflammatory properties, [34,36] which could help mitigate the inflammatory response of cytokine and/or bradykinin storms provoked by COVID-19. A wide range of anti-viral/immunity benefits of quercetin have been identified, [37, 41] as well as other health benefits that may address some comorbidities of COVID-19 [42, 44] and some of its sequelae. [44,45]. (Margolin, 2021).

Bromelain, Quercetin, and Curcumin

Due to its proteolytic action, bromelain is absorbed directly when administered orally, while it substantially promotes the absorption of curcumin and Quercetin enhancing its bioavailability and making this a perfect combination of immune-boosting nutraceuticals with synergistic anti-inflammatory and anticoagulant actions. (Panagiotis, et al., 2022).

Glutathione and N-Acetylcysteine

Viral spike proteins play important roles in the viral entry process, facilitating attachment to cellular receptors and fusion of the viral envelope with the cell membrane. Severe acute respiratory syndrome coronavirus 2 (SARS-CoV-2) spike protein binds to the cellular receptor angiotensin converting enzyme-2 (ACE2) via its receptor-binding domain (RBD). The cysteine residue at position 488, consisting of a disulfide bridge with cysteine 480 is located in an important structural loop at ACE2-binding surface of RBD, and is highly conserved among SARS-related coronaviruses. We showed that the substitution of Cys-488 with alanine impaired pseudotyped SARS-CoV-2 infection, syncytium formation, and cell-cell fusion triggered by SARS-CoV-2 spike expression. Consistently, in vitro binding of RBD and ACE2, spike-mediated cell-cell fusion, and pseudotyped viral infection of VeroE6/TMPRSS2 cells were inhibited by the thiol-reactive compounds N-acetylcysteine (NAC) and a reduced form of glutathione (GSH). Furthermore, we demonstrated that the activity of variant spikes from the SARS-CoV-2 alpha and delta strains were also suppressed by NAC and GSH. Taken together, these data indicate that Cys-488 in spike RBD is required for SARS-CoV-2 spike functions and infectivity and could be a target of anti-SARS-CoV-2 therapeutics. (Murae, et al., 2022).

The antiviral activity of glutathione was demonstrated in a study of De Flora et al. [17] who showed that a 6-month preventive administration of N-acetylcysteine (NAC, glutathione precursor) significantly reduced the incidence of clinically apparent influenza and influenza-like episodes, especially in elderly high-risk individuals. In addition, pathophysiological conditions such as lung cell injury and inflammation in patients with severe ARDS were identified as the targets of NAC treatment. In particular, the deficiency of reduced glutathione in the alveolar fluid in acute respiratory distress syndrome (ARDS) patients was found to enhance lung cell injury by ROS/oxidative stress and inflammation, and this damage could be effectively prevented and treated by the administration of NAC. (Polonikov, 2020).

Systemic bioavailability of orally consumed glutathione is poor because the tripeptide is the substrate of proteases (peptidases) of the alimentary canal, and due to the absence of a specific carrier of glutathione at the level of cell membrane. (Allen, 2011), (Witschi, 1992).

Curcumin and Piperine

Orally administered curcumin with piperine could play a multifaceted role in the treatment of COVID-19. The anti-inflammatory and anti-thrombotic properties of curcumin could expedite the recovery of COVID-19 patients, and its antiviral, antibacterial, and antifungal properties could prevent superadded or secondary infections. Our results suggest that the use of orally administered curcumin with piperine as adjuvant therapy in COVID-19 treatment could substantially reduce morbidity and mortality, reduces treatment costs, and decrease logistical burden healthcare systems. Dose-escalating studies have indicated the safety of curcumin over 3 months. Hence, Curcumin can be a safe and natural therapeutic option to prevent post-Covid thromboembolic events (Pawar, 2021).

Curcumin and Bromelain

The coronavirus disease 2019 (COVID-19) pandemic is still ongoing, while no treatment has been proven effective. COVID-19 pathophysiology involves the activation of three main pathways: the inflammatory, the coagulation and the bradykinin cascades. Here, we highlight for the first time the joint potential therapeutic role of bromelain and curcumin, two well-known nutraceuticals, in the prevention of severe COVID-19. Bromelain (a cysteine protease isolated from the pineapple stem) and curcumin (a natural phenol found in turmeric) exert important immunomodulatory actions interfering in the crucial steps of COVID-19 pathophysiology. Their anti-inflammatory properties include inhibition of transcription factors and subsequent downregulation of proinflammatory mediators. They also present fibrinolytic and anticoagulant properties. Additionally, bromelain inhibits cyclooxygenase and modulates prostaglandins and thromboxane, affecting both inflammation and coagulation, and hydrolyzes bradykinin. Interestingly, curcumin has been shown in silico studies to prevent entry of the severe acute respiratory syndrome coronavirus 2 (SARS-CoV-2) into cells as well as viral replication, while a recent experimental study has demonstrated that bromelain may also inhibit viral entry into cells. Notably, bromelain substantially increases the absorption of curcumin after oral administration. To the best of our knowledge, this is the first report highlighting the significance of bromelain and, most importantly, the potential preventive value of the synergistic effects of bromelain and curcumin against severe COVID-19

Clinical studies have demonstrated multiple beneficial effects of bromelain in trauma, ischemic injury, hypertension, atherosclerosis, inflammatory bowel disease, arthritis, and sinusitis as well as antibacterial and antifungal properties [5]. Interestingly, a recent experimental study demonstrated that bromelain inhibits infection of VeroE6 cells by SARS-CoV-2 through blocking the virus binding and entry into cells via downregulation of ACE-2 and TMPRSS2 expression, and cleavage of the SARS-CoV-2 spike protein, presenting a novel promising therapeutic option that warrants further investigation [17]. Due to its proteolytic action, bromelain is absorbed directly when administered orally, while it substantially promotes the absorption of curcumin enhancing its bioavailability and making this a perfect combination of immune-boosting nutraceuticals with synergistic anti-inflammatory and anticoagulant actions [12,16]. (Kritis, 2020).

*Nigella Sativa* as a Zinc Ionophore

Having a range of bioactive components such as thymoquinone and nigellimine, black seed might offer a number of benefits to treat COVID-19 such as (i) blocking the entry of the virus into pneumocytes and (ii) providing ionophore for enhanced uptake of Zn2+ which in turn can enhance host immune response against SARS-CoV-2 as well as inhibit its replication by blocking the viral RdRp. (Rahman, 2020).

Glutathione and Zinc

To improve your glutathione, you need zinc. Another mechanism by which zinc acts as an antioxidant is by affecting the expression of glutamate-cysteine ligase, which is the rate-limiting enzyme of glutathione de novo synthesis. This has a two-fold effect of zinc to neutralize free radicals directly by glutathione or indirectly as a glutathione peroxidase cofactor [15]. Ha et al. [16] showed that the administration of 100-150 mM of zinc in the cultured human retinal pigment epithelial cell line ARPE-19 cells upregulates the mRNA levels of glutamate-cysteine ligase via an nuclear factor erythroid 2 (NFE2)-related factor 2 (Nrf2)-dependent pathway. In this way, zinc modulates the total cellular glutathione concentration [17]. (Marreiro, 2017).

Glutathione and Selenium

Selenium, a nutritionally essential micronutrient, is known for its antioxidant role in mitigating the effects caused by oxidative stress. Being an important component of various antioxidant selenoprotein enzymes like glutathione peroxidase (GPx) and thioredoxin reductase (TrxR), selenium plays an important role in combating oxidative stress caused due to excessive generation of ROS (Tapiero et al., 2003[49]). The antioxidant enzymes like TrxR, apart from maintaining the redox status, also play a crucial role in regulating activities such as cell proliferation, cell death, and immune response activation (Papp et al., 2007[37]). Further, selenoprotein P was found to enhance the activity and expression of glutathione peroxidase in the endothelial cell, thereby protecting the endothelial cells from oxidative damage.

Up-regulation of Nrf2 signaling by selenium has been shown to attenuate lung injury induced by sepsis (Kwon et al., 2016[24]). Activation of the Nrf2 pathway leads to the enhancement of glutathione synthesis and downregulation of the Nf-kβ pathway culminating in decreased lung injury. Conversely, the Nrf2 knockdown experiment had shown inhibition of glutathione synthesis and downregulation of the NF-κB pathway. NF-κB transcription factor is the final common step of the regulation for the expression of inflammatory cytokines. The modulation of its activity has been the target for many anti-inflammatory drugs. The effect of selenium on Nrf2 and NF-κB1 signaling culminates in the regulation of inflammatory cytokines. Selenium supplementations have been found to decrease the production of inflammatory cytokines like IL-6 in cell line studies, animal models, and human studies. (Tomo, 2021).

Glutathione and Astaxanthin

Glutathione and Astaxanthin work synergistically and collectively to form a barrier against pathogens. In this study investigated the effects of 6 mg/day of astaxanthin supplementation on markers of oxidative stress and substrate metabolism during a graded exercise test in active young men. A double-blind, randomized, counterbalanced, crossover design was used. Fourteen men (age=23±2 years) supplemented with 6 mg/day of astaxanthin and a placebo for 4 weeks, with a 1 week washout period between treatments. Following each supplementation period, a fasting blood sample was obtained to measure markers of oxidative stress: glutathione, hydrogen peroxide, advanced oxidation protein products, and malondialdehyde. Participants also completed a graded exercise test after each treatment to determine substrate utilization during exercise at increasing levels of intensity. Glutathione was ~7% higher following astaxanthin compared with placebo (1,233±133 vs. 1,156±185 μM, respectively; p=0.02, d=0.48). Astaxanthin supplementation of 6 mg/day for 4 weeks increased whole blood levels of the antioxidant glutathione in active young men but did not affect oxidative stress markers or substrate utilization during exercise. Astaxanthin appears to be an effective agent to increase endogenous antioxidant status (McAllister, 2022).

All publications, articles, papers, patents, patent publications, and other references cited herein are hereby incorporated by reference herein in their entireties for all purposes.

The foregoing detailed description of the various embodiments of the present teachings has been provided for the purposes of illustration and description. It is not intended to be exhaustive or to limit the present teachings to the precise embodiments disclosed. Many modifications and variations will be apparent to practitioners skilled in this art. The embodiments were chosen and described in order to best explain the principles of the present teachings and their practical application, thereby enabling others skilled in the art to understand the present teachings for various embodiments and with various modifications as are suited to the particular use contemplated. It is intended that the scope of the present teachings be defined by the following claims and their equivalents.

LIST OF REFERENCES

SARS-CoV-2 Spike Proteins (Gupta, 2021). Gupta, D., Sharma, P., Singh, M. et al. Structural and functional insights into the spike protein mutations of emerging SARS-CoV-2 variants. Cell. Mol. Life Sci. 78, 7967-7989 (2021). https://doi.org/10.1007/s00018-021-04008-0

(Lamers, 2022). Lamers, M. M., Haagmans, B. L. SARS-CoV-2 pathogenesis. Nat Rev Microbiol 20, 270-284 (2022). https://doi.org/10.1038/s41579-022-00713-0

[6] Coronaviridae Study Group of the International Committee on Taxonomy of Viruses. The species Severe acute respiratory syndrome-related coronavirus: classifying 2019-nCoV and naming it SARS-CoV-2. Nat. Microbiol. 5, 536-544 (2020).

[7] V'Kovski, P., Kratzel, A., Steiner, S., Stalder, H. & Thiel, V. Coronavirus biology and replication: implications for SARS-CoV-2. Nat. Rev. Microbiol. 19, 155-170 (2021).

[8] Wong, L. R. & Perlman, S. Immune dysregulation and immunopathology induced by SARS-CoV-2 and related coronaviruses—are we our own worst enemy? Nat. Rev. Immunol. 22, 47-56 (2022).

[9] Redondo, N., Zaldivar-Lopez, S., Garrido, J. J. & Montoya, M. SARS-CoV-2 accessory proteins in viral pathogenesis: knowns and unknowns. Front. Immunol. 12, 708264 (2021).

[10] Hulswit, R. J., de Haan, C. A. & Bosch, B. J. Coronavirus spike protein and tropism changes. Adv. Virus Res. 96, 29-57 (2016).

[11] Zhou, P. et al. A pneumonia outbreak associated with a new coronavirus of probable bat origin. Nature 579, 270-273 (2020).

[12] Hoffmann, M. et al. SARS-CoV-2 cell entry depends on ACE2 and TMPRSS2 and is blocked by a clinically proven protease inhibitor. Cell 181, 271-280 e278 (2020).

[13] Li, W. et al. Angiotensin-converting enzyme 2 is a functional receptor for the SARS coronavirus. Nature 426, 450-454 (2003).

[14] Beumer, J. et al. A CRISPR/Cas9 genetically engineered organoid biobank reveals essential host factors for coronaviruses. Nat. Commun. 12, 5498 (2021).

[15] Mykytyn, A. Z. et al. SARS-CoV-2 entry into human airway organoids is serine protease-mediated and facilitated by the multibasic cleavage site. eLife 10, e64508 (2021).

[16] Lamers, M. M. et al. Human airway cells prevent SARS-CoV-2 multibasic cleavage site cell culture adaptation. eLife 10, e66815 (2021).

[17] Hoffmann, M. et al. Chloroquine does not inhibit infection of human lung cells with SARS-CoV-2. Nature 585, 588-590 (2020).

mRNA Vaccine Spike Proteins (Seneff, 2021). International Journal of Vaccine Theory, Practice, and Research: Worse Than the Disease? Reviewing Some Possible Unintended Consequences of the mRNA Vaccines Against COVID-19. Retrieved on 06/11/22 online from https://dpbh.nv.gov/uploadedFiles/dpbhnvgpv/content/Boards/BOH/Meetings/2021/SE NEFF~1.PDF (Beltramello, 2010). Beltramello, M., Williams, K. L., Simmons, C. P., Macagno, A., Simonelli, L., Ha Quyen, N. T . . . . Sallusto, F. (2010). The Human Immune Response to Dengue Virus is Dominated by Highly Cross-Reactive Antibodies Endowed with Neutralizing and Enhancing Activity. Cell Host Microbe 8(3): 271-83. https://doi.org/10.1016/j.chom.2010.08.007.

(Shukla, 2020). Shukla, R., Ramasamy, V., Shanmugam, R. K., Ahuja, R. & Khanna, N. (2020). Antibody-Dependent Enhancement: A Challenge for Developing a Safe Dengue Vaccine. Frontiers in Cellular and Infection Microbiology 10: 572681. https://doi.org/10.3389/fcimb.2020.572681.

(Lee, 2020). Lee, W. S., Wheatley, A. K., Kent, S. J. & DeKosky, B. J. (2020). Antibody-Dependent Enhancement and SARS-CoV-2 Vaccines and Therapies. Nature Microbiology 5(10): 1185-1191. https://doi.org/10.1038/s41564-020-00789-5.

(Vojadani, 2021). Vojdani, A., Vojdani, E., & Kharrazian, D. (2021). Reaction of Human Monoclonal Antibodies to SARS-CoV-2 Proteins with Tissue Antigens: Implications for Autoimmune Diseases. Frontiers in Immunology 11: 3679. https://doi.org/10.3389/fimmu.2020.617089.

(Galeotti, 2020). Galeotti, C., & Bayry, J. (2020). Autoimmune and Inflammatory Diseases Following COVID-19. Nature Reviews Rheumatology, 16(8), 413-414. https://doi.org/10.1038/s41584-020-0448-7.

(Vlachoyiannopoulos, 2020). Vlachoyiannopoulos, P. G., Magira, E., Alexopoulos, H., Jahaj, E., Theophilopoulou, K., Kotanidou, A., & Tzioufas, A. G. (2020). Autoantibodies Related to Systemic Autoimmune Rheumatic Diseases in Severely Ill Patients with COVID-19. Annals of the Rheumatic Diseases 79(12): 1661-1663. http://dx.doi.org/10.1136/annrheumdis-2020-218009.

(Franke, 2021). Franke, C., Ferse, C., Kreye, J., Reincke, S. M., Sanchez-Sendin, E., Rocco, A., . . . & Pruess, H. (2021). High Frequency of Cerebrospinal Fluid Autoantibodies in COVID-19 Patients with Neurological Symptoms. Brain, Behavior, and Immunity 93: 415-419. https://doi.org/10.1016/j.bbi.2020.12.022.

(Zuo, 2020). Zuo, Y., Estes, S. K., Ali, R. A., Gandhi, A. A., Yalavarthi, S., Shi, H., . . . & Knight, J. S. (2020). Prothrombotic Autoantibodies in Serum from Patients Hospitalized with COVID-19. Science Translational Medicine, 12(570): eabd3876. https://doi.org/10.1126/scitranslmed.abd3876.

(Gao, 2020). Gao, Z., Xu, Y., Sun, C., Wang, X., Guo, Y., Qiu, S., & Ma, K. (2020). A systematic review of asymptomatic infections with COVID-19. Journal of Microbiology, Immunology and Infection 54(1): 12-16. https://www.scitencedirect.com/science/article/pil/S1684118220301134.

(Carsetti, 2020). Carsetti, R., Zaffina, S., Piano Mortari, E., Terreri, S., Corrente, F., Capponi, C., . . . & Locatelli, F. (2020). Different Innate and Adaptive Immune Responses to SARS-CoV-2 Infection of Asymptomatic, Mild, and Severe Cases. Frontiers in immunology, 11, 3365. https://www-.frontiersin.org/articles/10.3389/fimmu.2020.3610300/full (Suzuki, 2020). Suzuki, Y. J. (2020). The Viral Protein Fragment Theory of COVID-19 Pathogenesis. Medical Hypotheses 144: 110267.

(Suzuki and Gychka, 2021). Suzuki, Y. J. & Gychka, S. G. (2021). SARS-CoV-2 Spike Protein Elicits Cell Signaling in Human Host Cells: Implications for Possible Consequences of COVID-19 Vaccines. Vaccines 9: 36. https//doi.org/10.3390/cavvines9010036.

(Suzukiet.al., 2021). Suzuki, Y. J., Nikolaienko, S. I., Dibrova, V. A., Dibrova, Y. V., Vasylyk, V. M., Novikov, M. Y. . . . Gychka, S. G. (2021). SARS-CoV-2 Spike Protein-Mediated Cell Signaling in Lung Vascular Cells. Vascular Pharmacology 137: 106823. https://doi.org/10.1016/j.vph.2020.106823.

(Suzuki et.al., 2020). Suzuki, Y. J., Nikolaienko, S. I., Dibrova, V. A., Dibrova, Y. V., Vasylyk, V. M., Novikov, M. Y. . . . Gychka, S. G. (2020). SARS-CoV-2 Spike Protein-Mediated Cell Signaling in Lung Vascular Cells. Vascular Pharmacology 137: 106823. https://www.doi.org/10.1016/j.vph.2020.106823.

(Kuba, 2005). Kuba, K., Imai, Y., Rao, S., Gao, H., Guo, F., Guan, B . . . . Penninger, J. M. (2005). A Crucial Role of Angiotensin Converting Enzyme 2 (ACE2) in SARS Coronavirus-Induced Lung Injury. Natural Medicine 11: 875-879. https://doi.org/10.1038/nm1267.

(Buzhdygana, 2020). Buzhdygana, T. P., DeOrec, B. J., Baldwin-Leclair, A., Bullock, T. A., McGary, H. M . . . . Ramirez, S. H. (2020). The SARS-CoV-2 Spike Protein Alters Barrier Function in 2D Static and 3D Microfluidic in-Vitro Models of the Human Blood-Brain Barrier. Neurobiology of Disease 146: 105131. https://doi.org/10.1016/j.nbd.2020.105131.

(Verma, 2020). Verma, S., Saksena, S. & Sadri-Ardekani, H. (2020). ACE2 Receptor Expression in Testes: Implications in Coronavirus Disease 2019 Pathogenesis. Biology of Reproduction 103(3): 449-451. https://doi.org/10.1093/biolre/ioaa080.

(Navarra, 2020). Navarra, A., Albani, E., Castellano, S., Arruzzolo L., & Levi-Setti P. E. (2020). Coronavirus Disease-19 Infection: Implications on Male Fertility and Reproduction. Frontiers in Physiology 11: 574761. https://www-.doi.org/10.3389/fphys.2020.574761.

(Wang, 2020). Wang, Z. & Xu, X. (2020). ScRNA-seq Profiling of Human Testes Reveals the Presence of the ACE2 Receptor, a Target for SARS-CoV-2 Infection in Spermatogonia, Leydig and Sertoli Cells. Cells 9: 920. https://doi.org/10.3390/cells9040920.

(Achua et.al., 2021). Achua, J. K., Chu, K. Y., Ibrahim, E., Khodamoradi, K., Delma, K. S., Ramsamy, R . . . . Arora, H. (2021). Histopathology and Ultrastructural Findings of Fatal COVID-19 Infections on Testis. The World Journal of Men's Health 39(1): 65-74. https://doi.org/10.5534/wjmh.200170.

(Prusiner, 1982). Prusiner, S. B. (1982). Novel proteinaceous infectious particles cause scrapie Science 216(4542): 136-44. https://www.doi.org/10.1126/science.6801762.

(Weickenmeier, et.al., 2019). Weickenmeier, J., Jucker, M., Goriely, A., and Kuhl, E. (2019). A Physics-based Model Explains the Prion-like Features of Neurodegeneration in Alzheimer's Disease, Parkinson's Disease, and Amyotrophic Lateral Sclerosis. Journal of the Mechanics and Physics of Solids 124: 264-281. https://doi.org/10.1016/j.jmps.2018.10.013.

(Lucchetti et. Al., 2021). Lucchetti, D., Santini, G., Perelli, L., Ricciardi-Tenore, C., Colella, F., Mores, N., . . . . Montuschi, P. (2021). Detection and Characterization of Extracellular Vesicles in Exhaled Breath Condensate and Sputum of COPD and Severe Asthma Patients. European Respiratory Journal Aprril 1; 2003024. [Epub ahead of print]. https://www.doi.org/10.1183/13993003.03024-2020.

Cytokine Storm (Fajgenbaum, 2020). David C. Fajgenbaum, M. D., and Carl H. June, M. D. Cytokine Storm. N Engl J Med 2020; 383: 2255-2273. DOI: 10.1056/NEJMra2026131. https://www.nejm.org/doi/full/10.1056/NEJMra2026131

[14] Sinha P, Matthay M A, Calfee C S. Is a "cytokine storm" relevant to COVID-19?JAMA Intern Med 2020;180: 1152-1154.

[23] Schulert G S, Cron R Q. The genetics of macrophage activation syndrome. Genes Immun 2020;21: 169-181.

[86] Huang K-J, Su I-J, Theron M, et al. An interferon-gamma-related cytokine storm in SARS patients. J Med Virol 2005;75: 185-194.

[87] Moore J B, June C H. Cytokine release syndrome in severe COVID-19. Science 2020;368: 473-474.

[88] The RECOVERY Collaborative Group. Dexamethasone in hospitalized patients with Covid-19—preliminary report. N Engl J Med. DOI: 10.1056/NEJMoa2021436.

[89] Huang C, Wang Y, Li X, et al. Clinical features of patients infected with 2019 novel coronavirus in Wuhan, China. Lancet 2020;395: 497-506.

[90] Zhu Z, Cai T, Fan L, et al. Clinical value of immune-inflammatory parameters to assess the severity of coronavirus disease 2019. Int J Infect Dis 2020;95: 332-339.

[91] Del Valle D M, Kim-Schulze S, Huang H-H, et al. An inflammatory cytokine signature predicts COVID-19 severity and survival. Nat Med 2020;26: 1636-1643.

[93] Caricchio R, Gallucci M, Dass C, et al. Preliminary predictive criteria for COVID-19 cytokine storm. Ann Rheum Dis 2020 Sep. 25 (Epub ahead of print).

[99] Klok F A, Kruip MJHA, van der Meer NJM, et al. Confirmation of the high cumulative incidence of thrombotic complications in critically ill ICU patients with COVID-19: an updated analysis. Thromb Res 2020;191: 148-150

Inflammation (Furman, 2019). Furman D, Campisi J, Verdin E, et al. Chronic inflammation in the etiology of disease across the life span. Nat Med. 2019;25(12): 1822-1832. doi: 10.1038/s41591-019-0675-0.

[1] Furman D et al. Expression of specifc inflammasome gene modules stratifies older individuals into two extreme clinical and immunological states. Nat. Med 23, 174-184 (2017).

[2] Netea M G et al. A guiding map for inflammation. Nat. Immunol 18, 826-831 (2017).

[3] Slavich G M Understanding inflammation, its regulation, and relevance for health: a top scientific and public priority. Brain Behav. Immun 45, 13-14 (2015).

[4] Bennett J M, Reeves G, Billman G E & Sturmberg J P Inflammation-nature's way to efficiently respond to all types of challenges: implications for understanding and managing "the epidemic" of chronic diseases. Front. Med 5, 316 (2018).

[5] GBD 2017 Causes of Death Collaborators. Global, regional, and national age-sex-specific mortality for 282 causes of death in 195 countries and territories, 1980-2017: a systematic analysis for the Global Burden of Disease Study 2017. Lancet 392, 1736-1788 (2018).

[6] Miller G E, Chen E & Parker K J Psychological stress in childhood and susceptibility to the chronic diseases of aging: moving toward a model of behavioral and biological mechanisms. Psychol. Bull 137, 959-997 (2011).

[7] Fleming T P et al. Origins of lifetime health around the time of conception: causes and consequences. Lancet 391, 1842-1852 (2018).

[8] Renz H et al. An exposome perspective: early-life events and immune development in a changing world. J. Allergy Clin. Immunol 140, 24-40 (2017).

[9] Kotas M E & Medzhitov R Homeostasis, inflammation, and disease susceptibility. Cell 160, 816-827 (2015).

[10] Straub R H, Cutolo M, Buttgereit F & Pongratz G Energy regulation and neuroendocrine-immune control in chronic inflammatory diseases. J. Intern. Med 267, 543-560 (2010).

[11] Straub R H, Cutolo M & Pacifici R Evolutionary medicine and bone loss in chronic inflammatory diseases—a theory of inflammation-related osteopenia. Semin. Arthritis Rheum 45, 220-228 (2015).

[12] Straub R H & Schradin C Chronic inflammatory systemic diseases: an evolutionary trade—of between acutely beneficial but chronically harmful programs. Evol. Med. Public Health 2016, 37-51 (2016).

[15] Fullerton J N & Gilroy D W Resolution of inflammation: a new therapeutic frontier. Nat. Rev. Drug Discov 15, 551-567 (2016).

[17] Taniguchi K & Karin M N F-κB, inflammation, immunity and cancer: coming of age. Nat. Rev. Immunol 18, 309-324 (2018).

[18] Gistera A & Hansson G K The immunology of atherosclerosis. Nat Rev. Nephrol 13, 368-380 (2017).

[19] Ferrucci L & Fabbri E Inflammageing: chronic inflammation in ageing, cardiovascular disease, and frailty. Nat. Rev. Cardiol 15, 505-522 (2018).

[20] Heneka M T, Kummer M P & Latz E Innate immune activation in neurodegenerative disease. Nat. Rev. Immunol 14, 463-477 (2014). [PubMed] [Google Scholar]

[21] Miller A H & Raison C L The role of inflammation in depression: from evolutionary imperative to modern treatment target. Nat. Rev. Immunol 16, 22-34 (2016).

[22] Shen-Orr S S et al. Defective signaling in the JAK-STAT pathway tracks with chronic inflammation and cardiovascular risk in aging humans. Cell Syst. 3, 374-384.e4 (2016).

[23] Verschoor C P et al. Serum C-reactive protein and congestive heart failure as signifcant predictors of herpes zoster vaccine response in elderly nursing home residents. J. Infect. Dis 216, 191-197 (2017).

[24] Fourati S et al. Pre-vaccination inflammation and B-cell signalling predict age-related hyporesponse to hepatitis B vaccination. Nat. Commun 7, 10369 (2016).

[25] McDade T W, Adair L, Feranil A B & Kuzawa C Positive antibody response to vaccination in adolescence predicts lower C-reactive protein concentration in young adulthood in the Philippines. Am. J. Hum. Biol 23, 313-318 (2011).

[26] Singer K & Lumeng C N The initiation of metabolic inflammation in childhood obesity. J. Clin. Invest 127, 65-73 (2017).

[27] Olvera Alvarez H A, Kubzansky L D, Campen M J & Slavich G M Early life stress, air pollution, inflammation, and disease: an integrative review and immunologic model of social-environmental adversity and lifespan health. Neurosci. Biobehay. Rev 92, 226-242 (2018).

[33] Jin C, Henao-Mejia J & Flavell R A Innate immune receptors: key regulators of metabolic disease progression. Cell Metab. 17, 873-882 (2013).

[34] Hotamisligil G S Inflammation, metaflammation and immunometabolic disorders. Nature 542, 177-185 (2017).

[35] Kazankov K et al. The role of macrophages in nonalcoholic fatty liver disease and nonalcoholic steatohepatitis. Nat. Rev. Gastroenterol. Hepatol 16, 145-159 (2019).

[36] Redlich K & Smolen J S Inflammatory bone loss: pathogenesis and therapeutic intervention. Nat. Rev. Drug Discov 11, 234-250 (2012).

Long COVID (Theoharides, 2022). Theoharides T C. Could SARS-CoV-2 Spike Protein Be Responsible for Long-COVID Syndrome? Mol Neurobiol. 2022 March; 59(3): 1850-1861. doi: 10.1007/s12035-021-02696-0. Epub 2022 Jan. 13. PMID: 35028901; PMCID: PMC8757925. https://pubmed.ncbi.nlm.nih.gov/35028901/

Nutraceuticals

Vitamin $B_6$ (Pyridoxal 5'-phosphate, Pyridoxine)

(Shakoor, 2021). Shakoor H, Feehan J, Mikkelsen K, et al. Be well: A potential role for vitamin B in COVID-19. Maturitas. 2021;144: 108-111. doi: 10.1016/j.maturitas.2020.08.007

[19] Merigliano C., Mascolo E., Burla R., Saggio I., Verni F. The relationship between vitamin B6, diabetes and cancer. Front. Genet. 2018;9: 388.

[20] Lengyel C. O., Whiting S. J., Zello G. A. Nutrient inadequacies among elderly residents of long-term care facilities. Can. J. Diet. Pract. Res. 2008; 69(2): 82-88.

[21] Nix W.A., Zirwes R., Bangert V., Kaiser R. P., Schilling M., Hostalek U., Obeid R. Vitamin B status in patients with type 2 diabetes mellitus with and without incipient nephropathy. Diabetes Res. Clin. Pract. 2015; 107(4157-165.

[22] Desbarats J. 2020. Pyridoxal 5'-Phosphate to Mitigate Immune Dysregulation and Coagulopathy in COVID-19.

[23] Van Wyk V., Luus H.G., Heyns Ad.P. The in vivo effect in humans of pyridoxal-5'-phosphate on platelet function and blood coagulation. Thrombosis Res. 1992;66(6): 657-668.

[24] Mikkelsen K., Prakash M. D., Kuol N., Nurgali K., Stojanovska L., Apostolopoulos V. Anti-tumor effects of vitamin B2, B6 and B9 in promonocytic lymphoma cells. Int. J. Mol. Sci. 2019;20(15) Vitamin B9 (folic acid, folate)

(Shakoor, 2021). Shakoor H, Feehan J, Mikkelsen K, et al. Be well: A potential role for vitamin B in COVID-19. Maturitas. 2021;144: 108-111. doi: 10.1016/j.maturitas.2020.08.007

[25] Sheybani Z., Dokoohaki M. H., Negandaripour M., Dehdashti M., Zolghadr H., Moghadami M., Masoompour S. M., Zolghadr A. R. 2020. The Role of Folic Acid in the Management of Respiratory Disease Caused by COVID-19.

[26] Kumar V., Jena M. 2020. In Silico Virtual Screening-Based Study of Nutraceuticals Predicts the Therapeutic Potentials of Folic Acid and Its Derivatives Against COVID-19.

Vitamin B12 (Cobalamin)

(Shakoor, 2021). Shakoor H, Feehan J, Mikkelsen K, et al. Be well: A potential role for vitamin B in COVID-19. Maturitas. 2021;144: 108-111. doi: 10.1016/j.maturitas.2020.08.007

[15] Mikkelsen K., Stojanovska L., Prakash M., Apostolopoulos V. The effects of vitamin B on the immune/cytokine network and their involvement in depression. Maturitas. 2017;96: 58-71.

[27] Nemazannikova N., Mikkelsen K., Stojanovska L., Blatch G. L., Apostolopoulos V. Is there a link between vitamin B and multiple sclerosis? Med. Chem. 2018;14(2): 170-180.

[28] Sabry W., Elemary M., Burnouf T., Seghatchian J., Goubran H. Vitamin B12 deficiency and metabolism-mediated thrombotic microangiopathy (MM-TMA) Transfusion Apheresis Sci. 2020; 59(1) [PubMed] [Google Scholar]

[29] Stipp M. M. SARS-CoV-2: micronutrient optimization in supporting host immunocompetence. Int. J. Clin.Case Rep. Rev. 2020; 2(2) [Google Scholar]

[30] Wolffenbuttel B. H. R., Wouters H. J. C. M., Heiner-Fokkema M. R., Van der klauw M. M. The many faces of cobalamin (vitamin B12) deficiency. Mayo Clin. Proc.: Innov. Quality Outcomes. 2019;3(2): 200-214. [PMC free article] [PubMed] [Google Scholar]

[31] Grange S., Bekri S., Artaud-Macari E., Francois A., Girault C., Poitou A. -L., Benhamou Y., Vianey-Saban C., Benoist J. -F., Chatelet V. Adult-onset renal thrombotic microangiopathy and pulmonary arterial hypertension in cobalamin C deficiency. Lancet (London, England) 2015; 386(9997): 1011. [PubMed] [Google Scholar]

[32] dos Santos L. M. J. Can vitamin B12 be an adjuvant to COVID-19 treatment? GSC Biol. Pharm. Sci. 2020;11(3): 1-5. [Google Scholar]

[33] Tan C. W., Ho L. P., Kalimuddin S., Cherng B. P. Z., Teh Y. E., Thien S. Y., Wong H. M., Tern P. J. W., Chay J. W. M., Nagarajan C. A cohort study to evaluate the effect of combination vitamin D, magnesium and vitamin B12 (DMB) on progression to severe outcome in older COVID-19 patients. medRxiv. 2020

Vitamin D (Grant, 2020). Grant W B, Lahore H, McDonnell S L, et al. Evidence that Vitamin D Supplementation Could Reduce Risk of Influenza and COVID-19 Infections and Deaths. Nutrients. 2020; 12(4): 988. Published 2020 Apr. 2. doi: 10.3390/nu12040988 https://pubmed.ncbi.nih.gov/32252338/

[17] Gombart A. F., Pierre A., Maggini S. A Review of Micronutrients and the Immune System-Working in Harmony to Reduce the Risk of Infection. *Nutrients.* 2020; 12:236. doi: 10.3390/nu12010236.

[30] Huang C., Wang Y., Li X., Ren L., Zhao J., Hu Y., Zhang L, Fan G., Xu J., Gu X., et al, Clinical features of patients infected with 2019 novel coronavirus in Wuhan, China. *Lancet.* 2020 doi: 10.1016/S0140-6736(20)30183-5.

[31] Sharifi A., Vahedi H., Nedjat S., Rafiei H., Hosseinzadeh-Attar M. J. Effect of single-dose injection of vitamin D on immune cytokines in ulcerative colitis patients: A randomized placebo-controlled trial. *AMIS.* 2019; 127:681-687, doi: 10.1111/apm,12982.

[40] Lei G. S., Zhang C., Cheng B. H., Lee C. H. Mechanisms of Action of Vitamin D as Supplemental Therapy for Pneumocystis Pneumonia. *Antimicrob. Agents Chemother,* 2017;61 doi: 10.1128/AAC.01226-17.

Mousavi S., Bereswiil S., Heimesaat M. M. Immunomodulatory and Antimicrobial Effects of Vitamin C. *Eur. J. Microbial. Immunol.* 2019; 9:73-79, doi: 10.1556/1886.2019.00016.

[42] Colunga Biancatelli R. M. L., Berrill M., Marik P. E. The antiviral properties of vitamin C, *Expert Rev. Anti Infect. Ther.* 2020; 18:99-101. doi: 10.1080/14787210.2020.1706483.

[43] Wimalawansa S. J. Global epidemic of coronavirus-COVID-19: What we can do to minimze risksl. *Eur. J. Biomed. Pharm, Sci.* 2020; 7:432-438.

[157] Uwitonze A. M., Razzaque M. S. Role of Magnesium in Vitamin D Activation and Function. J. Am. Osteopath Assoc. 2018; 118:181-189. doi: 10.7556/jaoa.2018.037.

(Abdrabbo, 2021). Abdrabbo M, Birch C M, Brandt M, et al. Vitamin D and COVID-19: A review on the role of vitamin D in preventing and reducing the severity of COVID-19 infection. Protein Sci. 2021; 30(11): 2206-2220. doi: 10.1002/pro.4190 Vitamin D and COVID-19: A review on the role of vitamin D in preventing and reducing the severity of COVID-19 infection—PMC (nih.gov)

[69] Antelmann H. Helmann J D. Thiol-based redox switches and gene regulation. *Antiox Redox Signal.* 2011; 14:1049-1063.

[72] Fountain J H, Lappin S L. Physiology, Renin Angiotensin System. 2021 Jul. 22. In: StatPearls [Internet]. Treasure Island (FL): StatPearls Publishing; 2021 January-, PMID: 29261862.

[74] Albashir AAD. Renin-angiotensin-aldosterone system (RAAS) inhibitors and coronavirus disease 2019 (COVID-19). South Med. J. 2021; 114: 51-56.

[77] Dikalov SI, Nazarewicz R R. Angiotensin II-induced production of mitochondrial reactive oxygen species; Potential mechanisms and relevance for cardiovascular disease. *Antiox Redox Signal.* 2013; 19:1085-1094.

[78] Malek Mahdavi A. A brief review of interplay between vitamin D and angiotensin-converting enzyme 2: Implications for a potential treatment for COVID-19. *Rev Med Viral.* 2020; 30:e2119.

[79] Giustarini D, Santucci A, Bartolini D, Galli F, Rossi R. The age-dependent decline of the extracellular thiol-disulfide balance and its role in SARS-CoV-2 infection. *Redox Biol.* 2021; 41:101902.

Vitamin K (Parisi, 2021). Parisi G F, Carota G, Castruccio Castracani C, et al. Nutraceuticals in the Prevention of Viral Infections, including COVID-19, among the Pediatric Population: A Review of the Literature. Int J Mol Sci. 2021; 22(5): 2465. Published 2021 Feb. 28. doi: 10.3390/ijms22052465 https://www.ncbi.nlm.nih.gov/pmc/articles/PMC7957644/

(Green, 2021). Nutrition Insight: Kappa Bioscience uncovers vitamin K2's unique role in immunity and COVID-19. Retrieved on Aug. 8, 2021 online from https://www.nutritioninsight.com/news/kappa-bioscoence-uncovers-vitamin-k2s-unique-role-in-immunity-and-covid-19.html (Kappa, 2020). Kappa Bioscience: COVID-19 and cardiovascular health: the role of K2 in high vitamin D supplementation. Retrieved on Aug. 16, 2021 online from https://www.nutraceuticalbusinessreview.com/news/article_page/COVID-19_and_cardiovascular_health_the_role_of_K2_in_high_vitamin_D_supplementation/171381

Quercetin as a Zinc Ionophore (Di Pierro, 2021). Di Pierro F, Iqtadar S, Khan A, et al. Potential Clinical Benefits of Quercetin in the Early Stage of COVID-19: Results of a Second, Pilot, Randomized, Controlled and Open-Label Clinical Trial. Int J Gen Med. 2021; 14:2807-2816. Published 2021 Jun. 24. doi: 10.2147/IJGM.S318949https://www.ncbi.nlm.nih.gov/pmc/articles/PMC8238537/

[8] Hu B, Huang S, Yin L. The cytokine storm and COVID-19. J Med Virol. 2021; 93(1): 250-256. doi: 10.1002/jmv.26232

[9] Jamilloux Y, Henry T, Belot A, et al. Should we stimulate or suppress immune responses in COVID-19? Cytokine and anti-cytokine interventions. Autoimmun Rev. 2020; 19(7): 102567. doi: 10.1016/j. autrev.2020.102567

[10] Derosa G, Maffioli P, D'Angelo A, Di Pierro F. A role for quercetin in coronavirus disease 2019 (COVID-19). Phytother Res. 2021; 35 (3): 1230-1236. doi: 10.1002/ptr.6887

[11] D'Andrea G. Quercetin: a flavonol with multifaceted therapeutic applications? Fitoterapia. 2015; 106:256-271. doi: 10.1016/j. fitote.2015.09.018

[22] Gao L, Liu G, Wang X, Liu F, Xu Y, Ma J. Preparation of a chemically stable quercetin formulation using nanosuspension technology. Int J Pharm. 2011; 404 (1-2): 231-237. doi: 10.1016/j.ijpharm.2010.11.009

[23] Wang W, Sun C, Mao L, et al. The biological activities, chemical stability, metabolism, and delivery systems of quercetin: a review. Trends Food Sci Technol. 2016; 56:21-38. doi: 10.1016/j.tifs.2016.07.004

(Derosa, 2020). Derosa G, Maffioli P, D'Angelo A, Di Pierro F. A role for quercetin in coronavirus disease 2019 (COVID-19). Phytother Res. 2021 March; 35(3): 1230-1236. doi: 10.1002/ptr.6887. Epub 2020 Oct. 9. PMID: 33034398; PMCID: PMC7675685. https://pubmed.ncbi.nlm.nih.gov/33034398/

(Margolin, 2021). Margolin L, Luchins J, Margolin D, Margolin M, Lefkowitz S. 20-Week Study of Clinical Outcomes of Over-the-Counter COVID-19 Prophylaxis and Treatment. J Evid Based Integr Med. 2021; 26:2515690X211026193. doi: 10.1177/2515690X211026193 https://www.ncbi.nlm.nih.gov/pmc/articles/PMC8264737/

[32] Dabbagh-Bazarbachi H, Clergeaud G, Quesada I M, et al. Zinc ionophore activity of quercetin and epigallocatechin-gallate: from Hepa 1-6 cells to a liposome model. J Agric Food Chem. 2014; 13:8085-8093. doi: 10.1021/jf5014633

[33] Smith M, Smith J C. Repurposing therapeutics for COVID-19: supercomputer-based docking to the SARS-CoV-2 viral spike protein and viral spike protein-human ACE2 interface. Chemrxiv. Preprint. doi: 10.26434/chemrxiv.11871402.v4

[34] Kim Y J, Park W. Anti-inflammatory effect of quercetin on raw 264.7 mouse macrophages induced with polyinosinicpolycytidylic acid. Molecules. 2016;21(4): 450. doi: 10.3390/molecules21040450

[36] Haleagrahara N, Miranda-Hernandez C, Alim A, Hayes L, Bird G, Ketheesan N. Therapeutic effect of quercetin in collageninduced arthritis. Biomed Pharmacother. 2017; 90:38-46. doi: 10. 1016/j.biopha.2017.03.026

[37] Qiu X, Kroeker A, He S, et al. Prophylactic efficacy of quercetin 3-b-o-d-glucoside against ebola virus infection. Antimicrob Agents Chemother. 2016; 60(9): 5182-5188. doi: 10.1128/AAC. 00307-16

[41] Liu H, Lee J I, Ahn T G. Effect of quercetin on the anti-tumor activity of cisplatin in EMT6 breast tumor-bearing mice. Obstet Gynecol Sci. 2019; 62(4): 242-248. doi: 10.5468/ogs.2019.62.4.242

[42] Marunaka Y, Marunaka R, Sun H, et al. Actions of quercetin, a polyphenol, on blood pressure. Molecules. 2017; 22:209. doi: 10. 3390/molecules22020209

[44] Patel R V, Mistry B M, Shinde S K, Syed R, Singh V, Shin H S. Therapeutic potential of quercetin as a cardiovascular agent. Eur J Med Chem. 2018; 155:889-904. doi: 10.1016/j.ejmech. 2018.06.053

[45] Babaei F, Mirzababaei M, Nassiri-Asl M. Quercetin in food: possible mechanisms of its effect on memory. J Food Sci: 2018; 83(9): 2280-2287. doi: 10.1111/1750-3841.14317

Bromelain (Parisi, 2021). Nutraceuticals in the Prevention of Viral Infections, including COVID-19, among the Pediatric Population: A Review of the Literature. Retrieved on Feb. 22, 2022 online at https://www.ncbi.nlm.nih.gov/pmc/articles/PMC7957644/

Pavan R., Jain S., Kumar A. Properties and therapeutic application of bromelain: A review. *Biotechnol. Res. Int* 2012; 2012:976203. doi: 10.1155/2012/976203.

Kritis P., Karampela I., Kokoris S., Dalamaga M. The combination of bromelain and curcumin as an immune-boosting nutraceutical in the prevention of severe COVID-19. *Metabol. Open.* 2020; 8:100066. doi: 10.1016/j.metop.2020.100066.

(Kritis, 2020). Kritis P, Karampela I, Kokoris S, Dalamaga M. The combination of bromelain and curcumin as an immune-boosting nutraceutical in the prevention of severe COVID-19. Metabol Open. 2020; 8:100066. doi: 10.1016/j.metop.2020.100066

[9] Rowan A D, Buttle D J, Barrett A J. The cysteine proteinases of the pineapple plant. Biochem J 1990; 266(3): 869e75.

[10] Bhui K, Prasad S, George J, Shukla Y. Bromelain inhibits COX-2 expression by blocking the activation of MAPK regulated NF-kappa B against skin tumorinitiation triggering mitochondrial death pathway. Canc Lett 2009; 282(2): 167e76. https://doi.org/10.1016/j.canlet.2009.03.003.

[11] Pavan R, Jain S, Shraddha Kumar A. Properties and therapeutic application of bromelain: a review. Biotechnol Res Int 2012: 976203. https://doi.org/10.1155/2012/976203.

[13] Onken J E, Greer P K, Calingaert B, Hale L P. Bromelain treatment decreases secretion of pro-inflammatory cytokines and chemokines by colon biopsies in vitro. Clin Immunol 2008; 126(3): 345e52. https://doi.org/10.1016/j.clim.2007.11.002.

[14] Engwerda C R, Andrew D, Ladhams A, Mynott T L. Bromelain modulates T cell and B cell immune responses in vitro and in vivo. Cell Immunol 2001; 210(1): 66e75. https://doi.org/10.1006/cimm.2001.1807.

[15] Lotz-Winter H. On the pharmacology of bromelain: an update with special regard to animal studies on dose-dependent effects. Planta Med 1990;56(3): 249e53. https://doi.org/10.1055/s-2006-960949.

Zinc (Margolin, 2021). Margolin L, Luchins J, Margolin D, Margolin M, Lefkowitz S. 20-Week Study of Clinical Outcomes of Over-the-Counter COVID-19 Prophylaxis and Treatment. J Evid Based Integr Med. 2021;26: 2515690X211026193. doi: 10.1177/2515690X211026193 https://www.ncbi.nlm.nib.gov/pmc/articles/PMC8264737/

[16] Wessels I, Bolles B, Rink L. The potential impact of zinc supplementation on COVID-19 Pathogenesis. Front Immunol. 2020; 11:1722. doi: 10.3389/fimmu.2020.01712

[17] Skrajnowska D, Bobrowska-Korczak B. Role of zinc in immune system and anti-cancer defense mechanisms. Nutrients. 2019; 11(10): 2273. doi: 10.3390/nu11102273

[18] McCall K A, Huang C, Fierke C A. Function and mechanism of zinc metalloenzymes. J Nutr. 2000; 130: 1437S-1446S. doi: 10. 1093/jn/130.5.1437 S

[19] Roohani N, Hurrell R, Kelishadi R, et al. Zinc and its importance for human health: an integrative review. J Res Med Sci. 2013; 18(2): 144-157. PMID: 23914218; PMCID: PMC3724376.

[20] Prasad A S. Zinc: mechanisms of host defense. J Nutr. 2007; 137(5): 1345-1349. doi: 10.1093/jn/137.5.1345

[21] Shankar A H, Prasad A S. Zinc and immune function: the biological basis of altered resistance to infection. Am J Clin Nutr. 1998; 68(2 Suppl): 4475-463S. doi: 10.1093/ajcn/68.2.447 S

[22] von Bu low V, Dubben S, Engelhardt G, et al. Zinc-dependent suppression of TNF-alpha production is mediated by protein kinase A-induced inhibition of Raf-1, I kappa B kinase beta, and NF-kappa B. J Immunol. 2007; 179(6): 4180. doi: 10.4049/jimmunol.179.6.4180

[23] teVelthuis A J W, van den Worm S H E, Sims A M C, et al. Zinc(2b) inhibits coronavirus and arterivirus RNA polymerase activity in vitro and zinc ionophore block the replication of these viruses in cell culture. PLoS Pathog. 2010; 6(11): e1001176. doi: 10.1371/journal.ppat.1001176

[24] Fosmire G J. Zinc toxicity. Am J Clin Nutr. 1990; 51(2): 225-227. doi: 10.1093/ajcn/51.2.225

[25] https://ods.od.nih.gov/factsheets/Zinc-HealthProfessional/#h8. Accessed May 15, 2020.

[26] Duncan A, Yacoubian C, Watson N, et al. The risk of copper deficiency in patients prescribed zinc supplements. J Cli (Jothimani, et.el., 2020). COVID-19: Poor outcomes in patients with zinc deficiency. Retrieved on 03/31/21 at https://pubmed.ncbi.nlm.nlh.gov/32920234/

[14] Ko Y. L., Morihara D., Shibata K. Factors attenuating zinc deficiency improvement in direct-acting antiviral agent-treated chronic hepatitis C virus infection. Nutrients. 2018; 10(11): 1620. doi: 10.3390/nu10111620. Published 2018 Nov. 2.

[19] Rahman M. T., Idid S. Z. Can Zn Be a critical element in COVID-19 treatment? [published online ahead of print, 2020 May 26] Biol Trace Elem Res. 2020: 1-9. doi: 10.1007/s12011-020-02194-9.

[20] Read S. A., Obeid S., Ahlenstiel C., Ahlenstiel G. The role of zinc in antiviral immunity. Adv Nutr. 2019;10(4): 696-710. doi: 10.1093/advances/nmz013.

[25] to Velthuis A. J., van den Worm S. H., Sims A. C., Baric R. S., Snijder E. J., van Hemert M. J. Zn(2+) inhibits coronavirus and arterivirus RNA polymerase activity in vitro and zinc ionophores block the replication of these viruses in cell culture. PLoS Pathog. 2010; 6(11) doi: 10.1371/journal.ppat.1001176. Published 2010 Nov. 4.

[29] Xue J., Moyer A., Peng B., Wu J., Hannafon B. N., Ding W. Q. Chloroquine is a zinc ionophore. PLoS One. 2014;9(10) doi: 10.1371/journal.pone.0109180. Published 2014 Oct. 1.

Glutathione (Silvagno, 2020). Silvagno F, Vernone A, Pescarmona G P. The Role of Glutathione in Protecting against the Severe Inflammatory Response Triggered by COVID-19. Antioxidants (Basel). 2020; 9(7):624. Published 2020 Jul. 16. doi: 10.3390/antiox9070624

[29] Zhang H., Penninger J. M., Li Y., Zhong N., Slutsky A. S. Angiotensin-converting enzyme 2 (ACE2) as a SARS-CoV-2 receptor: Molecular mechanisms and potential therapeutic target. Intensive. Care Med. 2020;46: 586-590. doi: 10.1007/s00134-020-05985-9.

[30] Walls A. C., Park Y. -J., Tortorici M. A., Wall A., McGuire A. T., Veesler D. Structure, Function, and Antigenicity of the SARS-CoV-2 Spike Glycoprotein. Cell. 2020; 181:281-292. doi: 10.1016/j.cell.2020.02.058.

[31] Glowacka I., Bertram S., Herzog P., Pfefferle S., Steffen I., Muench M. O., Simmons G., Hofmann H., Kuri T., Weber F., et al. Differential downregulation of ACE2 by the spike proteins of severe acute respiratory syndrome coronavirus and human coronavirus NL63. J. Virol. 2010; 84:1198-1205. doi: 10.1128/JVI.01248-09.

[32] Banu N., Panikar S. S., Leal L. R., Leal A. R. Protective role of ACE2 and its downregulation in SARS-CoV-2 infection leading to Macrophage Activation Syndrome: Therapeutic implications. Life Sci. 2020; 256: 117905. doi: 10.1016/j.lfs.2020.117905.

[33] Vajapey R., Rini D., Walston J., Abadir P. The impact of age-related dysregulation of the angiotensin system on mitochondrial redox balance. Front. Physiol. 2014;5 doi: 10.3389/fphys.2014.00439.

[34] DeDiego M. L., Nieto-Torres J. L., Regla-Nava J. A., Jimenez-Guardeno J. M., Fernandez-Delgado R., Fett C., Castano-Rodriguez C., Perlman S., Enjuanes L. Inhibition of NF-B-Mediated Inflammation in Severe Acute Respiratory Syndrome Coronavirus-Infected Mice Increases Survival. J. Virol. 2014;88: 913-924. doi: 10.1128/JVI.02576-13.

[35] Zhang X., Wu K., Wang D., Yue X., Song D., Zhu Y., Wu J. Nucleocapsid protein of SARS-CoV activates interleukin-6 expression through cellular transcription factor NF-κB. Virology. 2007; 365:324-335. doi: 10.1016/j.virol.2007.04.009.

[36] Henry B. M., de Oliveira M. H. S., Benoit S., Plebani M., Lippi G. Hematologic, biochemical and immune biomarker abnormalities associated with severe illness and mortality in coronavirus disease 2019 (COVID-19): A meta-analysis. Clin. Chem. Lab. Med. 2020; 58:1021-1028. doi: 10.1515/cclm-2020-0369. Glutathione Bioavailability (Allen, 2011). Allen J, Bradley R D (September 2011). "Effects of oral glutathione supplementation on systemic oxidative stress biomarkers in human volunteers". Journal of Alternative and Complementary Medicine. 17 (9): 827-33. doi: 10.1089/acm.2010.0716. PMC 3162377. PMID 21875351.

(Witschi, 1992). Witschi A, Reddy S, Stofer B, Lauterburg B H (1992). "The systemic availability of oral glutathione". European Journal of Clinical Pharmacology. 43 (6): 667-9. doi: 10.1007/bf02284971. PMID 1362956. S2CID 27606314.

N-Acetylcysteine (NAC)

(Murae, 2022). Mana Murae, Yoshimi Shimizu, Yuichiro Yamamoto, Asuka Kobayashi, Masumi Houri, Tetsuya Inoue, Takuya Irie, Ryutaro Gemba, Yosuke Kondo, Yoshio Nakano, Satoru Miyazaki, Daisuke Yamada, Akiyoshi Saitoh, Isao Ishii, Taishi Onodera, Yoshimasa Takahashi, Takaji Wakita, Masayoshi Fukasawa, Kohji Noguchi. Biochemical and biophysical research communications 2022 v.597 pp. 30-36: Severe acute respiratory syndrome coronavirus 2, acetylcysteine, alanine, cell membranes, cysteine, disulfide bonds, giant cells, glutathione, mutation, pathogenicity, research, therapeutics. https://pubag.nal.usda.gov/catalog/7659081

(Bourgonje, 2021). Bourgonje A R, Offringa A K, van Eijk L E, Abdulle A E, Hillebrands J L, van der Voort P H J, van Goor H, van Hezik E J. N-Acetylcysteine and Hydrogen Sulfide in Coronavirus Disease 2019. Antioxid Redox Signal. 2021 Mar. 25. Retrieved on Mar. 28, 2021 online from N-Acetylcysteine and Hydrogen Sulfide in Coronavirus Disease 2019—PubMed (nih.gov)

(Shi, 2020). Shi Z, Puyo C A. N-Acetylcysteine to Combat COVID-19: An Evidence Review. Ther Clin Risk Manag. 2020; 16:1047-1055. Published 2020 Nov. 2. doi: 10.2147/TCRM.S273700

[22] Poppe M, Wittig S, Jurida L, et al. The NF-κB-dependent and -independent transcriptome and chromatin landscapes of human coronavirus 229E-infected cells. PLoS Pathog. 2017; 13(3): e1006286. doi: 10.1371/journal.ppat.1006286 [PMC free article] [PubMed] [CrossRef] [Google Scholar]

[23] Geiler J, Michaelis M, Naczk P, et al. N-acetyl-L-cysteine (NAC) inhibits virus replication and expression of pro-inflammatory molecules in A549 cells infected with highly pathogenic H5N1 influenza A virus. Biochem Pharmacol. 2010;79(3): 413-420. doi: 10.1016/j.bcp.2009.08.025 [PubMed] [CrossRef] [Google Scholar]

[24] Ho W, Douglas S D. Glutathione and N-Acetylcysteine suppression of human immunodeficiency virus replication in human Monocyte/Macrophages in vitro. AIDS Res Hum Retroviruses. 1992; 8(7): 1249-1253. doi: 10.1089/aid.1992.8.1249 [PubMed] [CrossRef] [Google Scholar]

[25] Mata M, Sarrion I, Armengot M, et al. Respiratory syncytial virus inhibits ciliagenesis in differentiated normal human bronchial epithelial cells: effectiveness of N-Acetylcysteine. PLoS One. 2012; 7(10): e48037. doi: 10.1371/journal.pone.0048037

(Avdeev, 2022). Avdeev S N, Gaynitdinova V V, Merzhoeva Z M, Berikkhanov Z G. N-acetylcysteine for the treatment of COVID-19 among hospitalized patients. J Infect. 2022; 84(1): 94-118. doi: 10.1016/j.jinf.2021.07.003

[4] Bourgonje A. R., Offringa A. K., van Eijk L. E., Abdulle A. E., Hillebrands J. L., van der Voort P. H. J., et al. N-Acetylcysteine and hydrogen sulfide in Coronavirus disease 2019. Antioxid Redox Signal. 2021 doi: 10.1089/ars.2020.8247.

[5] Renieris G., Katrini K., Damoulari C., Akinosoglou K., Psarrakis C., Kyriakopoulou M., et al. Serum hydrogen sulfide and outcome association in pneumonia by the SARS-CoV-2 coronavirus. Shock. 2020; 54(5): 633-637. doi: 10.1097/SHK.0000000000001562.

[6] Meyer A., Buhl R., Kampf S., Magnussen H. Intravenous N-acetylcysteine and lung glutathione of patients with pulmonary fibrosis and normals. Am J Respir Crit Care Med. 1995; 152(3): 1055-1060. doi: 10.1164/ajrccm.152.3.7663783.

[7] Aldini G., Altomare A., Baron G., Vistoli G., Carini M., Borsani L., Sergio F. N-Acetylcysteine as an antioxidant and disulphide breaking agent: the reasons why. Free Radic Res. 2018; 52(7):751-762. doi: 10.1080/10715762.2018.1468564.

Alpha Lipoic Acid (Sayiner, 2020). Alpha Lipoic Acid as a Potential Treatment for COVID-19-A Hypothesis. Current Topics in Nutraceutical Research. Retrieved on Mar. 28, 2021 online from https://www.researchgate.net/publication/347315012_Alpha_Lipoic_Acid_as_a_Potential_Treatment_for_COVID-19_-_A_Hypothesis (Bodnar, 2017). Chiropractic Economics: The top 3 nutrients that boost mitochondrial function. Retrieved on Jun. 28, 2021 online from The top 3 nutrients that boost mitochondrial function (chiroeco.com)

Selenium (Fakhrolmobasheri, 2021). Fakhrolmobasheri M, Mazaheri-Tehrani S, Kieliszek M, et al. COVID-19 and Selenium Deficiency: a Systematic Review [published online ahead of print, 2021 Nov. 5]. Biol Trace Elem Res. 2021; 1-12. doi: 10.1007/s12011-021-02997-4

[3] Fakhrolmobasheri M, Nasr-Esfahany Z, Khanahmad H, Zeinalian M. Selenium supplementation can relieve the clinical complications of COVID-19 and other similar viral infections. Int J Vitam Nutr Res. 2021; 91:197-199. doi: 10.1024/0300-9831/a000663.

[13] Guillin O M, Vindry C, Ohlmann T, Chavatte L. Selenium, selenoproteins and viral infection. *Nutrients.* 2019; 11:2101. doi: 10.3390/nu11092101.

[20] Heller R A, Sun Q Hackler J, et al. Prediction of survival odds in COVID-19 by zinc, age and selenoprotein P as composite biomarker. *Redox Biol.* 2021; 38:101764. doi: 10.1016/j.redox.2020.101764.

[22] Moghaddam A, Heller R A, Sun Q et al. Selenium deficiency is associated with mortality risk from COVID-19. Nutrients. 2020; 12:2098. doi: 10.3390/nu12072098.

[27] Hackler J, Heller R A, Sun Q, et al. Relation of serum copper status to survival in COVID-19. Nutrients. 2021; 13:1898. doi: 10.3390/nu13061898.

[29] Tomo S, Saikiran G, Banerjee M, Paul S. Selenium to selenoproteins—role in COVID-19. EXCLI J. 2021;20: 781-791. doi: 10.17179/excli2021-3530.

[30] Hu W, Zhao C, Hu H, Yin S. Food sources of selenium and its relationship with chronic diseases. Nutrients. 2021; 13:1739. doi: 10.3390/nu13051739

[31] Kuria A, Tian H, Li M, et al (2020) Selenium status in the body and cardiovascular disease: a systematic review and meta-analysis. Crit Rev Food Sci Nutr: 1-10. 10.1080/10408398.2020.1803200

[56] Harvey W T, Carabelli A M, Jackson B, et al. SARS-CoV-2 variants, spike mutations and immune escape. Nat Rev Microbiol. 2021; 19:409-424. doi: 10.1038/s41579-021-00573-0.

Curcumin (Kritis, 2020). Kritis P, Karampela I, Kokoris S, Dalamaga M. The combination of bromelain and curcumin as an immune-boosting nutraceutical in the prevention of severe COVID-19. Metabol Open. 2020; 8:100066. doi: 10.1016/j.metop.2020.100066

[4] Soni V K, Mehta A, Ratre Y K, Tiwari A K, Amit A, Singh R P, Sonkar S C, Chaturvedi N, Shukla D, Vishvakarma N K. Curcumin, a traditional spice component, can hold the promise against COVID-19? Eur J Pharmacol 2020; 886:73551.

[6] Prasad S, Tyagi A K, Aggarwal B B. Recent developments in delivery, bioavailability, absorption and metabolism of curcumin: the golden pigment from golden spice. Cancer Res Treat 2014; 46(1):2e18. https://doi.org/10.4143/crt.2014.46.1.2.

[7] Xu Y, Liu L. Curcumin alleviates macrophage activation and lung inflammation induced by influenza virus infection through inhibiting the NF-kB signaling pathway. Influenza Other Respir Viruses 2017; 11(5): 457e63. https://doi.org/10.1111/irv.12459.

[8] Praditya D, Kirchhoff L, Brüning J, Rachmawati H, Steinmann J, Steinmann E. Anti-infective properties of the golden spice curcumin. Front Microbiol 2019; 10:912

(Pawar, 2021). Oral Curcumin With Piperine as Adjuvant Therapy for the Treatment of COVID-19: A Randomized Clinical Trial. Retrieved on 061022 online from https://doi.org/10.3389/fphar.2021.669362.

[4] Conti P., Caraffa A., Gallenga C. E., Ross R., Kritas S. K., Frydas I., et al. (2020). IL-1 Induces Throboxane-A2 (TxA2) in COVID-19 Causing Inflammation and Microthrombi: Inhibitory Effect of the IL-1 Receptor Antagonist (IL-1Ra). J. Biol. Regul. Homeost Agents 34 (4), 1623-1627. 10.23812/20-34-4EDIT-65

[24] Shanmugam M., Rane G., Kanchi M., Arfuso F., Chinnathambi A., Zayed M., et al. (2015). The Multifaceted Role of Curcumin in Cancer Prevention and Treatment. Molecules 20 (2), 2728-2769. 10.3390/molecules20022728

[28] Singh K. (2020). Potential Role of Curcumin against Viral Infections with a View on Structure and Pathogenesis of COVID-19. AIJR Preprints. 10.21467/preprints.213

[29] Suresh D., Srinivasan K. (2010). Tissue Distribution & Elimination of Capsaicin, Piperine & Curcumin Following Oral Intake in Rats. Indian J. Med. Res. 131, 682-691.

[35] Zahedipour F., Hosseini S. A., Sathyapalan T., Majeed M., Jamialahmadi T., Al-Rasadi K., et al. (2020). Potential Effects of Curcumin in the Treatment of COVID- 19 Infection. Phytotherapy Res. 34 (11), 2911-2920. 10.1002/ptr.6738 CBDa Cannabidiolic Acid and CBGa Cannabigerolic Acid (Breemen, 2022). van Breemen R B, Muchiri R N, Bates T A, Weinstein J B, Leier H C, Farley S, Tafesse F G. Cannabinoids Block Cellular Entry of SARS-CoV-2 and the Emerging Variants. J Nat Prod. 2022 Jan. 28; 85(1): 176-184. doi: 10.1021/acs.jnatprod.1c00946. Epub 2022 Jan. 10. PMID: 35007072; PMCID: PMC8768006. https://pubmed.ncbi.nlm.nih.gov/35007072/
Cannabidiol (CBD)

(Nguyen, 2021). Nguyen L C, Yang D, Nicolaescu V, et al. Cannabidiol Inhibits SARS-CoV-2 Replication and Promotes the Host Innate Immune Response. Preprint. bioRxiv. 2021; 2021.03.10.432967. Published 2021 Mar. 10. doi: 10.1101/2021.03.10.432967

[12] Marker D. F. et al., The new small-molecule mixed-lineage kinase 3 inhibitor URMC-099 is neuroprotective and anti-inflammatory in models of human immunodeficiency virus-associated neurocognitive disorders. J Neurosci 33, 9998-10010 (2013).

[13] Abu Aboud 0. et al., Dual and Specific Inhibition of NAMPT and PAK4 By KPT-9274 Decreases Kidney Cancer Growth. Mol Cancer Ther 15, 2119-2129 (2016).

(Corpetti, 2021). Corpetti C, Del Re A, Seguella L, Palenca I, Rurgo S, De Conno B, Pesce M, Sarnelli G, Esposito G. Cannabidiol inhibits SARS-Cov-2 spike (S) protein-induced cytotoxicity and inflammation through a PPARγ-dependent TLR4/NLRP3/Caspase-1 signaling suppression in Caco-2 cell line. Phytother Res. 2021 December; 35(12): 6893-6903. doi: 10.1002/ptr.7302. Epub 2021 Oct. 12. PMID: 34643000; PMCID: PMC8662250.

[12] Du, P., Song, C., Li, R., Song, Y., Li, J., Ding, N., . . . Zeng, H. (2020). Specific re-distribution of SARS-CoV-2 variants in the respiratory system and intestinal tract. Clinical Infectious Diseases. 10.1093/cid/ciaa1617

[13] Esposito, G., Pesce, M., Seguella, L., Sanseverino, W., Lu, J., Corpetti, C., & Sarnelli, G. (2020a). The potential of cannabidiol in the COVID-19 pandemic. British Journal of Pharmacology, 177(21), 4967-4970. 10.1111/bph.15157

[19] Khodadadi, H., Salles, E. L., Jarrahi, A., Chibane, F., Costigliola, V., Yu, J. C., Baban, B. (2020). Cannabidiol modulates cytokine storm in acute respiratory distress syndrome induced by simulated viral infection using synthetic RNA. Cannabis and Cannabinoid Research, 5(3), 197-201. 10.1089/can.2020.0043

[27] Nguyen, L. C., Yang, D., Nicolaescu, V., Best, T. J., Ohtsuki, T., Chen, S. N., . . . Rosner, M. R. (2021). Cannabidiol inhibits SARS-CoV-2 replication and promotes the host innate immune response. bioRxiv: The Preprint Server for Biology. 10.1101/2021.03.10.432967

[33] Ribeiro, A., Ferraz-de-Paula, V., Pinheiro, M. L., Vitoretti, L. B., Mariano-Souza, D. P., Quinteiro-Filho, W. M., . . . Palermo-Neto, J. (2012). Cannabidiol, a nonpsychotropic plant-derived cannabinoid, decreases inflammation in a murine model of acute lung injury: Role for the adenosine A(2A) receptor. European Journal of Pharmacology, 678(1-3), 78-85. 10.1016/j.ejphar.2011.12.043

[34] Salles, E. L., Khodadadi, H., Jarrahi, A., Ahluwalia, M., Paffaro, V. A., Jr., Costigliola, V., . . . Baban, B. (2020, Novemmber). Cannabidiol (CBD) modulation of apelin in acute respiratory distress syndrome. Journal of Cellular and Molecular Medicine, 24(21), 12869-12872. 10.1111/jcmm.15883
Cannabigerol (CBG)

(Rossi, 2020). Rossi F, Tortora C, Argenziano M, Di Paola A, Punzo F. Cannabinoid Receptor Type 2: A Possible Target in SARS-CoV-2 (CoV-19) Infection? Int J Mol Sci. 2020 May 27; 21(11): 3809. doi: 10.3390/ijms21113809. PMID: 32471272; PMCID: PMC7312493. Cannabinoid Receptor Type 2: A Possible Target in SARS-CoV-2 (CoV-19) Infection?—PubMed (nih.gov).

[20] Cabral G. A., Ferreira G. A., Jamerson M. J. Endocannabinoids and the Immune System in Health and Disease. Handb. Exp. Pharmacol. 2015; 231:185-211.

[21] Piomelli D. The molecular logic of endocannabinoid signalling. Nat. Rev. Neurosci. 2003; 4:873-884. doi: 10.1038/nrn1247.

[22] Farquhar-Smith W. P., Egertova M., Bradbury E. J., McMahon S. B., Rice A. S., Elphick M. R. Cannabinoid CB(1) receptor expression in rat spinal cord. Mol. Cell Neurosci. 2000; 15:510-521. doi: 10.1006/mcne.2000.0844.

[23] Galiegue S., Mary S., Marchand J., Dussossoy D., Carriere D., Carayon P., Bouaboula M., Shire D., Le Fur G., Casellas P. Expression of central and peripheral cannabinoid receptors in human immune tissues and leukocyte subpopulations. Eur. J. Biochem. 1995; 232:54-61. doi: 10.1111/j.1432-1033.1995.tb20780.x.

[24] Nunez E., Benito C., Pazos M. R., Barbachano A., Fajardo O., Gonzalez S., Tolon R. M., Romero J. Cannabinoid CB2 receptors are expressed by perivascular microglial cells in the human brain: An immunohistochemical study. Synapse. 2004; 53:208-213. doi: 10.1002/syn.20050.

[25] Yao B., Mackie K. Endocannabinoid receptor pharmacology. Curr. Top. Behav. Neurosci. 2009; 1:37-63.

[26] Louvet A., Teixeira-Clerc F., Chobert M. N., Deveaux V., Pavoine C., Zimmer A., Pecker F., Mallat A., Lotersztajn S. Cannabinoid CB2 receptors protect against alcoholic liver disease by regulating Kupffer cell polarization in mice. Hepatology. 2011;54: 1217-1226. doi: 10.1002/hep.24524.

[27] Basu P. P., Aloysius M. M., Shah N. J., Brown R. S., Jr. Review article: The endocannabinoid system in liver disease, a potential therapeutic target. Aliment. Pharmacol. Ther. 2014; 39:790-801. doi: 10.1111/apt.12673.

[28] Howlett A. C., Abood M. E. CB1 and CB2 Receptor Pharmacology. Adv. Pharmacol. 2017; 80:169-206.

[29] Hernandez-Cervantes R., Mendez-Diaz M., Prospero-Garcia O., Morales-Montor J. Immunoregulatory Role of Cannabinoids during Infectious Disease. Neuroimmunomodulation. 2017; 24:183-199. doi: 10.1159/000481824.

[30] Rieder S. A., Chauhan A., Singh U., Nagarkatti M., Nagarkatti P. Cannabinoid-induced apoptosis in immune cells as a pathway to immunosuppression. Immunobiology. 2010; 215:598-605. doi: 10.1016/j.imbio.2009.04.001.

(Paland, 2021). Paland N, Pechkovsky A, Aswad M, et al. The Immunopathology of COVID-19 and the Cannabis Paradigm. Front Immunol. 2021; 12:631233. Published 2021 Feb. 12. doi: 10.3389/fimmu.2021.631233

Wang B, Kovalchuk A, Li D, Ilnytskyy Y, Kovalchuk I, Kovalchuk O. In search of preventative strategies: novel anti-inflammatory high-CBD Cannabis sativa extracts modulate ACE2 expression in COVID-19 gateway tissues. Preprints. (2020). 10.20944/preprints202004.0315.v1

Anil S M, Shalev N, Vinayaka A C, Nadarajan S, Namdar D, Belausov E, et al. Cannabis compounds exhibit anti-inflammatory activity in vitro in COVID-19-related inflammation in lung epithelial cells and pro-inflammatory activity in macrophages. Sci Rep. (2021) 11: 1462. 10.1038/s41598-021-81049-2

Khodadadi H, Salles ÉL, Jarrahi A, Chibane F, Costigliola V, Yu J C, et al. Cannabidiol modulates cytokine storm in acute respiratory distress syndrome induced by simulated viral infection using synthetic RNA. Cannabis Cannabinoid Res. (2020) 5: 197-201. 10.1089/can.2020.0043

131. Salles ÉL, Khodadadi H, Jarrahi A, Ahluwalia M, Paffaro V A, Costigliola V, et al.. Cannabidiol (CBD) modulation of apelin in acute respiratory distress syndrome. J Cell Mol Med. (2020) 24: 12869-72. 10.1111/jcmm.15883

CBD, CBG and the BLOOD-BRAIN-BARRIER (Stone, 2021). Nicole L. Stone, Timothy J. England, and Saoirse E. O'Sullivan.Cannabis and Cannabinoid Research.August 2021.315-326.http://doi.org/10.1089/can.2020.0159

[6] Ceprián M, Jimé nez-Sánchez L, Vargas C, et al. Cannabidiol reduces brain damage and improves functional recovery in a neonatal rat model of arterial ischemic stroke. Neuropharmacology. 2017; 116:151-159.

[7] Rodríguez-Muņoz M, Onetti Y, Cortés-Montero E, et al. Cannabidiol enhances morphine antinociception, diminishes NMDA-mediated seizures and reduces stroke damage via the sigma 1 receptor. Mol Brain. 2018; 11:51.

[8] Lafuente H, Alvarez F J, Pazos M R, et al. Cannabidiol reduces brain damage and improves functional recovery after acute hypoxia-ischemia in new-born pigs. Pediatr Res. 2011; 70:272-277.

[9] Castillo A, Tolón M R, Fernández-Ruiz J, et al. The neuroprotective effect of cannabidiol in an in vitro model of newborn hypoxic-ischemic brain damage in mice is mediated by CB2 and adenosine receptors. Neurobiol Dis. 2010; 37:434-440.

[10] Russo E B, Marcu J. Cannabis pharmacology: the usual suspects and a few promising leads. Adv Pharmacol. 2017; 80:67-134.

[11] Russo E B, Burnett A, Hall B, et al. Agonistic properties of cannabidiol at 5-HT1a receptors. Neurochem Res. 2005; 30:1037-1043.

[12] Hind W H, England T J, O'Sullivan S E. Cannabidiol protects an in vitro model of the blood-brain barrier from oxygen-glucose deprivation via PPARc and 5-HT1A receptors. Br J Pharmacol. 2016; 173:815-825.

[13] Iannotti F A, Hill C L, Leo A, et al. Nonpsychotropic plant cannabinoids, cannabidivarin (CBDV) and cannabidiol (CBD), activate and desensitize transient receptor potential vanilloid 1 (TRPV1) channels in vitro: potential for the treatment of neuronal hyperexcitability. ACS Chem Neurosci. 2014; 5:1131-1141.

[14] England T J, Hind W H, Rasid N A, et al. Cannabinoids in experimental stroke: a systematic review and meta-analysis. J Cereb Blood Flow Metab. 2015; 35:348-358.

[15] Khaksar S, Bigdeli M R. Correlation between cannabidiol-induced reduction of infarct volume and inflammatory factors expression in ischemic stroke model. Basic Clin Neurosci. 2017; 8:139-146.

[16] Pazos M R, Cinquina V, Gómez A, et al. Cannabidiol administration after hypoxia-ischemia to newborn rats reduces long-term brain injury and restores neurobehavioral function. Neuropharmacology. 2012; 63:776783.

[17] Hampson A J, Grimaldi M, Axelrod J, et al. Cannabidiol and (−)D9-tetrahydrocannabinol are neuroprotective antioxidants. Proc Natl Acad Sci USA. 1998; 95:8268-8273.

[18] Sun S, Hu F, Wu J, et al. Cannabidiol attenuates OGD/R-induced damage by enhancing mitochondrial bioenergetics and modulating glucose metabolism via pentose-phosphate pathway in hippocampal neurons. Redox Biol. 2017; 11:577-585.

[19] Mori M A, Meyer E, Soares L M, et al. Cannabidiol reduces neuroinflammation and promotes neuroplasticity and functional recovery after brain ischemia. Prog Neuropsychopharmacol Biol Psychiatry. 2017; 75:94-105.

[20] Gugliandolo A, Pollastro F, Grassi G, et al. In vitro model of neuroinflammation: efficacy of cannabigerol, a non-psychoactive cannabinoid. Int J Mol Sci. 2018;19: 1992.

[21] Giacoppo S, Gugliandolo A, Trubiani O, et al. Cannabinoid CB2 receptors are involved in the protection of RAW264.7 macrophages against the oxidative stress: an in vitro study. Eur J Histochem. 2017; 61:1-13.

[22] Stone N L, Murphy A J, England T J, et al. A systematic review of minor phytocannabinoids with promising neuroprotective potential. Br J Phar macol. 2020; 177: 4330-4352

[29] Borrelli F, Fasolino I, Romano B, et al. Beneficial effect of the nonpsychotropic plant cannabinoid cannabigerol on experimental inflammatory bowel disease. Biochem Pharmacol. 2013; 85:1306-1316.

[30] Echeverry C, Prunell G, Narbondo C, et al. A comparative in vitro study of the neuroprotective effect induced by cannabidiol, cannabigerol, and their respective acid forms: relevance of the 5-HT1A receptors. Neurotox Res. 2021; 39:335-348.

[35] Shaafi S, Sharifipour E, Rahmanifar R, et al. Interleukin-6, a reliable prognostic factor for ischemic stroke. Iran J Neurol. 2014; 13:70-76.

[36] Miao Y, Liao J K. Potential serum biomarkers in the pathophysiological processes of stroke. Expert Review of Neurother. 2014; 14:173-185.

[37] Armstead W M, Hekierski H, Pastor P, et al. Release of IL-6 after stroke contributes to impaired cerebral autoregulation and hippocampal neuronal necrosis through NMDA receptor activation and upregulation of ET1 and JNK. Transl Stroke Res. 2019; 10:104-111.

[38] Beridze M, Sanikidze T, Shakarishvili R, et al. Selected acute phase CSF factors in ischemic stroke: findings and prognostic value. BMC Neurol. 2011; 11:41.

[39] Rochfort K D, Collins L E, Murphy R P, et al. Downregulation of blood-brain-barrier phenotype by proinflammatory cytokines involves NADPH oxidase-dependent ROS generation: consequences for interendothelial adherens and tight junctions. PLoS One. 2014; 9:e101815.

[40] Liu Z, Chopp M. Astrocytes, therapeutic targets for neuroprotection and neurorestoration in ischemic stroke. Prog Neurobiol. 2016; 144:103-120

Cannabinol (CBN)

(NCBI, 2022). National Center for Biotechnology Information. PubChem Compound Summary for CID 2543, Cannabinol. https://pubchem.ncbi.nlm.nih.gov/compound/Cannabinol. Accessed Jun. 10, 2022.

*Nigella Sativa*/Thymoquinone (Rahman, 2020). Rahman M T. Potential benefits of combination of *Nigella sativa* and Zn supplements to treat COVID-19. J Herb Med. 2020; 23:100382. doi: 10.1016/j.hermed.2020.100382. https://www.ncbi.nlm.nih.gov/pmc/articles/PMC7313527/

(Koshak, 2020). Koshak D A E, Koshak P E A. *Nigella sativa* L as a potential phytotherapy for coronavirus disease 2019: A mini review of in silico studies. Curr Ther Res Clin Exp. 2020; 93:100602. doi: 10.1016/j.curtheres.2020.100602. https://www.ncbi.nlm.nih.gov/pmc/articles/PMC7445151/

[24] Bouchentouf S, Noureddine M.Identification of Compounds from *Nigella Sativa* as New Potential Inhibitors of 2019 Novel Coronavirus (COVID-19): Molecular Docking Study Elucidation of neurodegenerative pathologies processes by molecular modeling View project Molecular operating enviro. ChemRxiv. doi: 10.26434/chemrxiv.12055716.v1

[25] Sekiou O, Ismail B, Zihad B, Abdelhak D. In-Silico Identification of Potent Inhibitors of COVID-19 Main Protease (Mpro) and Angiotensin Converting Enzyme 2 (ACE2) from Natural Products: Quercetin, Hispidulin, and Cirsimaritin Exhibited Better Potential Inhibition than Hydroxy-Chloroquine Against. chemRxiv. April 2020 doi: 10.26434/chemrxiv.12181404.v1.

[26] Elfiky A A. Natural products may interfere with SARS-CoV-2 attachment to the host cell. J Biomol Struct Dyn. April 2020: 1-16. doi: 10.1080/07391102.2020.1761881.

[27] Sampangi-ramaiah M H, Vishwakarma R, Shaanker R U. Molecular docking analysis of selected natural products from plants for inhibition of SARS-CoV-2 main protease. Curr Sci. 2020; 118(7): 1087-1092. http://sts-.bioe.uic.edu/castp/index.html?3igg Accessed May 3, 2020.

[28] Rajapaksa R M H, Perera B T, Nisansala M J, Perera WPRT, Dissanayake K G C. POTENTIAL OF INHIBITING THE RECEPTOR BINDING MECHANISM OF SARS-COV-2 USING PHYTOCHEMICAL EXTRACTS OF MEDICINAL HERB; MOLECULER DOCKING STUDY. Glob J Eng Sci Res Manag. 2020; 7(4): 51-61. doi: 10.5281/zenodo.3766184.

[29] da Silva J K R, P L B Figueiredo, Byler K G, Setzer W N. Essential Oils as Antiviral Agents. Potential of Essential Oils to Treat SARS-CoV-2 Infection: An In-Silico Investigation. Int J Mol Sci. 2020; 21(10): 3426. doi: 10.3390/ijms21103426.

[30] Maiti S, Banerjee A, Nazmeen A, Kanwar M, Das S. Active-site Molecular docking of Nigellidine to nucleocapsid/Nsp2/Nsp3/M Pro of COVID-19 and to human IL1R and TNFR1/2 may stop viral-growth/cytokine-flood, and the drug source *Nigella sativa* (black cumin) seeds show potent antioxidant role. Research Square. doi: 10.21203/rs.3.rs-26464/v1

(Muralidharan, 2016). Muralidharan-Chari V, Kim J, Abuawad A, Naeem M, Cui H, Mousa S A. Thymoquinone Modulates Blood Coagulation in Vitro via Its Effects on Inflammatory and Coagulation Pathways. Int J Mol Sci. 2016;17(4): 474. Published 2016 Mar. 30. doi: 10.3390/ijms17040474

Sulforaphane (Ordonez, 2022). Ordonez A A, Bullen C K, Villabona-Rueda A F, et al. Sulforaphane exhibits antiviral activity against pandemic SARS-CoV-2 and seasonal HCoV-OC43 coronaviruses in vitro and in mice. Communications Biology. 2022 March; 5(1): 242. DOI: 10.1038/542003-022-03189-z. PMID: 35304580; PMCID: PMC8933402.

[1] Taylor P C, et al. Neutralizing monoclonal antibodies for treatment of COVID-19. Nat. Rev. Immunol. 2021; 21:382-393.

[7] Jayk Bernal A, et al. Molnupiravir for oral treatment of Covid-19 in nonhospitalized patients. N. Engl. J. Med. 2022;386: 509-520.

[18] Axelsson A S, et al. Sulforaphane reduces hepatic glucose production and improves glucose control in patients with type 2 diabetes. Sci. Transl. Med. 2017;9:eaah4477.

[32] Singh K, et al. Sulforaphane treatment of autism spectrum disorder (ASD) Proc. Natl Acad. Sci. USA. 2014; 111:15550-15555.

[34] Lee C. Therapeutic modulation of virus-induced oxidative stress via the Nrf2-dependent antioxidative pathway. Oxid. Med. Cell Longev. 2018; 2018:6208067.

[36] Siska, P. J. et al. Metabolic imbalance of T cells in COVID-19 is hallmarked by basigin and mitigated by dexamethasone. J. Clin. Invest.131, e148225 (2021).

[37] Dinkova-Kostova A T, et al. Direct evidence that sulfhydryl groups of Keap1 are the sensors regulating induction of phase 2 enzymes that protect against carcinogens and oxidants. Proc. Natl Acad. Sci. USA. 2002; 99:11908-11913.

[38] Hayes J D, Dinkova-Kostova A T. The Nrf2 regulatory network provides an interface between redox and intermediary metabolism. Trends Biochem. Sci. 2014;39: 199-218.

[39] Soares M P, Ribeiro A M. Nrf2 as a master regulator of tissue damage control and disease tolerance to infection. Biochem. Soc. Trans. 2015;43: 663-668.

[41] Kesic M J, Simmons S O, Bauer R, Jaspers I. Nrf2 expression modifies influenza A entry and replication in nasal epithelial cells. Free Radic. Biol. Med. 2011; 51:444-453.

[42] Cho H-Y, et al. Antiviral activity of Nrf2 in a murine model of respiratory syncytial virus disease. Am. J. Respir. Crit. Care Med. 2009; 179:138-150.

[46] Olagnier D, et al. SARS-CoV2-mediated suppression of NRF2-signaling reveals potent antiviral and anti-inflammatory activity of 4-octyl-itaconate and dimethyl fumarate. Nat. Commun. 2020; 11:4938.

[48] Forcados, G. E., Muhammad, A., Oladipo, O.O., Makama, S. & Meseko, C. A. Metabolic implications of oxidative stress and inflammatory process in SARS-CoV-2 pathogenesis: Therapeutic potential of natural antioxidants. Front. Cell Infect. Microbio. 11, 654813 (2021).

[50] Kobayashi E H, et al. Nrf2 suppresses macrophage inflammatory response by blocking proinflammatory cytokine transcription. Nat. Commun. 2016; 7:11624.

[52] Rabbani P S, et al. Dysregulation of Nrf2/Keap1 redox pathway in diabetes affects multipotency of stromal cells. Diabetes. 2019; 68:141-155.

[53] Schmidlin C J, Dodson M B, Madhavan L, Zhang D D. Redox regulation by NRF2 in aging and disease. Free Radic. Biol. Med. 2019; 134:702-707. Astaxanthin (Talukdar, 2020). Jayanta Talukdar, Bhaskar Bhadra, Tomal Dattaroy, Vinod Nagle, Santanu Dasgupta. Potential of natural astaxanthin in alleviating the risk of cytokine storm in COVID-19.

https://reader.elsevier.com/reader/sd/pii/S0753332220310787?token=C99486E1AFD6A002F8711AFB4F054CA56434E9491E3665B327E2A8178A7A242667D4B2B42E0E5C601B92FEF948DF0B14&originRegion=us-east-1&origin-Creation=20220616122332

[8] R. G. Fassett, J. S. Coobes, Astaxanthin: a potential therapeutic agent in cardiovascular disease, Mar. Drugs 9 (2011) 447-465, https://doi.org/10.3390/md9030447.

[9] M. Miyachi, T. Matsuno, K. Asano, I. Mataga, Anti-inflammatory effects of astaxanthin in the human gingival keratinocyte line NDUSD1, J. Clin. Biochem. Nutr. (2015), https://doi.org/10.3164/jcbn.14-109.

[10] G. Hussein, U. Sankawa, H. Goto, K. Matsumoto, H. Watanabe, Astaxanthin, a carotenoid with potential in human health and nutrition, J. Nat. Prod. 69 (2006) 443-449.

[11] J. Dhinaut, A. Balourdet, M. Teixeira, M. Chogne, Y. Moret, A dietary carotenoid reduces immunopathology and enhances longevity through an immune depressive effect in an insect model, Sci. Rep. 7 (2017) 12429, https://doi.org/10.1038/s41598-017-12769-7.

[12] X. Cai, Y. Chen, X. Xiaona, D. Yao, et al., Astaxanthin prevents against lipopolysaccharide-induced acute lung injury and sepsis via inhibiting activation of MAPK/NF-κB, Am. J. Transl. Res. 11 (2019) 1884-1894. PMID: 30972212.

[13] Z. X. Zhang, X. C. Xu, T. Liu, S. Yuan, Mitochondrion-permeable antioxidants to treat ROS-burst-mediated acute diseases, Oxid. Med. Cell. Longev. 2016 (2016) 6859523, https://doi.org/10.1155/2016/6859523.

[14] J. S. Park, J. H. Chyun, Y. K. Kim, L. L. Line, B. P. Chew, Astaxanthin decreased oxidative stress and inflammation and enhanced immune response in humans, Nutr. Metab. 7 (18) (2010), https://doi.org/10.1186/1743-7075-7-18.

[15] H. Jyonouchi, S. Sun, M. Gross, Effect of carotenoids on in vitro immunoglobulin production by human peripheral blood mononuclear cells: astaxanthin, a carotenoid without vitamin A activity, enhances in vitro immunoglobulin production in response to a T-dependent stimulant and antigen, Nutr. Cancer 23 (1995) 171-183, https://doi.org/10.1080/01635589509514373.

[16] Y. Kishimoto, M. Tani, H. U. Kondo, M. Iizuka, et al., Astaxanthin suppresses scavenger receptor expression and matrix metalloproteinase activity in macrophages, Eur. J. Nutr. 49 (2) (2020) 119-126, https://doi.org/10.1007/s00394-009-0056-4.

[17] J. P. Yuan, J. Peng, K. Yin, J. H. Wang, Potential health promoting effects of astaxanthin: a high-value carotenoid mostly from microalgae, Mol. Nutr. Food Res. 55 (2011)150-165.

[37] F. J. Pashkow, D. G. Watumull, C. L. Campbell, Astaxanthin: a novel potential treatment for oxidative stress and inflammation in cardiovascular disease, Am. J. Cardiol. 101 (2008) 58-68, https://doi.org/10.1016/j.amjcard.2008.02.010.

[38] M. Sztretye, B. Dienes, M. Gonczi, et al., Astaxanthin: a potential mitochondrial-targeted antioxidant treatment in diseases and with aging, Oxid. Med. Cell. Longev. 2019 (2019) 3849692, https://doi.org/10.1155/2019/3849692.

[39] V. Sorrenti, S. Davinelli, G. Scapagnini, B. J. Willcox, et al., Astaxanthin as a putative geroprotector: molecular basis and focus on brain aging, Mar. Drugs 18 (2020), https://doi.org/10.3390/md18070351.

[40] S. J. Lee, S. K. Bai, K. S. Lee, et al., Astaxanthin inhibits nitric oxide production and inflammatory gene expression by suppressing I(kappa)B kinase dependent NF-kappaB activation, Mol. Cells 16 (1) (2003) 97-105.

[41] T. R. Campoio, F. A. Oliveira, R. Otton, Oxidative stress in human lymphocytes treated with fatty acid mixture: role of carotenoid astaxanthin, Toxicol. In Vitro 25 (2011) 1448-1456, https://doi.org/10.1016/j.tiv.2011.04.018.

[42] X. Song, B. Wang, et al., Astaxanthin inhibits apoptosis in alveolar epithelial cells type II in vivo and in vitro through the ROS-dependent mitochondrial signaling pathway, J. Cell. Mol. Med. 18 (11) (2014) 2198-2212, https://doi.org/10.1111/jcmm.12347.

[43] J. Bi, R. Cui, Z. Li, C. Liu, J. Zhang, Astaxanthin alleviated acute lung injury by inhibiting oxidative/nitrative stress and the inflammatory response in mice, Biomed. Pharmacother. 95 (2017) 974-982, https://doi.org/10.1016/j.biopha.2017.09.012.

[44] L. Zhou, M. Gao, Z. Xiao, J. Zhang, et al., Protective effect of astaxanthin against multiple organ injury in a rat model of sepsis, J. Surg. Res. 195 (2015) 559-567, https://doi.org/10.1016/j.jss.2015.02.026.

[45] C. Farruggia, M. B. Kim, M. Bae, T. X. Pham, et al., Astaxanthin exerts anti-inflammatory and antioxidant effects in macrophages in NRF2-dependent and independent manners, J. Nutr. Biochem. 62 (2018) 202-209, https://doi.org/10.1016/j.jnutbio.2018.09.005.

[46] T. Iwamoto, K. Hosoda, R. Hirano, H. Kurata, A. Matsumoto, et al., Inhibition of low-density lipoprotein oxidation by astaxanthin, J. Atheroscler. Thromb. 7 (4) (2000) 216-222, https://doi.org/10.5551/jat1994.7.216

[54] X. Zhang, Y. Yue Lu, Q. Wu, et al., Astaxanthin mitigates subarachnoid hemorrhage injury primarily by increasing sirtuin 1 and inhibiting the Toll-like receptor 4 signaling pathway, FASEB J. 33 (1) (2019) 722-737, https://doi.org/10.1096/fj.201800642RR.

[55] J. Peng, J. W. Lu, F. C. Liu, C. H. Lee, Y. J. Ho, et al., Astaxanthin attenuates joint inflammation induced by monosodium urate crystals, FASEB J. 34 (8) (2020) 11215-11226, https://doi.org/10.1096/fj.202000558RR.

[56] Y. H. Kim, H. K. Koh, D. S. Kim, Down-regulation of IL-6 production by astaxanthin via ERK-, MSK-, and NF-kB-mediated signals in activated microglia, Int. Immunopharmacol. 10 (2010) 1560-1572, https://doi.org/10.1016/j.intimp.2010.09.007.

[57] K. Izumi-Nagai, K. Ohgami, S. Satofuka, Y. Ozawa, et al., Inhibition of choroidal neovascularization with an anti-inflammatory carotenoid astaxanthin, Invest. Opthalmol. Vis. Sci. 49 (2008) 1679-1685, https://doi.org/10.1167/iovs.07-1426.

[58] K. C. Chan, P. J. Pen, M. C. Yin, Anticoagulatory and anti-inflammatory effects of astaxanthin in diabetic rats, J. Food Sci. 77 (2012) H76-H80, https://doi.org/10.1111/j.1750-3841.2011.02558.x.

[59] D. Gao, S. Yao, Y. Sun, D. Zheng, Q. Zhang, W. Li, Astaxanthin attenuate iohexol-induced human proximal renal tubular epithelial cells injury via the ROS/NLRP3 inflammasome signal pathway, SDRP J. Food Sci. Technol. 4 (3) (2019), https://doi.org/10.25177/JFST.4.3.RA.503.

[60] X. Zhou, F. Zhang, X. Hu, J. Chen, X. Wen, et al., Inhibition of inflammation by astaxanthin alleviates cognition deficits in diabetic mice, Physiol. Behav. 151 (2015), 412z420, https://doi.org/10.1016/j.physbeh.2015.08.015.

[61] B. P. Chew, J. S. Park, Carotenoids against disease: part C: the immune system and disease, in: G. Britton, S. Liaanen-Jensen, H. Pfander (Eds.), Carotenoids: Nutrition and Health, vol. 5, Birkhauser Press, 2009, pp. 363-382.

[62] K. H. Lin, K. C. Lin, W. J. Lu, P. A. Thomas, et al., Astaxanthin, a carotenoid, stimulates immune responses by enhancing IFN- and IL-2 secretion in primary cultured lymphocytes in vitro and ex vivo, Int. J. Mol. Sci. 17 (2016), https://doi.org/10.3390/ijms17010044.

[63] H. Jyonouchi, L. Zhang, M. Gross, Y. Tomita, Immunomodulating actions of carotenoids: enhancement of in vivo and in vitro antibody production to T-dependent antigens, Nutr. Cancer 21 (1) (1994) 47-58, https://dot.org/10.1080/01635589409514303.

[64] B. Grimmig, S. H. Kim, K. Nash, P. C. Bickford, et al., Neuroprotective mechanisms of astaxanthin: a potential therapeutic role in preserving cognitive function in age and neurodegeneration, Geroscience 39 (2017) 19-32, https://doi.org/10.1007/s11357-017-9958-x (Ahmadi, 2021). Ahmadi A R, Ayazi-Nasrabadi R. Astaxanthin protective barrier and its ability to improve the health in patients with COVID-19. Iran J Microbiol. 2021 August; 13(4):434-441. doi: 10.18502/ijm.v13i4.6965. PMID: 34557270; PMCID: PMC8421583. https://pubmed.ncbi.nlm.nih.gov/34557270/

(Zang, 2020). Zhang, Z, 2020. HINDWAI: Mitochondrion-Permeable Antioxidants to Treat ROS-Burst-Mediated Acute Diseases. Volume 2016 Article ID 6859523. Retrieved on 040520 online from https://www.hindawi.com/journals/omcl/2016/6859523/

(Gleb, 2017). Astaxanthin as a Nootropic: *Astaxanthin's antioxidant properties may help protect the brain from the deleterious effects of aging and neurodegeneration.*

Retrieved on Apr. 15, 2021 online from https://supplementsinreview.com/nootropic/astaxanthin-nootropic/

(Deng, 2017). Deng Z Y, Shan W G, Wang S F, Hu M M, Chen Y. Effects of astaxanthin on blood coagulation, fibrinolysis and platelet aggregation in hyperlipidemic rats. Pharm Biol. 2017; 55(1):663-672. doi: 10.1080/13880209.2016.1261905

Synergistic Combinations

Vitamin D and Magnesium (Grant, 2020). Grant W B, Lahore H, McDonnell S L, et al. Evidence that Vitamin D Supplementation Could Reduce Risk of Influenza and COVID-19 Infections and Deaths. Nutrients. 2020; 12(4):988. Published 2020 Apr. 2. doi: 10.3390/nu12040988 https://pubmed.ncbi.nlm.nih.gov/32252338/

Vitamin D and Glutathione (Abdrabbo, 2021). Abdrabbo M, Birch C M, Brandt M, et al. Vitamin D and COVID-19: A review on the role of vitamin D in preventing and reducing the severity of COVID-19 infection. Protein Sci. 2021; 30(11):2206-2220. doi: 10.1002/pro.4190 Vitamin D and COVID-19: A review on the role of vitamin D in preventing and reducing the severity of COVID-19 infection—PMC (nih.gov)

Vitamin D, Vitamin K, and Magnesium (Goddek, 2020). Goddek S. Vitamin D3 and K2 and their potential contribution to reducing the COVID-19 mortality rate. Int J Infect Dis. 2020 October;99:286-290. doi: 10.1016/j.ijid.2020.07.080. Epub 2020 Aug. 6. PMID: 32768697; PMCID: PMC7406600. https://pubmed.ncbi.nlm.nih.gov/32768697/

[10]

[10] Cortegiani A., Ingoglia G., Ippolito M., Giarratano A., Einav S. A systematic review on the efficacy and safety of chloroquine for the treatment of COVID-19. J Crit Care. 2020; 57:279-283. doi: 10.1016/j.jcrc.2020.03.005.

[13] Dofferhoff A. S. M., Piscaer I., Schurgers L. J., Walk J., van den Ouweland J. M. W., Hackeng T. M. Preprints; 2020. Reduced vitamin K status as a potentially modifiable prognostic risk factor in COVID-19. In preparation.

[17] Flore R., Ponziani F. R., Di Rienzo T. A., Zocco M. A., Flex A., Gerardino L. Something more to say about calcium homeostasis: the role of vitamin K2 in vascular calcification and osteoporosis. Eur Rev Med Pharmacol Sci. 2013; 17:2433-2440.

[19] Grant W. B., Lahore H., McDonnell S. L., Baggerly C. A., French C. B., Aliano J. L. Evidence that vitamin D supplementation could reduce risk of influenza and COVID-19 infections and deaths. Nutrients. 2020; 12:988. doi: 10.3390/nu12040988.

[27] Karonova T. L., Andreeva A. T., Vashukova M. A. уровень 25 (oH)Dв Сыворотке крови у больных COVID-19. Оригинальное исследование 2020:12. doi: 10.22625/2072-6732-2020-12-3-21-2.

[33] Maghbooli Z., Ebrahimi M., Shirvani A., Nasiri M., Pazoki M., Kafan S. Social Science Research Network; Rochester, NY: 2020. Vitamin D Sufficiency Reduced Risk for Morbidity and Mortality in COVID-19 Patients (SSRN Scholarly Paper No. ID 3616008)

[36] Orme R.P., Middleditch C., Waite L., Fricker R. A. Chapter Eleven—The Role of Vitamin D3 in the Development and Neuroprotection of Midbrain Dopamine Neurons. In: Litwack G., editor. Vitamins & hormones, vitamin D hormone. Academic Press; 2016. pp. 273-297.

[37] Panagiotou G., Tee S. A., Ihsan Y., Athar W., Marchitelli G., Kelly D., Boot C. S., Stock N., Macfarlane J., Martineau A. R., Burns G., Quinton R. Low serum 25-hydroxyvitamin D (25[OH]D) levels in patients hospitalized with COVID-19 are associated with greater disease severity. Clin Endocrinol. 2020 doi: 10.1111/cen.14276.

[46] Vermeer C., Theuwissen E. Vitamin K, osteoporosis and degenerative diseases of ageing. Menopause Int. 2011; 17:19-23. doi: 10.1258/mi.2011.011006.

[54] Yasui T., Miyatani Y., Tomita J., Yamada M., Uemura H., Miura M. Effect of vitamin K2 treatment on carboxylation of osteocalcin in early postmenopausal women. Gynecol Endocrinol. 2006; 22:455-459. doi: 10.1080/09513590600900402.

Quercetin as a Zinc Ionophore (Margolin, 2021). Margolin L, Luchins J, Margolin D, Margolin M, Lefkowitz S. 20-Week Study of Clinical Outcomes of Over-the-Counter COVID-19 Prophylaxis and Treatment. J Evid Based Integr Med. 2021; 26:2515690X211026193. doi: 10.1177/2515690X211026193 https://www.ncbi.nlm.nih.gov/pmc/articles/PMC8264737/

Bromelain, Quercetin, and Curcumin (Panagiotis, 2022). Kritis P, Karampela I, Kokoris S, Dalamaga M. The combination of bromelain and curcumin as an immune-boosting nutraceutical in the prevention of severe COVID-19. Metabol Open. 2020 December; 8:100066. doi: 10.1016/j.metop.2020.100066. Epub 2020 Nov. 13. PMID: 33205039; PMCID: PMC7661945.

Glutathione, N-acetylcysteine, and Alpha Lipoic Acid (Murae, et al., 2022). Biochemical and Biophysical Research Communications: The function of SARS-CoV-2 spike protein is impaired by disulfide-bond disruption with mutation at cysteine-488 and by thiol-reactive N-acetylcysteine and glutathione. Retrieved on 060722 online from https://www.sciencedirect.com/science/article/pii/S0006291X22001383?via%3Dihub#!

(Polonikov, 2020). Polonikov A. Endogenous Deficiency of Glutathione as the Most Likely Cause of Serious Manifestations and Death in COVID-19 Patients. ACS Infect Dis. 2020; 6(7): 1558-1562. doi: 10.1021/acsinfecdis.0c00288

[17] De Flora S.; Grassi C.; Carati L. (1997) Attenuation of influenza-like symptomatology and improvement of cell-mediated immunity with long-term N-acetylcysteine treatment. Eur. Respir. J. 10, 1535-1541. 10.1183/09031936.97.10071535

(Sayiner, 2020). Alpha Lipoic Acid as a Potential Treatment for COVID-19-A Hypothesis. Current Topics in Nutraceutical Research. Retrieved on Mar. 28, 2021 online from https://www.researchgate.net/publication/347315012_Alpha_Lipoic_Acid_as_a_Potential_Treatment_for_COVID-19_-_A_Hypothesis (Allen, 2011). Allen J, Bradley R D (September 2011). "Effects of oral glutathione supplementation on systemic oxidative stress biomarkers in human volunteers". Journal of Alternative and Complementary Medicine. 17 (9): 827-33. doi: 10.1089/acm.2010.0716. PMC 3162377. PMID 21875351.

(Witschi, 1992). Witschi A, Reddy S, Stofer B, Lauterburg B H (1992). "The systemic availability of oral glutathione". European Journal of Clinical Pharmacology. 43 (6): 667-9. doi: 10.1007/bf02284971. PMID 1362956. S2CID 27606314.

Curcumin and Piperine (Pawar, 2021). Oral Curcumin With Piperine as Adjuvant Therapy for the Treatment of COVID-19: A Randomized Clinical Trial. Retrieved on 061022 online from https://doi.org/10.3389/fphar.2021.669362.

[4] Conti P., Caraffa A., Gallenga C. E., Ross R., Kritas S. K., Frydas I., et al. (2020). IL-1 Induces Throboxane-A2 (TxA2) in COVID-19 Causing Inflammation and Microthrombi: Inhibitory Effect of the IL-1 Receptor Antagonist (IL-1Ra). J. Biol. Regul. Homeost Agents 34 (4), 1623-1627. 10.23812/20-34-4EDIT-65

[24] Shanmugam M., Rane G., Kanchi M., Arfuso F., Chinnathambi A., Zayed M., et al. (2015). The Multifaceted Role of Curcumin in Cancer Prevention and Treatment. Molecules 20 (2), 2728-2769. 10.3390/molecules20022728

[28] Singh K. (2020). Potential Role of Curcumin against Viral Infections with a View on Structure and Pathogenesis of COVID-19. AIJR Preprints. 10.21467/preprints.213

[29] Suresh D., Srinivasan K. (2010). Tissue Distribution & Elimination of Capsaicin, Piperine & Curcumin Following Oral Intake in Rats. Indian J. Med. Res. 131, 682-691.

[35] Zahedipour F., Hosseini S. A., Sathyapalan T., Majeed M., Jamialahmadi T., Al-Rasadi K., et al. (2020). Potential Effects of Curcumin in the Treatment of COVID-19 Infection. Phytotherapy Res. 34 (11), 2911-2920. 10.1002/ptr.6738

Curcumin and Bromelain (Kritis, 2020). Kritis P, Karampela I, Kokoris S, Dalamaga M. The combination of bromelain and curcumin as an immune-boosting nutraceutical in the prevention of severe COVID-19. Metabol Open. 2020; 8:100066. doi: 10.1016/j.metop.2020.100066

[5] Rathnavelu V, Alitheen N B, Sohila S, Kanagesan S, Ramesh R. Potential role of bromelain in clinical and therapeutic applications. Biomed Rep 2016; 5(3):283e8.

[12] Wallace J M. Nutritional and botanical modulation of the inflammatory cascade-eicosanoids, cyclooxygenases, and lipoxygenases—as an adjunct in cancer therapy. Integr Canc Ther 2002; 1(1): 7e37. https://doi.org/10.1177/153473540200100102.

[16] Taussig S J, Batkin S. Bromelain, the enzyme complex of pineapple (Ananas comosus) and its clinical application. An update. J Ethnopharmacol 1988; 22(2): 191e203. https://doi.org./10.1016/0378-8741(88)90127-4.

[17] Sagar S, Rathinavel A K, Lutz W E, Struble L R, Khurana S, Schnaubelt A T, Mishra N K, Guda C, Broadhurst M J, Reid S P M, Bayles K W, Borgstahl G E O, Radhakrishnan P. Bromelain inhibits SARS-CoV-2 infection in VeroE6 cells. 2020. https://doi.org/10.1101/2020.09.16.297366. bioRxiv [Preprint]. 2020.09.16.297366

*Nigella Sativa* as a Zinc Ionophore (Rahman, 2020). Rahman M T. Potential benefits of combination of *Nigella sativa* and Zn supplements to treat COVID-19. J Herb Med. 2020; 23:100382. doi: 10.1016/j.hermed.2020.100382. https://www.ncbi.nlm.nih.gov/pmc/articles/PMC7313527/

Glutathione and Zinc (Marreiro, 2017). Marreiro D D, Cruz K J, Morais J B, Beserra J B, Severo J S, de Oliveira A R. Zinc and Oxidative Stress: Current Mechanisms. Antioxidants (Basel). 2017; 6(2):24. Published 2017 Mar. 29. doi: 10.3390/antiox6020024

Glutathione and Selenium (Tomo, 2021). Tomo S, Saikiran G, Banerjee M, Paul S. Selenium to selenoproteins—role in COVID-19. EXCLI J. 2021; 20:781-791. Published 2021 Apr. 16. doi: 10.17179/excli2021-3530

Glutathione and Astaxanthin (McAllister, 2022). McAllister M J, Mettler J A, Patek K, Butawan M, Bloomer R J. Astaxanthin Supplementation Increases Glutathione Concentrations but Does Not Impact Fat Oxidation During Exercise in Active Young Men. Int. J Sport Nutr Exerc Metab. 2022 Jan. 1; 32(1): 8-15. doi: 10.1123/ijsnem.2021-0138. Epub 2021 Oct. 5. PMID: 34611051. https://pubmed.ncbi.nlm.nih.gov/34611051/

Background

Ali, N. (2020). Role of Vitamin D in Preventing of COVID-19 Infection, Progression and Severity. Journal of Infection and Public Health 13(10): 1373-1380. https://doi.org/10.1016/j.jiph.2020.06.021.

Rico-Campà, A., Martínez-González, M. A., Alvarez-Alvarez, I., de Deus Mendonça, R., de la Fuente-Arrillaga, C., Gómez-Donoso, C. & Bes-Rastrollo, M. (2019). Association Between Consumption of Ultra-Processed Foods and All Cause Mortality: SUN Prospective Cohort Study. Journal of Infection and Public Health 13(10): 1373-1380. https://pubmed.ncbi.nlm.nih.gov/31142450/

Sarohan, A. R. (2020). COVID-19: Endogenous Retinoic Acid Theory and Retinoic Acid Depletion Syndrome. Medical Hypotheses 144:110250. https://www.doi.org/10.1016/j.mehy.2020.110250.

(Fajgenbaum, 2020). The New England Journal of Medicine: Cytokine Storm. Retrieved on Feb. 20, 2022 online from Cytokine Storm|NEJM (Scudellari, 2021). Nature: *How the coronavirus infects cells—and why Delta is so dangerous*. Retrieved on Feb. 21, 2022 online at https://www.nature.com/articles/d41586-021-02039-y (Immanuel, 2022). Front Line COVID-19 Critical Care Alliance. Retrieved on Apr. 25, 2022 online at https://covid19criticalcare.com/.

(Wong, 2021). Inflammation in COVID-19: *from pathogenesis to treatment*. Retrieved on Feb. 22, 2022 online from https://www.ncbi.nlm.nih.gov/pmc/articles/PMC8339720/

(Gleb, 2017). Astaxanthin as a Nootropic: *Astaxanthin's antioxidant properties may help protect the brain from the deleterious effects of aging and neurodegeneration*. Retrieved on Apr. 15, 2021 online from https://supplementsinreview.com/nootropic/astaxanthin-nootropic/

(Richards, 2019). Pro Health: *The Most Powerful Natural Antioxidant Discovered To Date—Hydroxytyrosol*. Retrieved on May 22, 2021 online from https://www.pro-health.com/library/the-most-powerful-natural-antioxodant-discovered-to-date-hydroxytyrosol-29641

(Ordonez, et al., 2022). Ordonez A A, Bullen C K, Villabona-Rueda A F, et al. Sulforaphane exhibits antiviral activity against pandemic SARS-CoV-2 and seasonal HCoV-OC43 coronaviruses in vitro and in mice. Communications Biology. 2022 Mar. 5(1): 242. DOI: 10.1038/s42003-022-03189-z. PMID: 35304580; PMCID: PMC8933402. https://europepmc.org/article/PMC/8933402

(Gupta, 2021). Gupta D, Sharma P, Singh M, Kumar M, Ethayathulla AbS, Kaur P. Structural and functional insights into the spike protein mutations of emerging SARS-CoV-2 variants. Cell Mol Life Sci. 2021 December; 78(24): 7967-7989. doi: 10.1007/s00018-021-04008-0. Epub 2021 Nov. 3. PMID: 34731254.,https://pubmed.ncbi.nlm.nih.gov/34731254/

What I claim is:

1. A nutraceutical composition comprising Cannabidiolic Acid, Cannabigerolic Acid, Cannabidiol, Cannabigerol, Vitamin D3, Vitamin K2, Magnesium, Quercetin, Zinc, Bromelain, *Nigella Sativa*/Thymoquinone, and Astaxanthin each present in therapeutically effective amounts, in an admixture with a nutraceutically acceptable excipient, wherein the therapeutic effective amount for each of the named nutraceuticals is provided in a single or divided doses of twice daily or thrice daily, and wherein the therapeutic effective amount of Quercetin ranges from 125 mg to 500 mg, the therapeutic effective amount of Zinc ranges from 15 mg to 50 mg, the therapeutic effective amount of Vitamin D3 ranges from 100 mcg to 200 mcg, the therapeutic effective amount of Vitamin K2 ranges from 100 mcg to 200 mcg, the therapeutic effective amount of Magnesium ranges from 30 mg to 200 mg, the therapeutic effective amount of Bromelain ranges from 25 mg to 250 mg, the therapeutic effective amount of Cannabidiolic Acid ranges from 5 mg to 60 mg, the therapeutic effective amount of Cannabigerolic Acid 5 mg to 60 mg, the therapeutic effective amount of Cannabidiol ranges from 5 mg to 60 mg, the therapeutic effective amount of Cannabigerol ranges from 5 mg to 60 mg, the therapeutic effective amount of *Nigella Sativa*/Thymoquinone ranges from 100 mg to 1000 mg, and the therapeutic effective amount of Astaxanthin ranges from 4 mg to 12 mg.

2. The nutraceutical composition of claim 1, wherein the therapeutic effective amount for each of the named nutraceuticals is provided in a single or divided doses of twice daily or thrice daily, and wherein the therapeutic effective amount of Quercetin ranges from 140 mg to 450 mg, the therapeutic effective amount of Zinc ranges from 20 mg to 45 mg, the therapeutic effective amount of Vitamin D3 ranges from 90 mcg to 180 mcg, the therapeutic effective amount of Vitamin K2 ranges from 90 mcg to 180 mcg, the therapeutic effective amount of Magnesium ranges from 40 mg to 180 mg, the therapeutic effective amount of Bromelain ranges from 30 mg to 225 mg, the therapeutic effective amount of Cannabidiolic Acid ranges from 10 mg to 50 mg, the therapeutic effective amount of Cannabigerolic Acid 10 mg to 50 mg, the therapeutic effective amount of Cannabidiol ranges from 10 mg to 50 mg, the therapeutic effective amount of Cannabigerol ranges from 10 mg to 50 mg, the therapeutic effective amount of *Nigella Sativa*/Thymoquinone ranges from 150 mg to 900 mg, and the therapeutic effective amount of Astaxanthin ranges from 6 mg to 10 mg.

3. The nutraceutical composition of claim 1, wherein the therapeutic effective amount for each of the named nutraceuticals is provided in a single or divided doses of twice daily or thrice daily, and wherein the therapeutic effective amount of Quercetin ranges from 175 mg to 500 mg, the therapeutic effective amount of Zinc ranges from 30 mg to 50 mg, the therapeutic effective amount of Vitamin D3 ranges from 120 mcg to 200 mcg, the therapeutic effective amount of Vitamin K2 ranges from 120 mcg to 200 mcg, the therapeutic effective amount of Magnesium ranges from 60 mg to 200 mg, the therapeutic effective amount of Bromelain ranges from 50 mg to 250 mg, the therapeutic effective amount of Cannabidiolic Acid ranges from 15 mg to 60 mg, the therapeutic effective amount of Cannabigerolic Acid 15 mg to 60 mg, the therapeutic effective amount of Cannabidiol ranges from 15 mg to 60 mg, the therapeutic effective amount of Cannabigerol ranges from 15 mg to 60 mg, the therapeutic effective amount of *Nigella Sativa*/Thymoquinone ranges from 200 mg to 1000 mg, and the therapeutic effective amount of Astaxanthin ranges from 8 mg to 12 mg.

4. The nutraceutical composition of claim 1, wherein the therapeutic effective amount for each of the named nutraceuticals is provided in a single or divided doses of twice daily or thrice daily, and wherein the therapeutic effective amount of Quercetin ranges from 125 mg to 400 mg, the therapeutic effective amount of Zinc ranges from 15 mg to 40 mg, the therapeutic effective amount of Vitamin D3 ranges from 100 mcg to 150 mcg, the therapeutic effective amount of Vitamin K2 ranges from 100 mcg to 150 mcg, the therapeutic effective amount of Magnesium ranges from 30 mg to 150 mg, the therapeutic effective amount of Bromelain ranges from 25 mg to 175 mg, the therapeutic effective amount of Cannabidiolic Acid ranges from 5 mg to 40 mg, the therapeutic effective amount of Cannabigerolic Acid 5 mg to 40 mg, the therapeutic effective amount of Cannabidiol ranges from 5 mg to 40 mg, the therapeutic effective amount of Cannabigerol ranges from 5 mg to 40 mg, the therapeutic effective amount of *Nigella Sativa*/Thymoquinone ranges from 100 mg to 800 mg, and the therapeutic effective amount of Astaxanthin ranges from 4 mg to 8 mg.

5. The nutraceutical composition of claim 1, wherein the therapeutic effective amount for each of the named nutraceuticals is provided in a single or divided doses of twice daily or thrice daily, and wherein the therapeutic effective amount of Quercetin ranges from 250 mg to 350 mg, the therapeutic effective amount of Zinc ranges from 30 mg to 40 mg, the therapeutic effective amount of Vitamin D3 ranges from 120 mcg to 160 mcg, the therapeutic effective amount of Vitamin K2 ranges from 120 mcg to 160 mcg, the therapeutic effective amount of Magnesium ranges from 30 mg to 200 mg, the therapeutic effective amount of Bromelain ranges from 100 mg to 200 mg, the therapeutic effective amount of Cannabidiolic Acid ranges from 15 mg to 40 mg, the therapeutic effective amount of Cannabigerolic Acid 15 mg to 40 mg, the therapeutic effective amount of Cannabidiol ranges from 15 mg to 40 mg, the therapeutic effective amount of Cannabigerol ranges from 15 mg to 40 mg, the therapeutic effective amount of *Nigella Sativa*/Thymoquinone ranges from 250 mg to 750 mg, and the therapeutic effective amount of Astaxanthin ranges from 6 mg to 10 mg.

* * * * *